US005756102A

United States Patent [19]

Paoletti et al.

[11] Patent Number: 5,756,102
[45] Date of Patent: May 26, 1998

[54] POXVIRUS-CANINE DISTEMPER VIRUS (CDV) RECOMBINANTS AND COMPOSITIONS AND METHODS EMPLOYING THE RECOMBINANTS

[75] Inventors: Enzo Paoletti, Delmar; James Tartaglia, Schenectady; Jill Taylor, Albany, all of N.Y.

[73] Assignee: Virogenetics Corporation, Troy, N.Y.

[21] Appl. No.: 224,657

[22] Filed: Apr. 6, 1994

Related U.S. Application Data

[63] Continuation-in-part of Ser. No. 105,483, Aug. 12, 1993, Pat. No. 5,494,807, Ser. No. 73,962, Jun. 8, 1993, Pat. No. 5,503,834, and Ser. No. 938,283, Aug. 31, 1992, abandoned, which is a continuation-in-part of Ser. No. 621,614, Nov. 30, 1990, abandoned, said Ser. No. 73,962, is a continuation of Ser. No. 776,867, Oct. 22, 1991, abandoned, which is a continuation-in-part of Ser. No. 621,614, said Ser. No. 105,483, is a continuation of Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, abandoned.

[51] Int. Cl.$^6$ ............... A61K 39/175; A61K 39/275; A61K 39/285; C12N 7/01
[52] U.S. Cl. ............... 424/199.1; 435/69.3; 435/235.1; 435/320.1; 424/213.1; 424/232.1
[58] Field of Search ............... 435/235.1, 320.1, 435/172.3, 69.3; 424/186.1, 199.1, 213.1, 232.1; 934/32, 65

[56] References Cited

U.S. PATENT DOCUMENTS

| | | | |
|---|---|---|---|
| 5,093,258 | 3/1992 | Cohen et al. | 435/235.1 |
| 5,110,587 | 5/1992 | Paoletti | 435/235.1 |
| 5,155,020 | 10/1992 | Paoletti | 435/69.1 |
| 5,174,993 | 12/1992 | Paoletti | 424/199.1 |
| 5,180,675 | 1/1993 | Drillien | 435/234.1 |
| 5,225,336 | 7/1993 | Paoletti | 435/69.1 |

FOREIGN PATENT DOCUMENTS

| | | |
|---|---|---|
| 0314569 | 5/1989 | European Pat. Off. |
| WO-8903429 | 4/1989 | WIPO |
| WO-9010693 | 9/1990 | WIPO |
| WO-9012101 | 10/1990 | WIPO |

OTHER PUBLICATIONS

Gouveia, A.M.G. et al. Arquivo Brasiliero de Medicina Veterinaria e Zootecnia, vol. 39, p. 539–545 (abstract only), 1987.
Colzani, G. et al. Bolletino Associazione Italia Veterinari per Piccolo Animali, vol. 26, p. 173–179 (abstract only), 1987.
Povey, R.C. Canadian Veterinary Journal, vol. 27, p. 321–232 (abstract only), 1986.
Sprino, P.J. et al. Veterinary Medicine & Small Animal Clinician, vol. 78, p. 337–339 (abstract only), 1983.
Ruth, D.T. et al. Veterinary Medicine & Small Animal Clinician, vol. 76, pp. 830–832 (abstract only), 1981.
Chappuis, G. et al. Revue de Medecine Veterinare, vol. 124, pp. 877–897 (abstract only), 1973.
Kolb, S. et al. Kleintierpraxis, vol. 40, pp. 919–928 (abstract only), 1995.
Wu, W. et al. Acta Veterinaria et Zootechnica Sinica, vol. 24, pp. 165–169 (abstract only), 1993.
Cooper, P.E. et al. Bulletin Mensual de la Societe Veterinaire Pratique de France, vol. 75, pp. 131–152 (abstract only), 1991.
Acree, W.M. et al. Canine Practice, vol. 9, pp. 19–21 (abstract only), 1982.
Wild, T.F. et al. 1993. Vaccine vol. 11 pp. 438–444.
Yilma, T. et al. 1988. Science vol. 242 pp. 1058–1061.
Adams, J.M., and D.T. Imagawa, Proc. Soc. Exper. Biol. Med. 96, 240–244 (1957).
Adamowicz, Ph., F. Tron, R. Vinas, M.N. Mevelec, I. Diaz, A.M. Courouce, M. C. Mazert, D. Lagarde and M. Girard, In Viral Hepatitis and Liver Disease, pp. 1087–1090 (1988).
Albrecht, P., K. Herrman, and G.R. Burns, J. Virol. Methods 3, 251–260 (1981).
Alexander, D.J. In Diseases of Poultry, 9th edition, eds. B.W. Calnek, H.J. Barnes, C.W. Beard, W.M. Reid and H.W. Yoder, Jr., (Iowa State University Press, Ames, Iowa, USA) pp. 496–519 (1991).
Alkhatib, G., and D. Briedis, Virology 150, 479–490 (1986).
Alkhatib, G., C. Richardson, and S–H. Shen, Virology 175, 262–270 (1990).
Allen, P. and Rapp, F., J. Infect. Dis. 145, 413–421 (1982).
Alp, N.J., T.D. Allport, J. Van Zanken, B. Rodgers, J.G.P. Sissons, and L.K. Borysiewicz, J. Virol. 65, 4812–4820 (1991).
Altenburger, W., C–P. Suter and J. Altenburger, Archives Virol. 105, 15–27 (1989).
Appel, M.J.G. and O.R. Jones, Proc. Soc. Exp. Biol. and Med. 126, 571–574 (1967).
Appel, M.J.G. and D.S. Robson, Am. J. Vet. Res. 34, 1459–1463 (1973).
Arikawa, J., Schmaljohn, A.L., Dalrymple, J.M., and Schmaljohn, D.C., J. Gen. Virology 70, 615–624 (1989).
Asada, H., Tamura, M., Dondo, K., Dohi, Y, Yamanishi, K., J. Gen Virology 69, 2179–2188 (1988).
Asada, H., Tamura, M., Kondo, K., Okano, Y., Takahashi, Y., Dohi, T., Nagai, T., Kurata, T., and Yamanishi, K., J. Gen. Virology 68, 1961–1969 (1987).
Avery, R.J., and J. Niven., Infect. and Immun. 26, 795–801 (1979).
Azad, A.A., S.A. Barrett, and K.J. Fahey, Virology 143, 35–44 (1985).

(List continued on next page.)

*Primary Examiner*—Mary E. Mosher
*Attorney, Agent, or Firm*—Frommer Lawrence & Haug LLP; William S. Frommer; Thomas J. Kowalski

[57] ABSTRACT

Attenuated recombinant viruses containing DNA coding for a canine distemper virus antigen, as well as methods and compositions employing the viruses, are disclosed and claimed. The recombinant viruses can be NYVAC or ALVAC recombinant viruses. The DNA can code for at least one of: canine distemper virus fusion protein and canine distemper virus hemagglutinin glycoprotein. The recombinant viruses and gene products therefrom are useful for eliciting protection against canine distemper virus.

16 Claims, 42 Drawing Sheets

OTHER PUBLICATIONS

Azad, A.A., S.A. Barrett, K.J. Fahey, and P. Hudson, Virology 149, 190–198 (1986).

Azad, A.A., M.N. Jagadish, M.A. Brown, and P. Hudson, Virology 161, 145–152 (1987).

Azad et al. Vaccines 90, pp. 59–62 Cold Spring Harbor Laboratory Press, CSH, NY, 1990.

Baer, R., Bankie, A.T., Biggin, M.D., Deiniger, P.L., Farrel, P.J., Gibson, T.J., Hatfull, G., Hudsson, G.S., Satchwell, S.C., Seguin, C., Tuffnell, P.S., Barrell, B.G., Nature 310, 207–211 (1984).

Baker, J.A., B.E. Sheffy, D.S. Robson, J. Gilmartin, Cornell Vet (USA) 56, 588–594 (1966).

Balachandran, N., Bacchetti, S. and Rawls, W., Infec. Immun. 37, 1132–1137 (1982).

Barrett, T., Clarke, D.K., Evans, S.A., and Rima, B.K., Virus Research 8, 373–386 (1987).

Baroudy, B.M., Venkatesan, S., and B. Moss, Cell 28, 315–324 (1982).

Baxby, D. In Jenner's Smallpox Vaccine, (Heinemann Educational Books, Ltd., London) 214 (1981).

Baxby, D., Paoletti, E., Vaccine 10, 8–9 (1992).

Beard, C.W., Avian Diseases 23, 327–334 (1979).

Beard, C.W., and R.P. Hanson, In Disease of poultry, 8th edition, ed. M.S. Hofstad, (Iowa State University Press, Ames, Iowa) pp. 452–470 (1984).

Baxby, D., Paoletti, E., Vaccine 10, 8–9 (1992).

Becht, H., H. Muller, and H.K. Muller, J. Gen Virol. 69, 631–640 (1988).

Beck, E., Ludwig, G., Auerswald, E.A., Reiss, B., and Schaller, H., Gene 19, 327–336 (1982).

Behbehani, A.M., Microbiological Reviews 47, 455–509 (1983).

Ben–Porat, T., F.J. Rixon, and M.L. Blankenship, Virology 95, 285–294 (1979).

Ben–Porat, T. In Organization and replication of viral DNA, ed. A.S. Kaplan, (CRC Press, Inc., Boca Raton, Florida) pp. 147–172 (1982).

Ben–Porat, T. and A.S. Kaplan, Virology 41, 265–273 (1970).

Ben–Porat, T., J. DeMarchi, J. Pendrys, R.A. Veach, and A.S. Kaplan, J. Virol. 57, 191–196 (1986).

Ben–Porat, T. and A.S. Kaplan, In the Herpesviruses, vol. 3, ed. B. Roizman, (Plenum Publishing Corp., York) pp. 105–173 (1985).

Bergoin, M., and Dales, S., In Comparative Virology, eds. K. Maramorosch and E. Kurstak, (Academic Press NY) pp. 169–205 (1971).

Bertholet, C., Drillien, R., and Wittek, R., Proc. Natl. Acad. Sci. USA 82, 2096–2100 (1985).

Bestetti, G., R. Fatzer, and R. Frankhauser, Acta Neuropathol. 43, 69–75 (1978).

Black, F.L., L.L. Berman, M. Libel, C.A. Reichelt, F. de P. Pinheiro, A.T. da Rosa, F. Figuera, and E.S. Gonzales.

Borysiewicz, L.K., J.K. Hickling, S. Graham, J. Sinclari, M.P. Crange, G.L. Smith, and J.G. Sissons, J. Exp. Med. 168, 919–931 (1988).

Boursnell, M.E.G., I.J. Foulds, J.I. Campbell and M.M. Binns, J. Gen. Virol. 69, 2995–3003 (1988).

Boursnell, M.E.G., Green, P.F., Campell, J.I.A., Deuter, A., Peters, R.W., Tomley, F.M., Samson, A.C.R., Chambers, P., Emmerson, P.T., and Binns, M.M. J. Gen. Virol. 71, 621–628 (1990a).

Boursnell, M.E.G., Green, P.F., Campbell, J.I.A., Deuter, A., Peters, R.W., Tomley, F.M., Samson, A.C.R., Emmerson, P.T., and Binns, M.M. Vet. Microbiol. 23, 305–316 (1990b).

Boursnell, M.E.G., Green, P.F., Samson, A.C.R., Campell, J.I.A., Deuter, A., Peters, R.W., Millar, N.S., Emmerson, P.T., and Binns, M.M. Virology 178, 297–300 (1990c).

Boyle, D.B. and B.E.H. Coupar, Gene 65, 123–128 (1988).

Brandt, W.E., J. Infect Dis. 157, 1105–1111 (1988).

Brochier, B., Kieny, M.P., Costy, F., et al., Nature 354 pp. 520–522 (1991).

Bryson, Y., Dillon, M., Lovett, M., Acuna, G., Taylor, S., Cherry, J., Johnson, B., Wiesmeier, E., Growdon, W., Creagh–Kirk, T. and Keeney, R., N. Eng. J. Med. 308, 916–921 (1983).

Bucher, D., Poppolo, S., Baer, M., Mikhail, A., Gong, Y–F., Whitaker, C., Paoletti, E., and Judd, A., J. Virol. 63, 3622–3633 (1989). Flu.

Buller, R.M.L., and Palumbo, G.J., Microbiol. Rev. 55, 80–122 (1991).

Buller, R.M.L., G.L. Smith, Cremer, K., Notkins, A.L., and Moss, B., Nature 317, 813–815 (1985).

Buller, R.M.L., Chakrabarti, S., Cooper, J.A., Twardzik, D.R., and Moss, B., J. Virol. 62, 866–874 (1988).

Bunn, T.O., In: Rabies, eds. Campbel, J.B. and Charlton K.M. (Kluwer Academy Press, Boston) pp. 474–491 (1988). vet vaccines, rabies.

Burkhardt, E., and H. Muller, Archives of Virology 94, 297–303 (1987).

Bush, M., R.J. Montali, D. Brownstein, A.E. James, Jr. and M.J.G. Appel, J. Am. Vet. Med. Assoc. 169, 959–960 (1976).

Cantin, E., Eberle, R., Baldrick, J., Moss, B., Willey, D., Notkins, A. and Openshaw, H., Proc. Natl. Acad. Sci. USA, 84, 5908–5912 (1987). VV–HSVgB.

Carpenter, J.W., M.J.G. Appel, R.C. Erickson, and M.N. Novilla, J. Am. Vet. Med. Assoc. 169, 961–964 (1976).

Chakrabarti, S., Brechling, K., and Moss, B., Mol. Cell. Biol. 5, 3403–3409 (1985).

Chakrabarti, S., Robert–Guroff, M., Wong–Staal, F., Gallo, R.C., and Moss, B. Nature 320, 535–537 (1986).

Chambers, P., N.S. Millar, and P.T. Emmerson, J. Gen. Virol. 67, 2685–2694 (1986).

Chambers, T.J., Hahn, C.S., Galler, R., and Rice, C.M., Ann. Rev. Microbiol. 44, 649–688 (1990).

Chambers, T.M., Y. Kawoka, and R.G. Webster, Virology 167, 414–421 (1988).

Chan, W., Immunol. 49, 343–352 (1983).

Charles, I.G., Rodgers, B.C., Makoff, A.J., Charfield, S.N., Slater, D.E., and Fairweather, N.F., Infect. Immum. 59, 1627–1632 (1991).

Chen, C., R.W. Coupans, and P.W. Choppin, J. Gen. Virol. 11, 53–58 (1971).

Cheng, K–C, G. L. Smith and B. Moss, J. Virol. 60, 337–344 (1986).

Child, S.J., Palumbo, G.J., Buller, R.M.L., and Hruby, D.E. Virology 174, 625–629 (1990).

Chirgwin, J.M., Przybyla, A.E., MacDonald, R.J., and Rutter, W.J. Biochemistry. 18, 5294–5299 (1979).

Chisari, F.V., P. Filippi, A. McLachlan, D.R. Milich, M. Riggs, S. Lee, R.R. Palmiter, C.A. Pinkert and R.L. Brinster, J. Virol. 60, 880–887 (1986).

Choppin, P.W., C.D. Richardson, D.C. Merz, W.W. Hall, and A. Scheid, J. Infect. Dis. 143, 352–363 (1981).

Clewell, D.B., J. Bacteriol 110, 667–676 (1972).

Cianciolo, G.J., Copeland, T.D., Oroszlan, S., and Snyderman, R. Science 230, 453–455 (1985).

Clarke, B.E., S.E. Newton, A.R. Carroll, M.J. Francis, G. Appleyard, A.D. Syred, P.E. Highfield, D.J. Rowlands and F. Brown, Nature 330, 381–384 (1987).

Clewell, D.B. and D.R. Helinski, Proc. Natl. Acad. Sci. USA 62, 1159–1166 (1969).

Colinas, R.J., R.C. Condit and E. Paoletti, Virus Research 18, 49–70 (1990).

Collins, P.L., Purcell, R.H., LOndon, W.T. et al., Vaccine 8, 154–168 (1990).

Cooney E.L., Corrier A.C., Greenberg P.D., et al., Lancet 337, 567–572 (1991).

Cox, J.H., B. Dietzschold, and L.G. Schneider, Infect. Immun. 16, 754–759 (1977).

Dales, S., Ann. Rev. Microbiol 44, 173–192 (1990).

Daniels, R.S., Skehel, J.J., and Wiley, D.C., J. Gen. Virol. 66, 457–464 (1985).

Dantas, J.R., Fr., Okuno, Y., Asada, H., Tamura, M., Takahashi, M., Tanishita, Ol, Takahashi, Y. Kurata, T., and Yamanishi, K., Virology 151, 379–384 (1986).

Davis, W., Taylor, J. and Oakes, J., J. Infect. Dis. 140, 534–540 (1979).

De, B.K., Shaw, P.A. Rota, M.W. Harmon, J.J. Esposito, R. Rott, N.J. Cox and A.P. Kendal, Vaccine 6, 257–261 (1988).

DeLay, P.D., S.S. Stone, D.T. Karzon, S. Katz, and J. Enders, Am. J. Vet. Res. 26, 1359–1373 (1965).

Delpeyroux, F., N. Peillon, B. Blondel, R. Crainic and R.E. Streeck, J. Virol., 62, 1836–1839 (1988).

Derosiers, R.C., M.S. Wyand, T. Kodama, T.J. Ringler, L.O. Arthur, P.K. Sehgal, N.L. Letvin, N.W. King and M.D. Daniel, Proc. Natl. Acad. Sci. USA 86, 6353–6357 (1989).

Diallo, A., Vet. Micro. 23, 155–163 (1990).

Dobos, P.J., Virol. 32, 1046–1050 (1979).

Dobos, P.J., B.J. Hill, R. Hallett, D.T. Kells, H. Becht, and D. Teninges, J. Virol. 32, 593–605 (1979).

Douglas, J., Critchlow, C., Benedetti, J., Mertz, G., Connor, J., Hintz, M., Fahnlander, A., Remington, M., Winter, C. and Corey, L., N. Engl. J. Med. 310, 1551–1556 (1984).

Dowbenko, D. and Lasky, L., J. Virol. 52, 154–163 (1984).

Dowling, P.C., B.M. Blumberg, J. Menonna, J.E. Adamus, P. Cook, J.C. Crowley, D. Kolakofsky, and S.D. Cook, J. Gen. Virol. 67, 1987–1992 (1986).

Dreyfuss, G., Adam, S.A., and Choi, Y.D., Mol. Cell. Biol. 4, 415–423 (1984).

Drillien, R., F. Koehren and A. Kirn, Virology 111, 488–499 (1981).

Drillien, R., Spehner, D., and A. Kirn, J. Virol. 28, 843–850 (1978).

Drillien, R., D. Spehner, A. Kirn, P. Giraudon, R. Buckland, F. Wild, and J.P. Lecocq, Proc. Natl. Acad. Sci. USA 85, 1252–1256 (1988).

Duncan, R., E. Nagy, P.J. Krell and P. Dobos, J. Virol. 61, 3655–3664. (1987).

Easterday, B.C. and V.S. Hinshaw, In Diseases of Poultry, Ninth edition, eds. B.W. Calnek, H.J. Barnes, et al., (Iowa State University Press, Ames, Iowa) pp. 531–551 (1991).

Eble, B.E., V.R. Lingappa and D. Ganem, Mol. Cell. Biol. 6, 1454–1463 (1986).

Edbauer, C., R. Weinberg, J. Taylor, A. Rey-Senelonge, J.F. Bouquet, P. Desmettre, and E. Paoletti, Virology 179, 901–904 (1990).

Eisel, U., Jarausch, W., Goretzki, K., Henschen, A., Engles, J., Weller, U., Hudel, M., Habermann, E., and Niemann, H. EMBO J. 5, 2495–2502 (1986).

Elder, J.H., McGee, J.S. Munson, M., Houghton, R.A., Kloetzer, W., Bittle, J.L., and Grant, C.K., J. Virol. 61, 8–15 (1987).

Elder, J.H. and Mullins, J.V., J. Virol. 46, 871–880 (1983).

Elliot et al., J. Gen. Virol. (1991), 72, 1762–1779.

Engelke, D.R., Hoener, P.A., and Collins, F.S., Proc. Natl. Acad. Sci. USA 85, 544–548 (1988).

Espion, D., De Henau, S., Letellier, C., Wemers, C.-D., Brasseur, R., Young, J.F., Gross, M., Rosenberg, M., Meulemans, G. and Burny, A. Arch. Virol. 95, 79–95 (1987).

Esposito, J.J., K. Brechling, G. Baer and B. Moss, Virus Genes 1, 7–21 (1987).

Esposito, J.J., J.C. Knight, J.H. Schaddock, F.J. Novembre and G. Baer, Virology 165, 313–316 (1988).

Etinger H.M., Altenburger W., Vaccine 9, 470–472 (1991).

Fahey, K.J., I.J. O'Donnell, and A.A. Azad, J. Gen. Virol. 66, 1479–1488 (1985a).

Fahey, K.J., I.J. O'Donnell, and T.J. Bagust, J. Gen. Virol. 66, 2693–2702 (1985b).

Fahey, K.J., K. Erny and J. Crooks, J. Gen. Virol. 70, 1473–1481 (1989).

Fairweather, N.F., and Lyness, V.A. Nucleic Acids Res. 14, 7809–7812 (1986).

Falgout, B., Chanock, R. and Lai, C.-J, J. Virology 63, 1852–1860 (1989).

Falkner, F.G. and B. Moss, J. Virol. 62, 1849–1854 (1988).

Falkner, F.G. and B. Moss, J. Virol. 64, 3108–3111 (1990).

Fenner, F., and J.F. Sambrook, Virology 28, 600–609 (1966).

Fenner, F., P.A. Bachmann, E.P.J. Gibbs, F.A. Murphy, M.J. Studdert, and D.O. White, In Veterinary Virology, ed. F. Fenner, (Academic Press, Inc., New York) pp. 488–503 (1987).

Finklestein et al. Trends in Biotech 7, pp. 273–277 (1989).

Flexner, C., Hugen, A., and Moss, B., Nature 330, 259–262 (1987).

Franchini, G., Fargnoli, K.A., Giomnini, F., Jagodzinski, L., DeRossi, A., Bosch, M., Biberfield, G., Fenyo, E.M., Albert, J., Gallo, R.C., and Wong-Staal, F., Proc. Natl. Acad. Sci. USA 86, 2433–2437 (1989).

Franchini, G., Gurgo, C., Guo, H.–G., Gallo, R.C., Collati, E., Fargnoli, K.A., Hall, L.F., Wong-Staal, F., and Reitz, Jr., M.S., Nature (London) 328, 539–543 (1987).

Franke, C.A., Rice, C.M., Strauss, J.H., and D.E. Hruby, Mol. Cell. Biol. 5, 1918–1924 (1985).

Fujisaki, Yl, Sugimore, T., Morimoto, R., Muira, Y., Kawakani, Y. and Nakano, K., Natl. Inst. Anim. Health Q. 15, 55–60 (1975b).

Funahashi, S., T. Sato and H. Shida, J. Gen. Virol. 69, 35–47 (1988).

Galibert, F., E. Mandart, F, Fitoussi, P. Tiollais and P. Charnay, Nature 281, 646–650 (1979).

Gangemi, J.D., and D.G. Sharp, Virology 85, 262–270 (1978).

Garten, W., Kohama, T., and H–D. Klenk. J. Gen. Virol. 51, 207–211 (1980).

Giavedoni, L., Jones, L., Mebus, C., and Yilma, T.A., Proc. Natl. Acad. Sci. USA 88, 8011–8015 (1991).

Gibson, C.A., Schlesinger, J.J., and Barrett, A.D.T., Vaccine 6, 7–9 (1988).

Gillard, S., Spehner, D., and R. Drillien, J. Virol. 53, 316–318 (1985).

Gillard, S., Spehner, D., Drillien, R., and Kirn, A., Proc. Natl. Acad. Sci. USA 83, 5573–5577 (1986).

Gillespie, J.H., and D.T. Karzon, Proc. Soc. Exp. Biol Med. 105, 547–551 (1960).

Giraudon, P., Ch. Gerald and T.F. Wild, Intervirology 21, 110–120 (1984).

Glosser, J.W., Environmental assessment and preliminary finding of NO significant impact. Veterinary biologics authorized field trial of an experimental biologic: The Wistar Institute of Anatomy and Biology proposed field trial of a live experimental vaccinia vectored rabies vaccine. United Stated Department of Argiculture, Animal, and Plant Health Inspection Services (1989).

Goebel, S.J., Johnson, G.P., Perkus, M.E., Davis, S.W., Winslow, J.P., Paoletti, E., Virology 179, 247–266 (1990a).

Goebel, S.J., G.P. Johnson, M.E. Perkus, S.W. Davis, J.P. Winslow and E. Paoletti, Virology 179, 517–563 (1990b).

Goldstein, D.J. and S.K. Weller, Virology 166, 41–51 (1988).

Gonczol, E., Furlini, G., Ianacone, J., and Poltkin, S.A., J. Virol. 14, 37–41 (1986).

Gonczol, E., C. De Taisne, G. Hirda, K. Berensci, W. Lin, E. Paoletti, and S. Plotkin, Vaccine 9, 631–637 (1991).

Gould, E.A., Buckley, A., Barrett, A.D.T., and Cammack, N., J. Gen. Virol. 67, 591–595 (1986).

Graham, F.L. and A.J. Van der Eb, Virology 54, 536–539 (1973).

Graves, M.C., S.M. Silver, and P.W. Choppin, Virology 86, 254–263 (1978).

Gretch, D.R., B. Kari, L. Rasmussen, R.C. Gehrz, and M.F. Stinski, J. Virol. 62, 875–881 (1988).

Gubler, U., and Hoffman, B.J., Gene 25, 263–269 (1983).

Guilhot, S., Hampe, A., D'Auriol, L., and Gailbert, F. Virology 161, 252–258 (1987).

Guo, P., Goebel, S., Davis, S., Perkus, M.E., Languet, B., Desmettre, P., Allen, G., and Paoletti, E., J. Virol. 63, 4189–4198 (1989).

Guo, P., S. Goebel, S. Davis, M.E. Perkus, J. Taylor, E. Norton, G. Allen, B. Languet, P. Desmettre, and E. Paoletti, J. Virol. 64, 2399–2406 (1990).

Gupta, R.K., Misra, C.N., Gupta, V.K., and Saxena, S.N., Vaccine 9, 865–867 (1991).

Gurgo, C., Guo, H.–G., Franchini, G., Aldovini, A., Collalti, E., Farrell, K., Wong-Staal, F., Gallo, R.C., and Reitz, M.S., Jr., Virology 164, 531 (1988).

Haffar, O., Garrigues, J., Travis, B., Moran, P., Zarling, J. and Hu, S.–L, J. Virol. 64, 2653–2659, (1990).

Hall, W.W., R.A. Lamb, and P.W. Choppin, Virology 100, 433–449 (1980).

Hampl, H., Ben–Porat, T., Ehrlicher, L., Habermehl, K.,–O., and Kaplan, A.S., J. Virol. 52, 583–590 (1984).

Hardy, Jr. W.D., Hess, P.W., MacEven, E.G., McCelland, A.J., Zuckerman, E.E., Essex, M., Cotter, S.M., Jarrett, Ol, Cancer Res. 36 582–588 (1976).

Hartley, W.J., Vet. Path. 11, 301–312 (1974).

Heermann, K.H., U. Goldmann, W. Schwartz, T. Seyffarth, H. Baumgarten and W.H. Gerlich, J. Virol. 52, 396–402 (1984).

Henchal, E.A., Henchal, L.S., and Schlesinger, J.J., J. Gen. Virol. 69, 2101–2107 (1988).

Hinshaw, V.S., Naeve, C.W., Webster, R.G., Douglas, A., Dkehel, J.J., and Bryans, J.T., Bull. World Health Organization 61, 153–158 (1983).

Hinshaw, V.S., R.G. Webster, W.J. Bean, G. Sriram, Comp. Immunol. Microbiol. Infect. Dis. 3, 155–164 (1981).

Hoffar, O., Garrigues, J., Travis, B., Moran, P., Zarling, J. and Hu, S.–L., J. Virol. 64, 2653–2659, (1990).

Homma, M., and M. Ohuchi, J. Virol. 12, 1457–1465 (1973).

Hoshikawa, N., Kojima, A., Yasuda, A., Takayashiki, E., Masuko, S., Chiba, J., Sata, T., and Kurata, T., J. Gen. Virol. 72 2509–2517 (1991).

Hosmalin, A., Nara, P.L. Zweig, M., Lerche, N.W. Cease, K.B., Gard, E.A., Markham, P.D., Putnery, S.D., Daniel, M.D., Desrosiers, R.C., and Berzofsky, J.A. J. Immuol. 146, 1667–1673 (1991).

Hruby, D.E. and L.A. Ball, J. Virol. 43, 403–409 (1982).

Hruby, D.E., R.A. Maki, D.B. Miller and L.A. Ball, Proc. Natl. Acad. Sci. USA 80, 3411–3415 (1983).

Hruby, D.E., Lynn, D.L., Condit, R., and J.R. Kates, J. Gen. Virol 47, 485–488 (1980).

Hu, et al., Proc. Natl. Acad. Sci. USA 86, 7213–7217 (1989).

Hu, S.–L., Travis, B.M., Garrigues, J., Zarling, J.M., Eichberg, J.W. and Alpers, C.E., In Vaccine 90, eds. Chanock, R.M., Lerner, R.A., Brown, F., and Ginsberg, H., (Cold Spring Harbor Press, Cold Spring Harbor, New York) pp. 231–236 (1990).

Hu, S.–L., Travis, B.M., Garrigues, J., Zarling, J.M., Sridhar, P., Dykers, T., Eichberg, J.W., and Alpers, C. Virology 179, 321–329 (1990).

Hu, S.–L., Fultz, P., McClure, H., Eichberg, J., Thomas, E., Zarling, J., Singhal, M., Kosowski, S., Swenson, R., Anderson, D. and Todaro, G., Nature 328, 721–723 (1987).

Hu, S.–L., Kosowski, S. and Dalrymple, J., Nature 320, 535–537, (1986).

Huang, C.H., Advances in Virus Research 27, 71–101 (1982).

Hudson, P.J., N.M. McKern, B.E. Power, and A.A. Azad, Nucl. Acids. Res. 14, 5001–5012 (1986).

Hunt, L.A., D.W. Brown, H.L. Robinson, C.W. Naeve, and R.G. Webster, J. Virol. 62, 3014–3019 (1988).

Ichihashi, Y. and Dales, S., Virology 46, 533–543 (1971).

Igarashi A., J. Gen. Virol. 40, 531–544 (1978).

Imagawa, D.T., P. Goret, and J.M. Adams, Proc. Natl. Acad. Sci. USA 46, 1119–1123 (1960).

Inoue Y.K., Bull. WHO 30, 181–185 (1964).

Isle et al., Virology 112, 306–317 (1981).

Itamura, S., H. Iinuma, H. Shida, Y. Morikawa, K. Nerome and A. Oya, J. Gen. Virol. 71, 2859–2865 (1990).

Itoh, Y., E. Takai, H. Ohnuma, K. Kitajima, F. Tsuda, A. Machida, S. Mishiro, T. Nakamura, Y. Mikyakawa and M. Mayumi, Proc. Natl. Acad. Sci. USA 83, 9174–9178 (1986).

Jackwood, D.J., Y. M. Saif, and J.H. Hughes, Avain Dis. 28, 990–1006 (1984).

Jacobson, J.G., D.A. Leib, D.J. Goldstein, C.L. Bogard, P.A. Schaffer, S.K. Weller and D.M. Coen, Virology 173, 276–283 (1989).

Jagadish, N.M, V.J. Staton, P.J. Hudson, and A.A. Azad, J. Virol. 62, 1084–1087 (1988).

Jahn, G., B–C. Scholl, B. Troupe, and B. Fleckenstein. J. Gen Virol. 68, 1327–1337 (1987).

Jamieson, A.T., G.A. Gentry and J.H. Subak-Sharpe, J. Gen. Virol. 24, 465–480 (1974).

Jarrett, O., and Russell, P.H., Int. J. Cancer 27, 466–472 (1978).

Jarrett, O., Hardy, Jr., W.D., Golder, M.C., and Hay, D., Int. J. Cancer 21, 334–337 (1978).

Jarrett, O., Laird, H.M., and Hay, D., J. Gen. Virol. 20, 169–175 (1973).

Javeherian, K., Langlois, A. J., McDanal, C., Ross, K. L., Eckler, L. I., Jellib, C. L., Profy, A. T., Rusche, J. R., Bolognesi, D. P., Putney, S. D., and Mathews, T. J., Proc. Natl. Acad. Sci. USA 86, 6768–6772 (1989).

Jilg, W., C. Delhoune, F. Deinhardt, A.J. Roumeliot-ou–Karayannis, G.J. Papaevangelou, I.K. Mushahwar and L.R. Overby, J. Med. Virol. 13, 171–178 (1984).

Jin, H. and Elliott, R.M., J. Virology 65, 4182–4189 (1991).

Joklik, W.K., Pickup, D.J., Patel, D.D., and Moody, M.D., Vaccine 6, 123–128 (1988).

Karacostas, V., Nagashima, K., Gonda, M. A., and Moss, B., Proc. Natl. Adad. Sci. USA 86, 8964–8968 (1989).

Kari, B., N. Lussenhop, R. Goertz, M. Wabuke–Bunoti, R. Radeke, and R. Gehrz, J. Virol. 60, 345–352 (1986).

Karzon, D.T., Pediatrics 16, 809–818 (1955).

Karzon, D.T., Annals of the N.Y. Academy of Sci. 101, 527–539 (1962).

Kaplan, J.M., Mardon, G., Bishop, J.M., and H.E. Varmus, Mol. Cell. Biol. 8, 2435–2441 (1988).

Kato, S., M. Takahashi, S. Kameyama and J. Kamahora, Biken's 2, 353–363 (1959).

Kaufer, I. and E. Weiss, Infect. Immun. 27, 364–367 (1980).

Kaufman, B.M., Summers, P.L., Dubois, D.R., and Eckels, K.H., Am. J Trop. Med. Hyg. 36, 427–434 (1987).

Kaufman, B. M., Summers, P. L., Dubois, D. R., Cohen, W. H., Gentry, M. L., Timchak, R. L., Burke, D. S. and Eckels, K. H., Am. J. Trop. Med. Hyg. 41, 576–580 (1989).

Kawaoka, Y., Bean, W.J., Webster, R.G., Virology 169, 283–292 (1989).

Kazacos, K.R., H.L. Thacker, H.L. Shivaprasad, and P.P. Burger, J. Am. Vet. Med. Assoc. 179, 1166–1169 (1981).

Keegan, K. and Collett, M.S., J. Virology 58, 263–270 (1986).

Kensil, C.R., Barrett, M.S., Kushner, B.S., Beltz, G., Storey, J., Patel, U., Recchia, J., Aubert, A., Marciani, D., JAVMA 199, 1402–1405 (1991).

Kibenge, F.S.B., A.S. Dhillon, and R.G. Russell, J. Gen. Virol. 69, 1757–1775 (1988).

Kieff, E., and Liebowitz, D., In Virology, Second Edition, eds. B. N. Fields, D. M. Knipe et al., (Raven Press) 1990).

Kieny, M. P., Lathe, R., Drillien, R., Spehner, D., Skory, S., Schmitt, D., Wiktor, T., Koprowski, H., Lecocq, J. P., Nature (London) 312, 163–166 (1984).

Killington, R.A., J. Yeo, R.W. Honess, D.H. Watson, B.E. Duncan, I.W. Halliburton, and J. Mumford, J. gen. Virol. 37, 297–310 (1977).

Kimura–Kuroda, J., and Yasui, K., Immunol. 141, 3606–3610 (1988).

Kingsbury, D.W., M.A. Bratt, P.W. Choppin, R.P. Hanson, T. Hosaka, Y. ter Meulen, E. Norrby, W. Plowright, R. Rott and W.H. Wunner, Intervirology 10, 137–152 (1978).

Kingsbury, D.W., In Virology, Second Edition, eds. B.N. Fields, D.M. Knipe et al., (Raven Press, Ltd. New York) pp. 1075–1089 (1990).

Kingsford, L., Ishizawa, L.D., and Hill, D.W., Virology 129, 443–445 (1983).

Klasse, P.J., Pipkorn, R., and Blomberg, J., Proc. Natl. Acad. Sci. USA 85, 5225–5229 (1988).

Kleitmann W., Schottle A., Kleitmann B., et al., In Cell Culture Rabies Vaccines and Their Protective Effect in Man., ed. Kuwert/Wiktor/Koprowski, (International Green Cross—Geneva) pp. 330–337 (1981).

Knauf, V.C., and Nester, E.W., Plasmid 8, 45–54 (1982).

Kodama, T., Wooley, D. P., Naidu, Y. M., Kestler III, H. W., Daniel, M. D., Li, Y. and Derosiers, R. C. J. Virol. 63, 4709–4714 (1989).

Koff, W.C. and Fauci, A.S., AIDS 1, S125–S129 (1989).

Konishi, E., Pincus, S., Fonseca, B.A.L., Shope, R.E., Paoletti, E., and Mason, P.W., Virology 185, 401–410 (1991).

Konno J., Endo K., Agatsuma H., and Ishida N. Cyclic, Am. J. Epidemiol. 84, 292–300 (1966).

Kost, T.A., E.V. Jones, K.M. Smith, A.P Reed, A.L. Brown, and T.J. Miller, Virology 171, 365–376 (1989).

Kotwal, G.J. and Moss, B., Nature (Lond.) 335, 176–178 (1988).

Kotwal, G.J., A.W. Hugin and B. Moss, Virology 171, 579–587 (1989a).

Kotwal, G.J. and B. Moss, J. Virol. 63, 600–606 (1989b).

Kotwal, G.J., S.N. Isaacs, R. McKenzie, M.M. Frank and B. Moss, Science 250, 827–830 (1990).

Koup, R. A., Sullivan, J. L., Levine, P. H., Brettler, D., Mahr, A., Mazzara, G., McKenzie, S., and Panicali, D. Blood 73, 1909–1919 (1989).

Kunkel, T.A., Roberts, J.D., and Zakour, R.A., Method in Enzym. 154, 367–382 (1987).

Kunkel, T.A., Proc. Natl. Acad. Sci. USA 82, 488–492 (1985).

Kuroda, K., C. Hauser, R. Rott, H.–D. Klenk, and W. Doerfler, EMBO 5, 1359–1365 (1986).

Kuroki, K., R. Russnak and D. Ganem, Mol. Cell. Biol. 9, 4459–4466 (1989).

Laemmli, U.K., Nature (London) 227, 680–685 (1970).

Lai, A. C.–K. and B. G.–T. Pogo, Virus Res. 12, 239–250 (1989).

Lane, J. M., Rueben, F. L., Neff, J. M., and Miller, J. D., New Eng. J. Med. 281, 1201–1208 (1969).

Lathe, R., M.P. Kieny, D. Schmitt, P. Curtis and J.P. Lecocq, J. Mol. Appl. Gen. 2, 331–342 (1984).

Le, L., Brasseur, R., Wemers, C., Meulemans, G., and Burny, A. Virus Genes 1, 333–350 (1988).

Lecocq, J.P., M.P. Kieny, Y. Lemoine, R. Drillien, T. Wiktor, H. Koprowski and R. Lathe, In World's Debt to Pasteur, eds. Koprowski, H. and Plotkin, S.A., (Alan R. Liss, New York), 259–271 (1985).

Lecocq, J.P., M. Zukowski and R. Lathe, In Methods in Virology, eds. Maramorosch, K. and Koprowski, H., (Academic Press, New York) vol. VII, 124–172 (1984).

Lennon, J.L., and F.L. Black, J. Ped. 108, 671–676 (1986).

Lukacs, N., Theil, H.–J., Mettenleiter, T.C., and Rziha, H.–J., J. Virol. 53, 166–172 (1985).

Macfarlan, R.I., B. Dietzschold, and H. Koprowski, J. Mol Imunol. 23, 733–741 (1986).

Mandecki, W., Proc. Natl. Acad. Sci. USA 83, 7177–7182 (1986).

Maniatis, T., Fritsch, E.F., and Sambrook, J. In Molecular cloning: a laboratory manual, (Cold Spring Harbor Laboratory, Cold Spring Harbor, NY) (1982).

Marsden, H., Stow, N., Preston, V., Timbury, M. and Wilkie, N., J. Virol. 28, 624–642 (1978).

Marsden, H., Buckmaster, A., Palfreyman, J., Hope, R. and Minson, A., J. Virol. 50, 547–554 (1984).

Mason, P.W., Dalrymple, J.M., Gentry, M.K., McCown, J.M., Hoke, C.H., Burke, D.S., Fournier, M.J., and Mason, T.L., J Gen. Virol. 70, 2037–2049 (1989).

Mason, P. W., McAda, P. C., Dalrymple, J.M., Fournier, M.J., and Mason, T. L., Virology 158, 361–372 (1987a).

Mason, P.W., McAda, P.W., Mason, T.L., and Fournier, M.J., Virol. 161, 262–267 (1987b).

Mason, P.W., Pincus, S., Fournier, M.J., Mason, T.L., Shope, R.E., and Paoletti, E., Virol. 180, 294–305 (1991).

Mason P.W., Virology 169, 354–364 (1989).

Matthews, R.E.F., Intervirology 17, 104–105 (1982a).

McAda, P. C., Mason, P. W., Schmaljohn, C.S., Dalrymple, J. M., Mason, T. L. and Fournier, M. J. Virology 158, 348–360 (1987).

McGeoch, D., Moss, H., McNab, D. and Frame, M., J. Gen. Virol. 68, 19–38 (1987).

McGinnes, L.W. and Morrison, T.G. Virus Res. 5, 343–356 (1986).

McLachlan, A., D.R. Milich, A.K. Raney, M.G. Riggs, J.L. Hughes, J. Sorge and F.V. Chisari, J. Virol. 61, 683–692 (1987).

McLaughlin–Taylor, E., Willey, D., Cantin, E., Eberle, R., Moss, B. and Openshaw H., J. Gen. Virol. 69, 1731–1734 (1988).

Meignier, B., Jourdier, T., Norrild, B., Pereira, L. and Roizman, B., J. Infect. Dis. 155, 921–930 (1987).

Merz, D.C., A. Scheid, and P. Choppin, J. Exper. Med. 151, 275–288 (1980).

Mettenleiter, T.C., N. Lukacs, H.–J. Thiel, C. Shreurs, and H.–J. Rziha, Virology 152, 66–75 (1986).

Mettenleiter, T.C., N. Lukacs, and H.–J. Rziha, J. Virol. 53, 52–57 (1985).

Meulemans, G., C. Letellier, M. Gronze, M.C Carlier, and A Burney, Avian Pathol. 17, 821–827 (1988).

Michel, F., Hoffenbach, A., Langlade–Demoyen, P., Guy, B., Lecocq, J.–P., Wain–Hobson, S., Kieny, M.–P. and Plata, F., Eur. J. Immunology 18, 1917 (1988).

Milich, D.R. and A. McLachlan, In Viral Hepatitis and Liver Disease, pp. 645–649 (1988).

Milich, D.R., A. McLachlan, A. Moriarty and G.B. Thornton, J. Immun. 138, 4456–4465 (1987a).

Milich, D.R., A. McLachlan, G.B. Thornton and J.L. Hughes, Nature 329, 547–549 (1987b).

Miller, G., In Virology, Second Edition, eds. B.N. Fields, D.M. Knipe et al. (Raven Press) (1990).

Monath, T.P., In the Togaviridae and Flaviviridae, eds. S. Schlesinger and M.J. Schlesinger, (Plenum Press, New York/London) pp. 375–440 (1986).

Morgan, A.J., M. Mackett, S. Finerty, J.R. Arrand, F.T. Scullion and M.A. Epstein, J. Med. Virol. 25, 189–195 (1988).

Morgan, J.R. and B.E. Roberts, J. Virol. 51, 283–297 (1984).

Moss et al., Science 252, 1662–1667 (1991).

Moss, B., E. Winters and J. A. Cooper, J. Virol. 40, 387–395 (1981).

Moura, R.A., and J. Warren, J. Bact. 82, 702–705 (1961).

Murphy, B.R. and R.G. Webster, In Virology, Second Edition, eds. B.N. Fields, D.M. Knipe et al., (Raven Press, Ltd., New York) pp. 1091–1152 (1990).

Murphy–Corb, M., Martin, L.N., Davison–Fairburn, B., Montelaro, R.C., Miller, M., West, M., Ohkawa, S., Baskin, G.B., Zhang, J.–Y., Putney, S.D., Allison, A.C. and Eppstein, D.A., Science 246, 1293–1297 (1989).

Murray, K., S.A. Bruce, A. Hinnen, P. Wingfield, P.M.C.A. van Erd, A. de Reus and H. Schellekens, EMBO 3, 645–650 (1984).

Nagai, Y., T. Yoshida, M. Hamaguchi, H. Naruse, M. Iinuma, K. Maeno, and T. Matsumoto, Microbiol. Immunol. 24, 173–177 (1980).

Nagai, Y., H.D. Klenk, and R. Rott, Virology 72, 494–508 (1976).

Neurath, A.R., S.B.H. Kent, N. Strick and K. Parker, Cell 46, 429–436 (1986).

Neurath, A.R. and S.B.H. Kent, Adv. Vir. Res. 34, 65–142 (1988).

Nixon, D.F., Townsend, A.R.M., Elvin, J.G., Rizza, C.R., Gallwey, J. and McMichael, A.J., Nature 326, 484–487 (1988).

Norrby, E., S.N. Chen, T. Togashi, H. Shesberadaran, and K.P. Johnson, Archives of Virology 71, 1–11 (1982).

Norrby, E., and M.N. Oxman, In Fields Virology, 2nd Edition, eds. B.N. Fields and D.M. Knipe, (Raven Press, NY) pp. 1013–1044 (1990).

Norrby, E., and Y. Gollmar, Infect. and Immun. 11, 231–239 (1975).

Norrby, E. Utter, G., Orvell, C., and M.J.G. Appel, J. Virol. 58, 536–541 (1986).

Norrby, E., G. Enders–Ruckle, and V. ter Meulen, J. Infect. Dis. 132, 262–269 (1975).

Novick, S.L. and Hoekstra, D., Proc. Nat. Acad. Sci. USA 85, 7433–7437 (1988).

Oakes, J. and Rosemond–Hornbeak, H., Infect. Immun. 21, 489–495 (1978).

Oakes, J., Davis, W., Taylor, J. and Weppner, W., Infect. Immun. 29, 642–649 (1980).

Ogawa, R., Yanagida, N., Saeki, S., Saito, S., Ohkawa, S., Gotoh, H., Kodama, K., Kamogawa, K., Sawagucki, K., and Iritani, Y. Vaccine 8, 486–490 (1990).

Ono, Y., H. Onda, R. Sasada, K. Igarashi, Y. Sugino and K. Nishioka, Nuc. Acids Res. 11, 1747–1757 (1983).

Orvell, C., and E. Norrby, J. Gen. Virol. 50, 231–245 (1980).

Ou, J–H. and W. J. Rutter, J. Virol. 61, 782–786 (1987).

Paez, E., S. Dallo and M. Esteban, Proc. Natl. Acad. Sci. USA 82, 3365–3369 (1985).

Palumbo, G.J., Pickup, D.J., Fredrickson, T.N., Mcintyre, L.J. and Buller, R.M.L., Virology 172, 262–273 (1989).

Panicali, D. and E. Paoletti, Proc. Natl. Acad. Sci. USA 79, 4927–4931 (1982).

Panicali, D., Davis, S.W., Mercer, S.R., and Paoletti, E., J. Virol. 37, 1000–1010 (1981).

Paoletti, E., B. Lipinskas, C. Samsonoff, S. Mercer and D. Panicali, Proc. Natl. Acad. Sci. USA 81, 193–197 (1984).

Patel, D.D. and Pickup, D.J. EMBO J. 6, 3787–3794 (1987).

Paterson, R.G. and R.A. Lamb, Cell 48, 441–452 (1987).

Patel, D.D., Ray, C.A., Drucker, R.P., and Pickup, D.J., Proc. Natl. Acad. Sci. USA 85, 9431–9435 (1988).

Perkus, M. E., D. Panicali, S. Mercer and E. Paoletti, Virology 152, 285–297 (1986).

Perkus, M.E., A. Piccini, B.R. Lipinskas and E. Paoletti, Science 229, 981–984 (1985).

Perkus, M.E., Limbach, K., and Paoletti, E., J. Virol. 63, 3829–3836 (1989).

Perkus, M.E., Goebel, S.J., Davis, S.W., Johnson, G.P., Limbach, K., Norton, E.K., and Paoletti, E., Virology 179, 276–286 (1990).

Perkus, M.E., S.J. Goebel, S.W. Davis, G.P. Johnson, E.K. Norton and E. Paoletti, Virology 180, 406–410 (1991).

Petrovskis, E.A., J.G. Timmins, and L.E. Post, J. Virol. 60, 185–193 (1986a).

Petrovskis, E.A., Timmins, J.G., Armentrout, M.A., Marchioli, C.C., Yancey, Jr., R.J., Post, L.E., J. Virol. 59, 216–223 (1986b).

Phillips, T.R., J.L. Jensen, M.J. Rubino, W.C. Yang, and R.D. Schultz, Can. J. Vet. Res. 53, 154–160 (1989).

Piccini et al., *Bioessays* (Jun. 1986) vol. 5, No. 6, 248–252.

Piccini, A., M.E. Perkus, and E. Paoletti, In Methods in Enzymology 153, 545–563 (1987).

Pickup, D.J., B.S. Ink, B.L. Parsons, W. Hu and W.K. Joklik, Proc. Natl. Acad. Sci. USA 81, 6817–6821 (1984).

Pickup, D.J., B.S. Ink, W. Hu, C.A. Ray and W.K. Joklik, Proc. Natl. Acad. Sci. USA 83, 7698–7702 (1986).

Plata, F., Autran, B., Martins, L.P., Wain–Hobson, S., Raphael, M., Mayaud, C., Denis, M., Guillon, J.–M. Debre, P., Nature 328, 348–351 (1987).

Pontisso, P, M–A. Petit, M. J. Bankowski and M. E. Peeples, J. Virol. 63, 1981–1988 (1989).

Portetelle, D., Limbach, K., Burny, A., Mammerickx, M., Desmettre, P., Riviere, M., Zavada, J. and Paoletti, E. Vaccine 9, 194–200 (1991).

Powell, K. and Watson, D.J., Gen. Virol. 29, 167–178 (1975).

Pratt, D. and S. Subramani, Nucleic Acids Research 11, 8817–8823 (1983).

Preblud, S.R. and S.L. Katz, In Vaccines, eds. S.A. Plotkin and E.A. Mortimer, (W.B. Saunders Co.) pp. 182–222 (1988).

Prevec, L., J.B. Cambpell, B.S. Christie, L. Belbek, and F.L. Graham, J. Infect. Dis. 161, 27–30 (1990).

Ratner, L., Haseltine, W., Patarka, R., Livak, K.J., Starcich, B., Josephs, S.F., Doran, E.R., Rafalski, J.A., Whitehorn, E.A., Baumeister, K., Ivanoff, L., Petteway, Jr., S.R., Pearson, M.L., Lautenberger, J.A., Papas, T.S., Ghrayeb, J., Chang, N.T., Gallo., R.C., and Wong–Staal F., Nature 313, 277–281.

Rautmann, G., Kieny, M.P., Brandely, R., Dott, K., Girard, M., Montagnier, L., and Lecocq, J.–P., AIDS Research and Human Retroviruses 5, 147–157 (1989).

Rea, T.J., J.G. Timmins, G.W. Long, and L.E. Post, J. Virol. 54, 21–29 (1985).

Reed, L.J. and Muench, H., Am. J. Hyg. 27, 493–497 (1938).

Rice, C. M., Lenches, E. M., Eddy, S. R., Shin, S. J., Sheets, R. L., and Strauss, J. H., Science 229, 726–733 (1985).

Richardson, C.D., A. Berkovich, S. Rozenblatt, and W. Bellini, J. Virol. 54, 186–193 (1985).

Richardson, C., D. Hull, P. Greer, K. Hasel, A. Berkovich, G. Englund, W. Bellini, B. Rima, and R. Lazzarini, Virology 155, 508–528 (1986).

Riviere Y., Tanneau–Salvadori, F., Regnault, A., Lopez, O., Sansonetti, P., Guy, B., Keiny, M.–P., Fournel, J.–J. and Montagnier, L., J. Virol. 63, 2270–2277 (1989).

Robbins, A.K., Dorney, D.J., Wathen, M.W., Whealy, M.E., Gold, C., Watson, R.J., Holland, L.E., Weed, S.D., Levine, M., Gloricso, J.C., and Enquist, L.W., J. Virol. 61, 2691–2701 (1987).

Robbins, A.K., J.H. Weis, L.W. Enquist, and R.J. Watson, J. Mol. Appl. Genet. 2, 485–496 (1984).

Robbins, A.K., R.J. Watson, M.E. Whealy, W.W. Hayes, and L.W. Enquist, J. Virol. 58, 339–347 (1986a).

Roberts, J.A., J. Immunol. 94, 622–628 (1965).

Rodriquez et al., Proc. Natl. Acad. Sci USA 86, 1287–1291 (1989).

Roizman, B. and Sears, A., In Virology, eds. Fields, B. and Knipe, D., (Raven Press. Ltd) pp. 1795–1841 (1990).

Rooney F.F., Wohlenberg C., Cramer E.J. et al., J. Virol. 62, 1530–1534 (1988).

Rosel, J.L., Earl, P.L., Weir, J.P., and B. Moss, J. Virol. 60 436–449 (1986).

Rosenthal K., Smiley, S., South, S. and Johnson, D., J. Virol. 61, 2438–2447 (1987).

Rubenstein, A.S. and A.S. Kaplan, Virology 66, 385–392 (1975).

Ruegg, C.L., Monell, C.R. and Strand, M., J. Virol. 63, 3250–3256 (1989a).

Ruegg, C.L., Monell, C.R., and Strand M., J. Virol. 63, 3257–3260 (1989b).

Saiki, R., Gelfand, D., Stoffel, S., Scharf, S., Higuchi, R., Horn, G., Mullis, K., and Erlich, H., Science 239, 487–491 (1988).

Sanger, F., Nickeln, S. Coulson, A.R., Proc. Natl. Acad. Sci. 74, 5463–5467 (1977).

Scheid, A., and P.W. Choppin, Virology 57, 475–490 (1974).

Scheid, A., L.A. Caliguiri, R.W. Compans, and P.W. Choppin, Virology 50, 640–652 (1972).

Schlesinger, J.J., Brandriss, M.W., Cropp, C.B., and Monath, T.P., J. Virol. 60, 1153–1155 (1986).

Schlesinger, J.J., Brandriss, M.W., and Walsh, E.E., J. Immunol. 135, 2805–2809 (1985).

Schlesinger, J.J., Brabdriss, M.W., and E.E., J Gen. Virol. 68, 853–857 (1987).

Schlicht, H–J. and H. Schaller, J. Virol. 63, 5399–5404 (1989).

Schmaljohn, C.S., Chu, Y.K., Schmaljohn, A.L., and Dalrymple, J.M., J. Virology 64, 3162–3170 (1990).

Schmidtt, J.F.C. and H.G. Stunnenberg, J. Virol. 62, 1889–1897 (1988).

Shafferman, A., Lennox, J., Grosfeld, H., Sadoff, J., Redfield, R. R., and Burke, D. S., AIDS Research and Human Retroviruses 5, 33–39 (1989).

Shapira, S.K., J. Chou, F.V. Richaud, and M.J. Casadaban, Gene 25, 71–82 (1983).

Shida, H., Virology 150, 451–462 (1986).

Shida, H., T. Tochikura, T. Sato, T. Konno, K. Hirayoshi, M. Seki, Y. Ito, M. Hatanaka, Y. Hinuma, M. Sugimoto, F. Takahashi–Nishimaki, T. Maruyama, K. Miki, K. Suzuki, M. Morita, H. Sashiyama and M. Hayami, EMBO 6, 3379–3384 (1987).

Shida, H., Hinuma, Y., Hatanaka, M., Morita, M., Kidokoro, M., Suzuki, K., Maruyzam, T., Takahashi–Nishimaki, F., Sugimoto, M., Kitamura, R., Miyazawa, T., and Hayami, M., J. Virol. 62, 4474–4480 (1988).

Shioda, T. and H. Shibuta, Virology 175, 139–148 (1990).

Shope, R.E., In The Togaviruses, ed. R.W. Schlesinger, (Academic Press, New York) pp. 47–82 (1980).

Slabaugh, M. B. and N. A. Roseman, Proc. Natl Acad. Sci. USA 86, 4152–4155 (1989).

Slabaugh, M., N. Roseman, R. Davis and C. Mathews, J. Virol. 62, 519–527 (1988).

Smith, G.L., M. Mackett and B. Moss, Nature 302, 490–495 (1983).

Smith, J.S., P.A. Yager and G.M. Baer, In Laboratory Techniques in Rabies, eds. M. M. Kaplan and H. Koprowski (Who Geneva) pp. 354–357 (1973).

Spear, P., In Herpesviruses, vol. 3, ed. Roizman, B. (Plenum, NY) pp. 315–356 (1984).

Spehner, D., R. Drillien, and J. P. Lecocq, J. Virol. 64, 527–533 (1990).

Stahl, S. J. and K. Murray, Proc. Natl. Acad. Sci. USA 86, 6283–6287 (1989).

Stanberry, L. R., S. Kit and M. G. Meyers, J. Virol. 55, 322–328 (1985).

Starcich et al., Cell 45, 637–648 (1986).

Stephenson, J.R. and V. ter Meulen, Proc. Nat. Acad. Sci. USA 76, 6601–6605 (1979).

Stevely, W.S., J. Virol. 22, 232–234 (1977).

Tabor, S. and C. C. Richardson, Proc. Natl. Acad. Sci. USA 84, 4767–4771 (1987).

Tartaglia, J., Critical Reviews in Immunology 13, 15–30 (1990a).

Tartaglia, J., S. Pincus and E. Paoletti, Critical Reviews in Immunology 10, 13–30 (1990a).

Tartaglia, J., Perkus, M.E., Taylor, J., Norton, E.K., Audonnet, J.-C., Cox, W.I., Davis, S.W., Van Der Hoeven, J., Meignier, B., Riviere, M., Languet, B., Paoletti, E., Virology 188, 217–232 (1992).

Taylor, J., Edbauer, C., Rey–Senelonge, A., Bouquet, J.-F., Norton, E., Goebel, S., Desmettre, P., Paoletti, E., J. Virol. 64, 1441–1450 (1990).

Taylor, G., E. J. Stott, G. Wertz and A. Ball, J. Gen. Virol. 72, 125–130 (1991a).

Taylor, J., C. Trimarchi, R. Weinberg, B. Languet, F. Guillemin, P. Desmettre and E. Paoletti, Vaccine 9, 190–193 (1991b).

Taylor, J., S. Pincus, J. Tartaglia, C. Richardson, G. Alkhatib, D. Briedis, M. Appel, E. Norton, and E. Paoletti, J. Virol. 65, 4263–4272 (1991d).

Taylor, J., R. Weinberg, B. Languet, P. Desmettre, and E. Paoletti, Vaccine 6, 497–503 (1988b).

Taylor, J., Weinberg, Y., Kawaoka, Y., Webster, R.G., and Paoletti, E., Vaccine 6, 504–508 (1988a).

Taylor, J. et al, Vaccine 6, 466–467 (1988c).

Thornton, G. B., D. Milich, F. Chisari, K. Mitamura, S. B. Kent, R. Neurath, R. Purcell and J. Gerin, In Vaccines 87, (Cold Spring Harbor Laboratory, Cold Spring Harbor, New York) 1987).

Tizard, I., J. Am. Vet. Med. Assoc. 196, 1851–1858 (1990).

Tomley, F., Vaccine 9, 4–5 (1991).

Toyoda, T., Sakaguchi, T., Imai, K., Inocencio, N.M., Gotoh, B., Hamaguchi, M., and Nagai, Y. Virology 158, 242–247.

Turner, P.C. (90) Current Topics in Microbiol & Immunology 163, pp. 125–151.

Ueda, Y., S. Morikawa and Y. Matsuura, Virology 177, 588–594 (1990).

Valenzuela, P. P. Gray, M. Quiroga, J. Zaldivar, H. M. Goodman and W. J. Rutter, Nature 280, 815–819 (1979).

Valenzuela, P., D. Coit, M. A. Medina–Selby, C. H. Kuo, G. V. Nest, R. L. Burke, P. Bull, M. S. Urdea P.V. Graves, Bio/Technology 3, 323–326 (1985).

Valenzuela, P., A. Medina, W. J. Rutter, G. Ammerer and B. D. Hall, Nature 298, 347–350 (1982).

Vialard, J., M. Lalumiere, T. Vernet, D. Briedis, G. Alkathib, D. Henning, D. Levin and C. Richardson, Virol. 64, 37–50 (1990).

Vos, J. C. and Stunnenberg, H. G., EMBO J. 7, 3487–3492 (1988).

Wachsman, M., Aurelian, L., Smith, C., Lipinskas, S., Perkus, M. and Paoletti, E., J. Infect. Dis. 155, 1188–1197 (1987).

Walker, B. D., Flexner, C., Birch–Limberger, K., Fisher, L., Paradis, T. J., Aldovini, A., Young, R., Moss, B., and Schooley, R. T., Proc. Natl. Acad. Sci. 86, 9514–9519 (1989).

Walker, B. D., Chakrabarti, S., Moss, B., Paradi, T. J., Flynn, T., Durno, A. G., Blumberg, R. S., Kaplan, J. C., Hirsch, M. S., and Schooley, R. T., Nature 328, 345–348 (1987).

Walker, B. D., Flexner, C., Paradis, T. J., Fuller, T. C., Hirsch, M. S., Schooley, R. T. and Moss, B., Science 240, 64–66 (1988).

Warren, J., M.K. Nadel, E. Slater, and S.J. Millian, Amer. J. Vet. Res. 21, 111–119 (1960).

Wathen, M.W. and Wathen, L.M.K., J. Virol. 51, 57–62 (1984).

Watson, R., Gene 26, 307–312 (1983).

Weir, J., Bennett, M., Allen, E., Elkins, K., Martin, S. and Rouse, B., J. Gen. Virol. 70, 2587–2594 (1989).

Weir, J.P. and B. Moss, J. Virol. 46, 530–537 (1983).

Weiss, R. A., Clapham, P. R., Cheingsong–Popov, R., Dalgleish, G., Carne, C. A. Weller, I. V., and Tedder, R. S., Nature 316, 69–72 (1985).

Wengler, G., and Wengler, G., J. Virol. 63, 2521–2526 (1989a).

Wengler, G., and Wengler, G., J. Gen. Virol. 70, 987–992 (1989b).

Wiktor, T. J., E. Gyorgy, H.D. Schlumberger, F. Sokol and H. Koprowski, J. Immunol. 110, 269–276 (1973).

Wiktor, T. J., R. I. Macfarlan, K. J. Reagan, B. Dietzschold, P. J. Curtis, W. H. Wunner, M. P. Kieny, R. Lathe, J. P. Lecocq, M. Mackett, B. Moss and H. Koprowski, Proc. Natl. Acad. Sci. USA 81, 7194–7198 (1984).

Wiktor, T. J., S.A. Plotkin and H. Koprowski, In Vaccines, eds. Plotkin, S.A. and E.A. Mortimer (W.B. Saunders, Philadelphia), 474–491 (1988).

Wild, F., P. Giraudon, D. Spehner, R. Drillien, and J–P. Lecocq, Vaccine 8, 441–442 (1990).

Wild, T.F., E. Malvoisin, and R. Buckland, J. Gen. Virol. 72, 439–447 (1991a).

Wilson, E.M., Hodges and D.E. Hruby, Gene 49, 207–213 (1986).

Winkler, G., Randolph, V.B., Cleaves, G.R., Ryan, T.E., and Stollar, V., Virol 162, 187–196 (1988).

Wittmann, G. and Rziha, H.-J. Aujeszky's disease (pseudorabies) in pigs, In Herpesvirus Diseases of Cattle, Horses and Pigs, ed Whittmann, G., (Kluwer Academic Publishers), 230–325 (1989).

Wunner, W.H., B. Dietzschold, P.J. Curtis and T.J. Wiktor, J. Gen. Virol. 64, 1649–1656 (1983).

Yelverton, E., S. Norton, J.F. Obijeski and D.V. Goeddel, Science 219, 614–620 (1983).

Yuen, L., and Moss, B., Proc. Natl. Acad. Sci. USA 84, 6417–6421 (1987).

Zagury, D., Bernard, J., Cheynier, R., Desportes, I., Leonard, R., Fouchard, I., Reveil, B., Ittele, D., Lurhuma, Z., Mbayo, K., Wane, J., Salaun, J.-J., Goussard, B., Dechazal, L., Burny, A., Nara, P. and Gallo, R.C., Nature 332, 728–731 (1988).

Zanetti, A.R., E. Tanzi, L. Romano, P. Vigano, A. Cargnel, S. Hojvat and A.J. Zuckerman, J. Med. Virol. 32, 219–224 (1990).

Zhou, J., L. Crawford, L. McLean, X. Sun, M. Stanley, N. Almond and G.L. Smith, J. Gen. Virol. 71, 2185–2190 (1990).

Zingernagel, R.M., Sato, T., Althage, A., and Kamisaku, H., Eur. J. Immunol. 14, 14–23 (1984).

Zweig, M., Showalter, S., Bladen, S., Heilman, C. and Hamper, B., J. Virol. 47, 185–192 (1983).

Cadoz, M., A. Strady, B. Meignier, J. Taylor, J. Tartaglia, E. Paoletti and S. Plotkin, The Lancet, 339, 1429 (1992).

Curran, M.D., Clarke, D.K., and Rima, B.K., J. Gen. Virol. 72, 443–447 (1991).

Tartaglia, J., J. Taylor, W.I. Cox, J.–C. Audonnet, M.E. Perkus, A. Radaelli, C. de Giuli Morghen, B. Meignier, M. Riviere, K. Weinhold & E. Paoletti, In AIDS Research Reviews, W. Koff, F. Wong–Staal & R.C. Kenedy, Eds., vol. 3, Marcel Dekker, NY (In press) (1993a).

Tartaglia, J. & E. Paoletti, In Immunochemistry of Viruses, II. The Basis for Serodiagnosis and Vaccines. M.H.V. van Regenomortel & A.R. Neurath, Eds. 125–151. Elsevier Science Publishers, Amsterdam (1990).

Tartaglia, J., Jarrett, O., Desmettre, P., Paoletti, E., J. Virol. 67, 2370–2375 (1993b).

| | | | |
|---|---|---|---|
| 1 | TGAATGTTAA | ATGTTATACT | TTGGATGAAG |
| 31 | CTATAAATAT | GCATTGGAAA | AATAATCCAT |
| 61 | TTAAAGAAAG | GATTCAAATA | CTACAAAACC |
| 91 | TAAGCGATAA | TATGTTAACT | AAGCTTATTC |
| 121 | TTAACGACGC | TTTAAATATA | CACAAATAAA |
| 151 | CATAATTTTT | GTATAACCTA | ACAAATAACT |
| 181 | AAAACATAAA | AATAATAAAA | GGAAATGTAA |
| 211 | TATCGTAATT | ATTTACTCA | GGAATGGGGT |
| 241 | TAAATATTTA | TATCACGTGT | ATATCTATAC |
| 271 | TGTTATCGTA | TACACTTTAC | AATTACTATT |
| 301 | ACGAATATGC | AAGAGATAAT | AAGATTACGT |
| 331 | ATTTAAGAGA | ATCTTGTCAT | GATAATTGGG |
| 361 | TACGACATAG | TGATAAATGC | TATTTCGCAT |
| 391 | CGTTACATAA | AGTCAGTTGG | AAAGATGGAT |
| 421 | TTGACAGATG | TAACTTAATA | GGTGCAAAAA |
| 451 | TGTTAAATAA | CAGCATTCTA | TCGGAAGATA |
| 481 | GGATACCAGT | TATATTATAC | AAAAATCACT |
| 511 | GGTTGGATAA | AACAGATTCT | GCAATATTCG |
| 541 | TAAAAGATGA | AGATTACTGC | GAATTTGTAA |
| 571 | ACTATGACAA | TAAAAAGCCA | TTTATCTCAA |
| 601 | CGACATCGTG | TAATTCTTCC | ATGTTTATG |
| 631 | TATGTGTTTC | AGATATTATG | AGATTACTAT |
| 661 | AAACTTTTTG | TATACTTATA | TTCCGTAAAC |
| 691 | TATATTAATC | ATGAAGAAAA | TGAAAAAGTA |
| 721 | TAGAAGCTGT | TCACGAGCGG | TTGTTGAAAA |
| 751 | CAACAAAATT | ATACATTCAA | GATGGCTTAC |
| 781 | ATATACGTCT | GTGAGGCTAT | CATGGATAAT |
| 811 | GACAATGCAT | CTCTAAATAG | GTTTTTGGAC |
| 841 | AATGGATTCG | ACCCTAACAC | GGAATATGGT |
| 871 | ACTCTACAAT | CTCCTCTTGA | AATGGCTGTA |
| 901 | ATGTTCAAGA | ATACCGAGGC | TATAAAAATC |
| 931 | TTGATGAGGT | ATGGAGCTAA | ACCTGTAGTT |
| 961 | ACTGAATGCA | CAACTTCTTG | TCTGCATGAT |
| 991 | GCGGTGTTGA | GAGACGACTA | CAAAATAGTG |
| 1021 | AAAGATCTGT | TGAAGAATAA | CTATGTAAAC |
| 1051 | AATGTTCTTT | ACAGCGGAGG | CTTTACTCCT |
| 1081 | TTGTGTTTGG | CAGCTTACCT | TAACAAAGTT |
| 1111 | AATTTGGTTA | AACTTCTATT | GGCTCATTCG |
| 1141 | GCGGATGTAG | ATATTTCAAA | CACGGATCGG |
| 1171 | TTAACTCCTC | TACATATAGC | CGTATCAAAT |
| 1201 | AAAAATTTAA | CAATGGTTAA | ACTTCTATTG |
| 1231 | AACAAAGGTG | CTGATACTGA | CTTGCTGGAT |
| 1261 | AACATGGAC | GTACTCCTTT | AATGATCGCT |
| 1291 | GTACAATCTG | GAAATATTGA | AATATGTAGC |

FIG. 8B

| | | | |
|---|---|---|---|
| 1321 | ACACTACTTA | AAAAAAATAA | AATGTCAGAA |
| 1351 | CTGGAAAAA | TTGATCTTGC | CAGCTGTAAT |
| 1381 | TCATGGTAGA | AAAGAAGTGC | TCAGGCTACT |
| 1411 | TTTCAACAAA | GGAGCAGATG | TAAACTACAT |
| 1441 | CTTTGAAAGA | AATGGAAAAT | CATATACTGT |
| 1471 | TTTGGAATTG | ATTAAAGAAA | GTTACTCTGA |
| 1501 | GACACAAAAG | AGGTAGCTGA | AGTGGTACTC |
| 1531 | TCAAAATGCA | GAACGATGAC | TGCGAAGCAA |
| 1561 | GAAGTAGAGA | AATAACACTT | TATGACTTTC |
| 1591 | TTAGTTGTAG | AAAAGATAGA | GATATAATGA |
| 1621 | TGGTCATAAA | TAACTCTGAT | ATTGCAAGTA |
| 1651 | AATGCAATAA | TAAGTTAGAT | TTATTTAAAA |
| 1681 | GGATAGTTAA | AAATAGAAAA | AAAGAGTTAA |
| 1711 | TTTGTAGGGT | TAAAATAATA | CATAAGATCT |
| 1741 | TAAAATTTAT | AAATACGCAT | AATAATAAAA |
| 1771 | ATAGATTATA | CTTATTACCT | TCAGAGATAA |
| 1801 | AATTTAAGAT | ATTTACTTAT | TTAACTTATA |
| 1831 | AAGATCTAAA | ATGCATAATT | TCTAAATAAT |
| 1861 | GAAAAAAAG | TACATCATGA | GCAACGCGTT |
| 1891 | AGTATATTTT | ACAATGGAGA | TTAACGCTCT |
| 1921 | ATACCGTTCT | ATGTTTATTG | ATTCAGATGA |
| 1951 | TGTTTAGAA | AAGAAAGTTA | TTGAATATGA |
| 1981 | AAACTTTAAT | GAAGATGAAG | ATGACGACGA |
| 2211 | TGATTATTGT | TGTAAATCTG | TTTTAGATGA |
| 2041 | AGAAGATGAC | GCGCTAAAGT | ATACTATGGT |
| 2071 | TACAAAGTAT | AAGTCTATAC | TACTAATGGC |
| 2101 | GACTTGTGCA | AGAAGGTATA | GTATAGTGAA |
| 2131 | AATGTTGTTA | GATTATGATT | ATGAAAAACC |
| 2161 | AAATAAATCA | GATCCATATC | TAAAGGTATC |
| 2191 | TCCTTTGCAC | ATAATTTCAT | CTATTCCTAG |
| 2221 | TTTAGAATAC | TTTTCATTAT | ATTTGTTTAC |
| 2251 | AGCTGAAGAC | GAAAAAAATA | TATCGATAAT |
| 2281 | AGAAGATTAT | GTTAACTCTG | CTAATAAGAT |
| 2311 | GAAATTGAAT | GAGTCTGTGA | TAATAGCTAT |
| 2341 | AATCAGAGAA | GTTCTAAAAG | GAAATAAAAA |
| 2371 | TCTAACTGAT | CAGGATATAA | AAACATTGGC |
| 2401 | TGATGAAATC | AACAAGGAGG | AACTGAATAT |
| 2431 | AGCTAAACTA | TTGTTAGATA | GAGGGGCCAA |
| 2461 | AGTAAATTAC | AAGGATGTTT | ACGGTTCTTC |
| 2491 | AGCTCTCCAT | AGAGCTGCTA | TTGGTAGGAA |
| 2521 | ACAGGATATG | ATAAAGCTGT | TAATCGATCA |
| 2551 | TGGAGCTGAT | GTAAACTCTT | TAACTATTGC |
| 2581 | TAAAGATAAT | CTTATTAAAA | AAAAATAATA |
| 2611 | TCACGTTTAG | TAATATTAAA | ATATATTAAT |

FIG. 8C

| | | | |
|---|---|---|---|
| 2641 | AACTCTATTA | CTAATAACTC | CAGTGGATAT |
| 2671 | GAACATAATA | CGAAGTTTAT | ACATTCTCAT |
| 2701 | CAAAATCTTA | TTGACATCAA | GTTAGATTGT |
| 2731 | GAAAATGAGA | TTATGAAATT | AAGGAATACA |
| 2761 | AAAATAGGAT | GTAAGAACTT | ACTAGAATGT |
| 2791 | TTTATCAATA | ATGATATGAA | TACAGTATCT |
| 2821 | AGGGCTATAA | ACAATGAAAC | GATTAAAAAT |
| 2851 | TATAAAAATC | ATTTCCCTAT | ATATAATACG |
| 2881 | CTCATAGAAA | AATTCATTTC | TGAAAGTATA |
| 2911 | CTAAGACACG | AATTATTGGA | TGGAGTTATA |
| 2941 | AATTCTTTTC | AAGGATTCAA | TAATAAATTG |
| 2971 | CCTTACGAGA | TTCAGTACAT | TATACTGGAG |
| 3001 | AATCTTAATA | ACCATGAACT | AAAAAAAATT |
| 3031 | TTAGATAATA | TACATTAAAA | AGGTAAATAG |
| 3061 | ATCATCTGTT | ATTATAAGCA | AAGATGCTTG |
| 3091 | TTGCCAATAA | TATACAACAG | GTATTTGTTT |
| 3121 | TTATTTTTAA | CTACATATTT | GATGTTCATT |
| 3151 | CTCTTTATAT | AGTATACACA | GAAAATTCAT |
| 3181 | AATCCACTTA | GAATTTCTAG | TTATCTAG |

```
   1    GATATCTGTG    GTCTATATAT    ACTACACCCT
  31    ACCGATATTA    ACCAACGAGT    TTCTCACAAG
  61    AAAACTTGTT    TAGTAGATAG    AGATTCTTTG
  91    ATTGTGTTTA    AAAGAAGTAC    CAGTAAAAAG
 121    TGTGGCATAT    GCATAGAAGA    AATAAACAAA
 151    AAACATATTT    CCGAACAGTA    TTTTGGAATT
 181    CTCCCAAGTT    GTAAACATAT    TTTTTGCCTA
 211    TCATGTATAA    GACGTTGGGC    AGATACTACC
 241    AGAAATACAG    ATACTGAAAA    TACGTGTCCT
 271    GAATGTAGAA    TAGTTTTTCC    TTTCATAATA
 301    CCCAGTAGGT    ATTGGATAGA    TAATAAATAT
 331    GATAAAAAAA    TATTATATAA    TAGATATAAG
 361    AAAATGATTT    TTACAAAAAT    ACCTATAAGA
 391    ACAATAAAAA    TATAATTACA    TTTACGGAAA
 421    ATAGCTGGTT    TTAGTTTACC    AACTTAGAGT
 451    AATTATCATA    TTGAATCTAT    ATTGTTTTTT
 481    AGTTATATAA    AAACATGATT    AGCCCCCAAT
 511    CGGATGAAAA    TATAAAGAT     GTTGAGAATT
 541    TCGAATACAA    CAAAAGAGG     AATCGTACGT
 571    TGTCCATATC    CAAACATATA    AATAAAAATT
 601    CAAAAGTAGT    ATTATACTGG    ATGTTTAGAG
 631    ATCAACGTGT    ACAAGATAAT    TGGGCTTTAA
 661    TTTACGCACA    ACGATTAGCG    TTAAAACTCA
 691    AAATACCTCT    AAGAATATGC    TTTTGTGTCG
 721    TGCCAAAATT    TCACACTACT    ACTTCTAGAC
 751    ACTTTATGTT    TTTAATATCC    GGTCTTAAAG
 781    AAGTCGCGGA    AGAATGTAAA    AGACTATGTA
 811    TAGGGTTTTC    ATTGATATAT    GGCGTACCAA
 841    AAGTAATAAT    TCCGTGTATA    GTAAAAAAT
 871    ACAGAGTCGG    AGTAATCATA    ACGGATTTCT
 901    TTCCATTACG    TGTTCCCGAA    AGATTAATGA
 931    AACAGACTGT    AATATCTCTT    CCAGATAACA
 961    TACCTTTTAT    ACAAGTAGAC    GCTCATAATA
 991    TAGTACCTTG    TTGGGAAGCT    TCTGATAAAG
1021    AAGAATACGG    TGCACGAACT    TTAAGAAAAA
1051    AGATATTTGA    TAAATTATAT    GAATATATGA
1081    CAGAATTTCC    TGTTGTTCGT    AAACATCCAT
1111    ACGGTCCATT    TTCTATATCT    ATTGCAAAAC
1141    CCAAAAATAT    ATCATTAGAC    AAGACGGTAT
1171    TACCCGTAAA    ATGGGCAACG    CCTGGAACAA
1201    AAGCTGGAAT    AATTGTTTA     AAAGAATTTA
1231    TAAAAACAG     ATTACCGTCA    TACGACGCGG
1261    ATCATAACAA    TCCTACGTGT    GACGCTTTGA
1291    GTAACTTATC    TCCGTGGCTA    CATTTTGGTC
```

FIG. 11B

```
1321    ATGTATCCGC    ACAACGTGTT    GCCTTAGAAG
1351    TATTAAAATG    TATACGAGAA    AGCAAAAAAA
1381    ACGTTGAAAC    GTTTATAGAT    GAAATAATTG
1411    TAAGAAGAGA    ACTATCGGAT    AATTTTTGTT
1441    ACTATAACAA    ACATTATGAT    AGTATCCAGT
1471    CTACTCATTC    ATGGGTTAGA    AAAACATTAG
1501    AAGATACAT     TAATGATCCT    AGAAAGTATA
1531    TATATTCCAT    TAAACAACTC    GAAAAAGCGG
1561    AAACTCATGA    TCCTCTATGG    AACGCGTCAC
1591    AAATGCAGAT    GGTGAGAGAA    GGAAAAATGC
1621    ATAGTTTTT     ACGAATGTAT    TGGGCTAAGA
1651    AGATACTTGA    ATGGACTAGA    ACACCTGAAG
1681    ACGCTTTGAG    TTATAGTATC    TATTTGAACA
1711    ACAAGTACGA    ACTAGACGGC    ACGGATCCTA
1741    ACGGATACGT    AGGTTGTATG    TGGTCTATTT
1771    GCGGATTACA    CGATAGAGCG    TGGAAAGCAA
1801    GACCGATATT    TGGAAAGATA    AGATATATGA
1831    ATTATGAGAG    TTCTAAGAAG    AAATTTGATG
1861    TTGCTGTATT    TATACAGAAA    TACAATTAAG
1891    ATAAATAATA    TACAGCATTG    TAACCATCGT
1921    CATCCGTTAT    ACGGGAATA     ATATTACCAT
1951    ACAGTATTAT    TAAATTTCT     TACGAAGAAT
1981    ATAGATCGGT    ATTTATCGTT    AGTTTATTTT
2011    ACATTTATTA    ATTAAACATG    TCTACTATTA
2041    CCTGTTATGG    AAATGACAAA    TTTAGTTATA
2071    TAATTTATGA    TAAAATTAAG    ATAATAATAA
2101    TGAAATCAAA    TAATTATGTA    AATGCTACTA
2141    GATTATGTGA    ATTACGAGGA    AGAAAGTTTA
2161    CGAACTGGAA    AAAATTAAGT    GAATCTAAAA
2191    TATTAGTCGA    TAATGTAAAA    AAAATAAATG
2221    ATAAAACTAA    CCAGTTAAAA    ACGGATATGA
2251    TTATATACGT    TAAGGATATT    GATCATAAAG
2281    GAAGAGATAC    TTGCGGTTAC    TATGTACACC
2311    AAGATCTGGT    ATCTTCTATA    TCAAATTGGA
2341    TATCTCCGTT    ATTCGCCGTT    AAGGTAAATA
2371    AAATTATTAA    CTATTATATA    TGTAATGAAT
2401    ATGATATACG    ACTTAGCGAA    ATGGAATCTG
2431    ATATGACAGA    AGTAATAGAT    GTAGTTGATA
2461    AATTAGTAGG    AGGATACAAT    GATGAAATAG
2491    CAGAAATAAT    ATATTTGTTT    AATAAATTTA
2521    TAGAAAAATA    TATTGCTAAC    ATATCGTTAT
2551    CAACTGAATT    ATCTAGTATA    TTAAATAATT
2581    TTATAAATTT    TATAAATTTT    AATAAAAAT
2611    ACAATAACGA    CATAAGATA     TTTAATCTTT
```

FIG. 11C

```
2641  AATTCTTGAT  CTGAAAAACA  CATCTATAAA
2671  ACTAGATAAA  AAGTTATTCG  ATAAAGATAA
2701  TAATGAATCG  AACGATGAAA  AATTGGAAAC
2731  AGAAGTTGAT  AAGCTAATTT  TTTTCATCTA
2761  AATAGTATTA  TTTTATTGAA  GTACGAAGTT
2791  TTACGTTAGA  TAAATAATAA  AGGTCGATTT
2821  TTACTTTGTT  AAATATCAAA  TATGTCATTA
2851  TCTGATAAAG  ATACAAAAAC  ACACGGTGAT
2881  TATCAACCAT  CTAACGAACA  GATATTACAA
2911  AAAATACGTC  GGACTATGGA  AAACGAAGCT
2941  GATAGCCTCA  ATAGAAGAAG  CATTAAAGAA
2971  ATTGTTGTAG  ATGTTATGAA  GAATTGGGAT
3001  CATCCTCAAC  GAAGAAATAG  ATAAAGTTCT
3031  AAACTGGAAA  AATGATACAT  TAAACGATTT
3061  AGATCATCTA  AATACAGATG  ATAATATTAA
3091  GGAAATCATA  CAATGTCTGA  TTAGAGAATT
3121  TGCGTTTAAA  AAGATCAATT  CTATTATGTA
3151  TAGTTATGCT  ATGGTAAAAC  TCAATTCAGA
3181  TAACGAACAT  TGAAAGATAA  AATTAAGGAT
3211  TATTTTATAG  AAACTATTCT  TAAAGACAAA
3241  CGTGGTTATA  AACAAAAGCC  ATTACCCGGA
3271  TTGGAAACTA  AAATACTAGA  TAGTATTATA
3301  AGATTTTAAA  AACATAAAAT  TAATAGGTTT
3331  TTATAGATTG  ACTTATTATA  TACAATATGG
3361  ATAAAAGATA  TATATCAACT  AGAAAGTTGA
3391  ATGACGGATT  CTTAATTTTA  TATTATGATT
3421  CAATAGAAAT  TATTGTCATG  TCGTGTAATC
2451  ATTTTATAAA  TATATCAGCG  TTACTAGCTA
3481  AGAAAACAA   GGACTTTAAT  GAATGGCTAA
3501  AGATAGAATC  ATTTAGAGAA  ATAATAGATA
3541  CTTTAGATAA  AATTAATTAC  GATCTAGGAC
3571  AACGATATTG  TGAAGAACTT  ACGGCGCATC
3601  ACATTCCAGT  GTAATTATTG  AGGTCAAAGC
3631  TAGTAACTTA  ATAGATGACA  GGACAGCTG
```

| FIG. 12A |
|----------|
| FIG. 12B |

```
   1   TGTCTGGACT  AACTGATTTC  ATGGAACAAT
  31   TTTCATCAAA  AATATCAGTT  ATACCTAGTT
  61   CTACAAAGAC  AGAACTTTGA  TGTTATGTTT
  91   GTGTTTGTAT  AGAAAATTTT  GGGATACTAA
 121   CTGATATTTC  TGAATATTTC  TGAATATTTC
 151   ATGTTACTTA  CTTACTCCTA  TCTTAGACGA
 181   TAATAAAATT  CGAGGCGTAA  TATGTTTTTC
 211   CAAATATTTG  AAATTCTTAT  ACGTATCGGC
 241   GAAGAAAAGT  AACATACTAT  AAGTGTTATG
 271   CAAGTAAGGT  ATGTTAATGA  TATTGGATTT
 301   AATTTCATTG  ACAATACATA  TGTCCAAACA
 331   TTCCACTCGT  AATTATGTAC  GGAACGACTT
 361   TAGTTAAATA  CTTAGTCACA  AAAAACTTAT
 391   GACTGTCATT  ATCTGAAAAC  GGTGATTCCC
 421   ATAAATCAGA  ATACTTAATA  TTAAATAGAA
 461   TGCTCGCTTC  TGGAGGTTTC  CGGATACTAG
 481   ATAACATATC  TTCTGTATTA  TAGTTTAATT
 511   CACTCATTTT  ATTACATAAT  ACAGTAACAT
 541   CTCCCGAAAC  CAATGATGTT  ATATTAGATT
 571   TACTTACATA  CTTCTTGTAA  CTATCATGAA
 601   TACGTTTGTT  ATGATCTATA  AAGAAGATGG
 631   ATGTATATTC  TGTTCTAGAT  AGCAAGTTCT
 661   TTAAGTTATT  CTTTGTCTGT  ATTACTATCA
 691   TCGTCTTCAT  CATCGTCTAA  AGGTAGCATT
 721   ATATAATAAA  TCTAATAGTT  GATTTCTCGA
 751   TCTATCAGTA  CTCGCTTTCA  ATAACATTTT
 781   TACTATAAGC  ATAATAGAAG  GCGGTGATAT
 811   CACTATATTT  TTATCGGGTA  TTCTTTTAGT
 841   AATTAGTTAG  TTCGTAGAAT  TTCGTAGAGA
 871   TAAAAGCCAA  TTTGTTGTTG  ATACTGCTTA
 901   CGTTACTCAT  GTTTCTTGTT  TCTGTTAATT
 931   AACAGGTATA  CCCTTACAAT  AAGTTTAATT
 961   AACTTTTAGG  TTTTTGTGAA  GAACTTTTAG
 991   CTTCTAGTTC  CCTTATCCAT  AATTGGGTCT
1021   TAGATCTAGA  TTCTTCCCAT  GTATAAAGGG
1051   GGACATACCC  AAAATCTTTA  AATGCTTTGT
1081   CCGTTTCTAT  AGTAAATGTC  GTACATTCCT
1111   TAATCAAAGT  ATAAGGATTT  AGTAAAGGCG
1141   TGTAAGAACA  AATAGGTGAT  AGTAATACTC
1171   TTAAACCTTT  ATTAATATTA  GCGATAAACC
1201   TTAAACACCA  TAAAGGAAGA  CATGTATTCC
1231   GTAGATCCAT  CCCTAATTGA  TTAAAGAAAT
1261   GCATGTTAAA  ATCATGATAA  TGTTCAGTAG
1291   GAGAGGTATC  GTAACAGTAA  TACACGTTAT
```

FIG. 12B

```
1321    TGCAGAGAGG    ACTATGTTGA    CCATTTTCTA
1351    TCATATTTCT    TGCTGCTAAA    ATATGCATCC
1381    AAGCTACGTT    TCCTGCATAG    ACTCTGCTAT
1411    GAAATACTTT    ATCATCCGCA    TATTTATACA
1441    TTTTCCTGCT    TTTATACGAT    CTTCTGTATA
1471    AAGTTTCTAG    TACTGGACAG    TATTCTCCGA
1501    AAACACCTAA    TGGGCGTAGC    GACAAGTGCA
1531    TAATCTAAGT    CCTATATTAG    ACATAGTACC
1561    GTTAGCTTCT    AGTATATATT    TCTCAGATAA
1591    CTTGTTTACT    AAGAGGATAA    GCCTCTTTAT
1621    GGTTAGATTG    ATAATACGTA    TTCTCGTTTC
1651    CTCTTATCAT    CGCATCTCCG    GAGAAAGTTA
1681    GGACCTACCG    CAGAATAACT    ACTCGTATAT
1711    ACTAAGACTC    TTACGCCGTT    ATACAGACAA
1741    GAATCTACTA    CGTTCTTCGT    TCCGTTGATA
1771    TTAACGTCCA    TTATAGAGTC    GTTAGTAAAC
1801    TTACCCGCTA    CATCATTTAT    CGAAGCAATA
1831    TGAATGACCA    CATCTGCTGA    TCTAAGCGCT
1861    TCGTCCAAAG    TACTTTTATT    TCTAACATCT
1891    CCAATCACGG    GAACTATCTT    TATTATATTA
1921    CATTTTCTA     CAAGATCTAG    TAACCATTGG
1951    TCGATTCTAA    TATCGTAAAC    ACGAACTTCT
1981    TTTTAAAGAG    GATTCGAACA    AGATAAGATT
2011    ATTTATAATG    TGTCTACCTA    AAAATCCACA
2041    CCCTCCGGTT    ACCACGTATA    CTAGTGTACG
2071    CATTTGAGT     ATTAACTATA    TAAGACCAAA
2101    ATTATATTTT    CATTTCTGT     TATATTATAC
2131    TATATAATAA    AAACAAATAA    ATATACGAAT
2161    ATTATAAGAA    ATTTAGAACA    CGTTATTAAA
2191    GTATTGCCTT    TTTTATTAAC    GGCGTGTTCT
2221    TGTAATTGCC    GTTAGAATA     GTCTTTATTT
2251    ACTTAGATA     ACTCTTCTAT    CATAACCGTC
2281    TCCTTATTCC    AATCTTCTTC    AGAAGTACAT
2311    GAGTACTTAC    CGAAGTTTAT    CATCATAGAG
2341    ATTATATATG    AAGAAA
```

```
  1 TTCTTTATTCTATACTTAAAAAGTGAAAATAAATACAAAGGTTCTTGAGG

51 GTTGTGTTAAATTGAAAGCGAGAAATAATCATAAATTATTTCATTATCGC

101 GATATCCGTTAAGTTTGTATCGTA ATG CTC CCC TAC CAA GAC
                             Met Leu Pro Tyr Gln Asp>

143 AAG GTG GGT GCC TTC TAC AAG GAT AAT GCA AGA GCC
    Lys Val Gly Ala Phe Tyr Lys Asp Asn Ala Arg Ala>

179 AAT TCA ACC AAG CTG TCC TTA GTG ACA GAA GGA CAT
    Asn Ser Thr Lys Leu Ser Leu Val Thr Glu Gly His>

215 GGG GGC AGG AGA CCA CCT TAT TTG TTG TTT GTC CTT
    Gly Gly Arg Arg Pro Pro Tyr Leu Leu Phe Val Leu>

251 CTC ATC TTA TTG GTT GGT ATC CTG GCC TTG CTT GCT
    Leu Ile Leu Leu Val Gly Ile Leu Ala Leu Leu Ala>

287 ATC ACT GGA GTT CGA TTT CAC CAA GTA TCA ACT AGT
    Ile Thr Gly Val Arg Phe His Gln Val Ser Thr Ser>

323 AAT ATG GAA TTT AGC AGA TTG CTG AAA GAG GAT ATG
    Asn Met Glu Phe Ser Arg Leu Leu Lys Glu Asp Met>

359 GAG AAA TCA GAG GCC GTA CAT CAC CAA GTC ATA GAT
    Glu Lys Ser Glu Ala Val His His Gln Val Ile Asp>

395 GTC TTG ACA CCG CTC TTC AAG ATT ATT GGA GAT GAG
    Val Leu Thr Pro Leu Phe Lys Ile Ile Gly Asp Glu>

431 ATT GGG TTA CGG TTG CCA CAA AAG CTA AAC GAG ATC
    Ile Gly Leu Arg Leu Pro Gln Lys Leu Asn Glu Ile>

467 AAA CAA TTT ATC CTT CAA AAG ACA AAT TTC TTC AAT
    Lys Gln Phe Ile Leu Gln Lys Thr Asn Phe Phe Asn>

503 CCG AAC AGA GAA TTC GAC TTC CGC GAT CTC CAC TGG
    Pro Asn Arg Glu Phe Asp Phe Arg Asp Leu His Trp>

539 TGC ATT AAC CCG CCT AGT ACG GTC AAG GTG AAT TTT
    Cys Ile Asn Pro Pro Ser Thr Val Lys Val Asn Phe>

575 ACT AAT TAC TGT GAG TCA ATT GGG ATC AGA AAA GCT
    Thr Asn Tyr Cys Glu Ser Ile Gly Ile Arg Lys Ala>

611 ATT GCA TCG GCA GCA AAT CCT ATC CTT TTA TCA GCC
    Ile Ala Ser Ala Ala Asn Pro Ile Leu Leu Ser Ala>
```

```
647  CTA TCT GGG GGC AGA GGT GAC ATA TTC CCA CCA CAC
     Leu Ser Gly Gly Arg Gly Asp Ile Phe Pro Pro His>

683  AGA TGC AGT GGA GCT ACT ACT TCA GTA GGC AAA GTT
     Arg Cys Ser Gly Ala Thr Thr Ser Val Gly Lys Val>

719  TTC CCC CTA TCA GTC TCA TTA TCC ATG TCT TTG ATC
     Phe Pro Leu Ser Val Ser Leu Ser Met Ser Leu Ile>

755  TCA AGA ACC TCA GAG GTA ATC AAT ATG CTG ACC GCT
     Ser Arg Thr Ser Glu Val Ile Asn Met Leu Thr Ala>

791  ATC TCA GAC GGC GTG TAT GGC AAA ACT TAC TTG CTA
     Ile Ser Asp Gly Val Tyr Gly Lys Thr Tyr Leu Leu>

827  GTG CCT GAT GAT ATA GAA AGA GAG TTC GAC ACT CGA
     Val Pro Asp Asp Ile Glu Arg Glu Phe Asp Thr Arg>

863  GAG ATT CGA GTC TTT GAA ATA GGG TTC ATC AAG AGG
     Glu Ile Arg Val Phe Glu Ile Gly Phe Ile Lys Arg>

899  TGG CTG AAT GAC ATG CCA TTA CTC CAA ACA ACC AAC
     Trp Leu Asn Asp Met Pro Leu Leu Gln Thr Thr Asn>

935  TAT ATG GTA CTC CCG AAG AAT TCC AAA GCC AAG GTA
     Tyr Met Val Leu Pro Lys Asn Ser Lys Ala Lys Val>

971  TGT ACT ATA GCA GTG GGT GAG TTG ACA CTG GCT TCC
     Cys Thr Ile Ala Val Gly Glu Leu Thr Leu Ala Ser>

1007 TTG TGT GTA GAA GAG AGC ACT GTA TTA TTA TAT CAT
     Leu Cys Val Glu Glu Ser Thr Val Leu Leu Tyr His>

1043 GAC AGC AGT GGT TCA CAA GAT GGT ATT CTA GTA GTG
     Asp Ser Ser Gly Ser Gln Asp Gly Ile Leu Val Val>

1079 ACA CTG GGG ATA TTT TGG GCA ACA CCT ATG GAT CAC
     Thr Leu Gly Ile Phe Trp Ala Thr Pro Met Asp His>

1115 ATT GAG GAA GTG ATA CCT GTC GCT CAC CCA TCA ATG
     Ile Glu Glu Val Ile Pro Val Ala His Pro Ser Met>

1151 AAG AAA ATA CAT ATA ACA AAC CAC CGT GGT TTT ATA
     Lys Lys Ile His Ile Thr Asn His Arg Gly Phe Ile>

1187 AAA GAT TCA ATT GCA ACC TGG ATG GTG CCT GCC CTG
     Lys Asp Ser Ile Ala Thr Trp Met Val Pro Ala Leu>

1223 GCC TCT GAG AAA CAA GAA GAA CAA AAA GGT TGT CTG
     Ala Ser Glu Lys Gln Glu Glu Gln Lys Gly Cys Leu>
```

*FIG. 14B*

```
1259 GAG TCA GCT TGT CAA AGA AAA ACC TAC CCC ATG TGC
     Glu Ser Ala Cys Gln Arg Lys Thr Tyr Pro Met Cys>

1295 AAC CAA GCG TCA TGG GAA CCC TTC GGA GGA AGA CAG
     Asn Gln Ala Ser Trp Glu Pro Phe Gly Gly Arg Gln>

1331 TTG CCA TCT TAT GGG CGG TTG ACA TTA CCT CTA GAT
     Leu Pro Ser Tyr Gly Arg Leu Thr Leu Pro Leu Asp>

1367 GCA AGT GTT GAC CTT CAA CTT AAC ATA TCG TTC ACA
     Ala Ser Val Asp Leu Gln Leu Asn Ile Ser Phe Thr>

1403 TAC GGT CCG GTT ATA CTG AAT GGA GAT GGT ATG GAT
     Tyr Gly Pro Val Ile Leu Asn Gly Asp Gly Met Asp>

1439 TAT TAT GAA AGC CCA CTT TTG AAC TCC GGA TGG CTT
     Tyr Tyr Glu Ser Pro Leu Leu Asn Ser Gly Trp Leu>

1475 ACC ATT CCC CCC AAA GAC GGA ACA ATC TCT GGA TTG
     Thr Ile Pro Pro Lys Asp Gly Thr Ile Ser Gly Leu>

1511 ATA AAC AAA GCA GGT AGA GGA GAC CAG TTC ACT GTA
     Ile Asn Lys Ala Gly Arg Gly Asp Gln Phe Thr Val>

1547 CTC CCC CAT GTG TTA ACA TTT GCG CCC AGG GAA TCA
     Leu Pro His Val Leu Thr Phe Ala Pro Arg Glu Ser>

1583 AGT GGA AAT TGT TAT TTA CCT ATT CAA ACA TCT CAA
     Ser Gly Asn Cys Tyr Leu Pro Ile Gln Thr Ser Gln>

1619 ATT AGA GAT AGA GAT GTC CTC ATT GAG TCC AAT ATA
     Ile Arg Asp Arg Asp Val Leu Ile Glu Ser Asn Ile>

1655 GTG GTG TTG CCT ACA CAG AGT ATT AGA TAT GTC ATA
     Val Val Leu Pro Thr Gln Ser Ile Arg Tyr Val Ile>

1691 GCA ACG TAT GAC ATA TCA CGA AGT GAT CAT GCT ATT
     Ala Thr Tyr Asp Ile Ser Arg Ser Asp His Ala Ile>

1727 GTT TAT TAT GTT TAT GAC CCA ATC CGG ACG ATT TCT
     Val Tyr Tyr Val Tyr Asp Pro Ile Arg Thr Ile Ser>

1763 TAT ACG CAC CCA TTT AGA CTA ACT ACC AAG GGT AGA
     Tyr Thr His Pro Phe Arg Leu Thr Thr Lys Gly Arg>

1799 CCT GAT TTC CTA AGG ATT GAA TGT TTT GTG TGG GAT
     Pro Asp Phe Leu Arg Ile Glu Cys Phe Val Trp Asp>

1835 GAC AAT TTG TGG TGT CAC CAA TTT TAC AGA TTC GAG
     Asp Asn Leu Trp Cys His Gln Phe Tyr Arg Phe Glu>
```

FIG. 14C

```
1871 GCT GAC ATC GCC AAC TCT ACA ACC AGT GTT GAG AAT
     Ala Asp Ile Ala Asn Ser Thr Thr Ser Val Glu Asn>

1907 TTA GTC CGT ATA AGA TTC TCA TGT AAC CGT TAA
     Leu Val Arg Ile Arg Phe Ser Cys Asn Arg End>
```

```
  1 TTCTTTATTCTATACTTAAAAAGTGAAAATAAATACAAAGGTTCTTGAGG

51 GTTGTGTTAAATTGAAAGCGAGAAATAATCATAAATTATTTCATTATCGC

101 GATATCCGTTAAGTTTGTATCGTA ATG CAC AAG GGA ATC CCC
                             Met His Lys Gly Ile Pro>

143 AAA AGC TCC AAA ACC CAA ACA CAT ACC CAA CAA GAC
    Lys Ser Ser Lys Thr Gln Thr His Thr Gln Gln Asp>

179 CGC CCC CCA CAA CCC AGC ACC GAA CTC GAA GAG ACC
    Arg Pro Pro Gln Pro Ser Thr Glu Leu Glu Glu Thr>

215 AGG ACC TCC CGA GCA CGA CAC AGC ACA ACA TCA GCT
    Arg Thr Ser Arg Ala Arg His Ser Thr Thr Ser Ala>

251 CAG CGA TCC ACG CAC TAC GAT CCT CGA ACA TCG GAC
    Gln Arg Ser Thr His Tyr Asp Pro Arg Thr Ser Asp>

287 AGA CCC GTC TCC TAC ACC ATG AAC AGG ACC AGG TCC
    Arg Pro Val Ser Tyr Thr Met Asn Arg Thr Arg Ser>

323 CGC AAG CAA ACC AGC CAC AGA TTG AAG AAC ATC CCA
    Arg Lys Gln Thr Ser His Arg Leu Lys Asn Ile Pro>

359 GTT CAC GGA AAC CAC GAG GCC ACC ATC CAG CAC ATA
    Val His Gly Asn His Glu Ala Thr Ile Gln His Ile>

395 CCA GAG AGT GTC TCA AAA GGA GCG AGA TCC CAG ATC
    Pro Glu Ser Val Ser Lys Gly Ala Arg Ser Gln Ile>

431 GAA AGG CGG CAA CCC AAT GCA ATC AAC TCA GGC TCT
    Glu Arg Arg Gln Pro Asn Ala Ile Asn Ser Gly Ser>

467 CAT TGC ACC TGG TTA GTC CTG TGG TGC CTC GGA ATG
    His Cys Thr Trp Leu Val Leu Trp Cys Leu Gly Met>

503 GCC AGT CTC TTT CTT TGT TCC AAG GCT CAG ATA CAT
    Ala Ser Leu Phe Leu Cys Ser Lys Ala Gln Ile His>

539 TGG AAT AAT TTG TCA ACT ATT GGG ATT ATC GGG ACT
    Trp Asn Asn Leu Ser Thr Ile Gly Ile Ile Gly Thr>

575 GAT AGT GTC CAT TAC AAG ATC ATG ACT AGG CCC AGT
    Asp Ser Val His Tyr Lys Ile Met Thr Arg Pro Ser>

611 CAC CAG TAC TTG GTC ATA AAA CTG ATG CCT AAT GTT
    His Gln Tyr Leu Val Ile Lys Leu Met Pro Asn Val>
```

```
 647 TCA CTT ATA GAG AAT TGT ACC AAA GCA GAA TTA GGT
     Ser Leu Ile Glu Asn Cys Thr Lys Ala Glu Leu Gly>

683 GAG TAT GAG AAA TTA TTG AAT TCA GTC CTC GAA CCA
     Glu Tyr Glu Lys Leu Leu Asn Ser Val Leu Glu Pro>

719 ATC AAC CAA GCT TTG ACT CTA ATG ACC AAG AAT GTG
     Ile Asn Gln Ala Leu Thr Leu Met Thr Lys Asn Val>

755 AAG CCC CTG CAG TCA TTA GGG TCA GGT AGG AGA CAA
     Lys Pro Leu Gln Ser Leu Gly Ser Gly Arg Arg Gln>

791 AGG CGT TTT GCA GGA GTG GTA CTT GCA GGT GTA GCT
     Arg Arg Phe Ala Gly Val Val Leu Ala Gly Val Ala>

827 TTA GGA GTG GCT ACA GCT GCA CAA ATC ACT GCA GGA
     Leu Gly Val Ala Thr Ala Ala Gln Ile Thr Ala Gly>

863 ATA GCT TTA CAT CAA TCC AAC CTC AAT GCT CAA GCA
     Ile Ala Leu His Gln Ser Asn Leu Asn Ala Gln Ala>

899 ATC CAA TCT CTT AGA ACC AGC CTT GAA CAG TCT AAC
     Ile Gln Ser Leu Arg Thr Ser Leu Glu Gln Ser Asn>

935 AAA GCT ATA GAA GAA ATT AGG GAG GCT ACC CAA GAA
     Lys Ala Ile Glu Glu Ile Arg Glu Ala Thr Gln Glu>

971 ACC GTC ATT GCC GTT CAG GGA GTC CAG GAC TAC GTC
     Thr Val Ile Ala Val Gln Gly Val Gln Asp Tyr Val>

1007 AAC AAC GAA CTC GTC CCT GCC ATG CAA CAT ATG TCA
     Asn Asn Glu Leu Val Pro Ala Met Gln His Met Ser>

1043 TGT GAA TTA GTT GGG CAG AGA TTA GGG TTA AGA CTG
     Cys Glu Leu Val Gly Gln Arg Leu Gly Leu Arg Leu>

1079 CTT CGG TAT TAT ACT GAG TTG TTG TCA ATA TTT GGC
     Leu Arg Tyr Tyr Thr Glu Leu Leu Ser Ile Phe Gly>

1115 CCG AGT TTA CGT GAC CCT ATT TCA GCC GAG ATA TCA
     Pro Ser Leu Arg Asp Pro Ile Ser Ala Glu Ile Ser>

1151 ATT CAG GCA CTG ATT TAT GCT CTT GGA GGA GAA ATT
     Ile Gln Ala Leu Ile Tyr Ala Leu Gly Gly Glu Ile>

1187 CAT AAG ATA CTT GGG AAG TTG GGA TAT TCT GGA AGT
     His Lys Ile Leu Gly Lys Leu Gly Tyr Ser Gly Ser>

1223 GAT ATG ATT GCA ATC TTG GAG AGT CGG GGG ATA AAA
     Asp Met Ile Ala Ile Leu Glu Ser Arg Gly Ile Lys>
```

*FIG. 15B*

```
1259 ACA AAA ATA ACT CAT GTT GAT CTT CCC GGG AAA TTC
     Thr Lys Ile Thr His Val Asp Leu Pro Gly Lys Phe>

1295 ATC ATC CTA AGT ATC TCA TAC CCA ACT TTA TCA GAA
     Ile Ile Leu Ser Ile Ser Tyr Pro Thr Leu Ser Glu>

1331 GTC AAG GGG GTT ATA GTC CAC AGA CTG GAA GCG GTT
     Val Lys Gly Val Ile Val His Arg Leu Glu Ala Val>

1367 TCT TAC AAC ATA GGA TCA CAA GAG TGG TAC ACC ACT
     Ser Tyr Asn Ile Gly Ser Gln Glu Trp Tyr Thr Thr>

1403 GTC CCG AGG TAT ATT GCA ACT AAT GGT TAC TTA ATA
     Val Pro Arg Tyr Ile Ala Thr Asn Gly Tyr Leu Ile>

1439 TCT AAT TTT GAT GAG TCA TCT TGT GTA TTC GTC TCA
     Ser Asn Phe Asp Glu Ser Ser Cys Val Phe Val Ser>

1475 GAG TCA GCC ATT TGT AGC CAG AAC TCC CTG TAT CCC
     Glu Ser Ala Ile Cys Ser Gln Asn Ser Leu Tyr Pro>

1511 ATG AGC CCA CTC TTA CAA CAA TGT ATT AGG GGC GAC
     Met Ser Pro Leu Leu Gln Gln Cys Ile Arg Gly Asp>

1547 ACT TCA TCT TGT GCT CGG ACC TTG GTA TCT GGG ACT
     Thr Ser Ser Cys Ala Arg Thr Leu Val Ser Gly Thr>

1583 ATG GGC AAC AAA TTT ATT CTG TCA AAA GGT AAT ATC
     Met Gly Asn Lys Phe Ile Leu Ser Lys Gly Asn Ile>

1619 GTC GCA AAT TGT GCT TCT ATA CTA TGT AAG TGT TAT
     Val Ala Asn Cys Ala Ser Ile Leu Cys Lys Cys Tyr>

1655 AGC ACA AGC ACA ATT ATT AAT CAG AGT CCT GAT AAG
     Ser Thr Ser Thr Ile Ile Asn Gln Ser Pro Asp Lys>

1691 TTG CTG ACA TTC ATT GCC TCC GAT ACC TGC CCA CTG
     Leu Leu Thr Phe Ile Ala Ser Asp Thr Cys Pro Leu>

1727 GTT GAA ATA GAT GGT GCT ACT ATC CAA GTT GGA GGC
     Val Glu Ile Asp Gly Ala Thr Ile Gln Val Gly Gly>

1763 AGG CAA TAC CCT GAT ATG GTA TAC GAA GGC AAA GTT
     Arg Gln Tyr Pro Asp Met Val Tyr Glu Gly Lys Val>

1799 GCC TTA GGC CCT GCT ATA TCA CTT GAT AGG TTA GAT
     Ala Leu Gly Pro Ala Ile Ser Leu Asp Arg Leu Asp>

1835 GTA GGT ACA AAC TTA GGG AAC GCC CTT AAG AAA CTG
     Val Gly Thr Asn Leu Gly Asn Ala Leu Lys Lys Leu>
```

FIG. 15C

```
1871  GAT  GAT  GCT  AAG  GTA  CTG  ATA  GAC  TCC  TCT  AAC  CAG
      Asp  Asp  Ala  Lys  Val  Leu  Ile  Asp  Ser  Ser  Asn  Gln>

1907  ATC  CTT  GAG  ACG  GTT  AGG  CGC  TCT  TCC  TTC  AAT  TTT
      Ile  Leu  Glu  Thr  Val  Arg  Arg  Ser  Ser  Phe  Asn  Phe>

1943  GGC  AGT  CTC  CTC  AGC  GTT  CCT  ATA  TTA  AGT  TGT  ACA
      Gly  Ser  Leu  Leu  Ser  Val  Pro  Ile  Leu  Ser  Cys  Thr>

1979  GCC  CTG  GCT  TTG  TTG  TTG  CTG  ATT  TAC  TGT  TGT  AAA
      Ala  Leu  Ala  Leu  Leu  Leu  Leu  Ile  Tyr  Cys  Cys  Lys>

2015  AGA  CGC  TAC  CAA  CAG  ACA  CTC  AAG  CAG  CAT  ACT  AAG
      Arg  Arg  Tyr  Gln  Gln  Thr  Leu  Lys  Gln  His  Thr  Lys>

2051  GTC  GAT  CCG  GCA  TTT  AAA  CCT  GAT  CTA  ACT  GGA  ACT
      Val  Asp  Pro  Ala  Phe  Lys  Pro  Asp  Leu  Thr  Gly  Thr>

2087  TCG  AAA  TCC  TAT  GTG  AGA  TCA  CAC  TGA
      Ser  Lys  Ser  Tyr  Val  Arg  Ser  His  End>
```

```
  1 TTTGTAATATAATGATATATATTTTCACTTTATCTCATTTGAGAATAAAA

51 AGATCACAAAAATTAACTAATCAGGATCCATAAAAATCA GTG TGA
                                            <His Ser

96 TCT CAC ATA GGA TTT CGA AGT TCC AGT TAG ATC AGG
    <Arg Val Tyr Ser Lys Ser Thr Gly Thr Leu Asp Pro

132 TTT AAA TGC CGG ATC GAC CTT AGT ATG CTG CTT GAG
    <Lys Phe Ala Pro Asp Val Lys Thr His Gln Lys Leu

168 TGT CTG TTG GTA GCG TCT TTT ACA ACA GTA AAT CAG
    <Thr Gln Gln Tyr Arg Arg Lys Cys Cys Tyr Ile Leu

204 CAA CAA CAA AGC CAG GGC TGT ACA ACT TAA TAT AGG
    <Leu Leu Leu Ala Leu Ala Thr Cys Ser Leu Ile Pro

240 AAC GCT GAG GAG ACT GCC AAA ATT GAA GGA AGA GCG
    <Val Ser Leu Leu Ser Gly Phe Asn Phe Ser Ser Arg

276 CCT AAC CGT CTC AAG GAT CTG GTT AGA GGA GTC TAT
    <Arg Val Thr Glu Leu Ile Gln Asn Ser Ser Asp Ile

312 CAG TAC CTT AGC ATC ATC CAG TTT CTT AAG GGC GTT
    <Leu Val Lys Ala Asp Asp Leu Lys Lys Leu Ala Asn

348 CCC TAA GTT TGT ACC TAC ATC TAA CCT ATC AAG TGA
    <Gly Leu Asn Thr Gly Val Asp Leu Arg Asp Leu Ser

384 TAT AGC AGG GCC TAA GGC AAC TTT GCC TTC GTA TAC
    <Ile Ala Pro Gly Leu Ala Val Lys Gly Glu Tyr Val

420 CAT ATC AGG GTA TTG CCT GCC TCC AAC TTG GAT AGT
    <Met Asp Pro Tyr Gln Arg Gly Gly Val Gln Ile Thr

456 AGC ACC ATC TAT TTC AAC CAG TGG GCA GGT ATC GGA
    <Ala Gly Asp Ile Glu Val Leu Pro Cys Thr Asp Ser

492 GGC AAT GAA TGT CAG CAA CTT ATC AGG ACT CTG ATT
    <Ala Ile Phe Thr Leu Leu Lys Asp Pro Ser Gln Asn

528 AAT AAT TGT GCT TGT GCT ATA ACA CTT ACA TAG TAT
    <Ile Ile Thr Ser Thr Ser Tyr Cys Lys Cys Leu Ile

564 AGA AGC ACA ATT TGC GAC GAT ATT ACC TTT TGA CAG
    <Ser Ala Cys Asn Ala Val Ile Asn Gly Lys Ser Leu

600 AAT AAA TTT GTT GCC CAT AGT CCC AGA TAC CAA GGT
    <Ile Phe Lys Asn Gly Met Thr Gly Ser Val Leu Thr
```

```
 636 CCG AGC ACA AGA TGA AGT GTC GCC CCT AAT ACA TTG
     <Arg Ala Cys Ser Ser Thr Asp Gly Arg Ile Cys Gln

672 TTG TAA GAG TGG GCT CAT GGG ATA CAG GGA GTT CTG
     <Gln Leu Leu Pro Ser Met Pro Tyr Leu Ser Asn Gln

708 GCT ACA AAT GGC TGA CTC TGA GAC GAA TAC ACA AGA
     <Ser Cys Ile Ala Ser Glu Ser Val Phe Val Cys Ser

744 TGA CTC ATC AAA ATT AGA TAT TAA GTA ACC ATT AGT
     <Ser Glu Asp Phe Asn Ser Ile Leu Tyr Gly Asn Thr

780 TGC AAT ATA CCT CGG GAC AGT GGT GTA CCA CTC TTG
     <Ala Ile Tyr Arg Pro Val Thr Thr Tyr Trp Glu Gln

816 TGA TCC TAT GTT GTA AGA AAC CGC TTC CAG TCT GTG
     <Ser Gly Ile Asn Tyr Ser Val Ala Glu Leu Arg His

852 GAC TAT AAC CCC CTT GAC TTC TGA TAA AGT TGG GTA
     <Val Ile Val Gly Lys Val Glu Ser Leu Thr Pro Tyr

888 TGA GAT ACT TAG GAT GAT GAA TTT CCC GGG AAG ATC
     <Ser Ile Ser Leu Ile Ile Phe Lys Gly Pro Leu Asp

924 AAC ATG AGT TAT TTT TGT TTT TAT CCC CCG ACT CTC
     <Val His Thr Ile Lys Thr Lys Ile Gly Arg Ser Glu

960 CAA GAT TGC AAT CAT ATC ACT TCC AGA ATA TCC CAA
     <Leu Ile Ala Ile Met Asp Ser Gly Ser Tyr Gly Leu

996 CTT CCC AAG TAT CTT ATG AAT TTC TCC TCC AAG AGC
     <Lys Gly Leu Ile Lys His Ile Glu Gly Gly Leu Ala

1032 ATA AAT CAG TGC CTG AAT TGA TAT CTC GGC TGA AAT
     <Tyr Ile Leu Ala Gln Ile Ser Ile Glu Ala Ser Ile

1068 AGG GTC ACG TAA ACT CGG GCC AAA TAT TGA CAA CAA
     <Pro Asp Arg Leu Ser Pro Gly Phe Ile Ser Leu Leu

1104 CTC AGT ATA ATA CCG AAG CAG TCT TAA CCC TAA TCT
     <Glu Thr Tyr Tyr Arg Leu Leu Arg Leu Gly Leu Arg

1140 CTG CCC AAC TAA TTC ACA TGA CAT ATG TTG CAT GGC
     <Gln Gly Val Leu Glu Cys Ser Met His Gln Met Ala

1176 AGG GAC GAG TTC GTT GTT GAC GTA GTC CTG GAC TCC
     <Pro Val Leu Glu Asn Asn Val Tyr Asp Gln Val Gly

1212 CTG AAC GGC AAT GAC GGT TTC TTG GGT AGC CTC CCT
     <Gln Val Ala Ile Val Thr Glu Gln Thr Ala Glu Arg
```

FIG. 16B

```
1248 AAT TTC TTC TAT AGC TTT GTT AGA CTG TTC AAG GCT
    <Ile Glu Glu Ile Ala Lys Asn Ser Gln Glu Leu Ser

1284 GGT TCT AAG AGA TTG GAT TGC TTG AGC ATT GAG GTT
    <Thr Arg Leu Ser Gln Ile Ala Gln Ala Asn Leu Asn

1320 GGA TTG ATG TAA AGC TAT TCC TGC AGT GAT TTG TGC
    <Ser Gln His Leu Ala Ile Gly Ala Thr Ile Gln Ala

1356 AGC TGT AGC CAC TCC TAA AGC TAC ACC TGC AAG TAC
    <Ala Thr Ala Val Gly Leu Ala Val Gly Ala Leu Val

1392 CAC TCC TGC AAA ACG CCT TTG TCT CCT ACC TGA CCC
    <Val Gly Ala Phe Arg Arg Gln Arg Arg Gly Ser Gly

1428 TAA TGA CTG CAG GGG CTT CAC ATT CTT GGT CAT TAG
    <Leu Ser Gln Leu Pro Lys Val Asn Lys Thr Met Leu

1464 AGT CAA AGC TTG GTT GAT TGG TTC GAG GAC TGA ATT
    <Thr Leu Ala Gln Asn Ile Pro Glu Leu Val Ser Asn

1500 CAA TAA TTT CTC ATA CTC ACC TAA TTC TGC TTT GGT
    <Leu Leu Lys Glu Tyr Glu Gly Leu Glu Ala Lys Thr

1536 ACA ATT CTC TAT AAG TGA AAC ATT AGG CAT CAG TTT
    <Cys Asn Glu Ile Leu Ser Val Asn Pro Met Leu Lys

1572 TAT GAC CAA GTA CTG GTG ACT GGG CCT AGT CAT GAT
    <Ile Val Leu Tyr Gln His Ser Pro Arg Thr Met Ile

1608 CTT GTA ATG GAC ACT ATC AGT CCC GAT AAT CCC AAT
    <Lys Tyr His Val Ser Asp Thr Gly Ile Ile Gly Ile

1644 AGT TGA CAA ATT ATT CCA ATG TAT CTG AGC CTT GGA
    <Thr Ser Leu Asn Asn Trp His Ile Gln Ala Lys Ser

1680 ACA AAG AAA GAG ACT GGC CAT TCC GAG GCA CCA CAG
    <Cys Leu Phe Leu Ser Ala Met Gly Leu Cys Trp Leu

1716 GAC TAA CCA GGT GCA ATG AGA GCC TGA GTT GAT TGC
    <Val Leu Trp Thr Cys His Ser Gly Ser Asn Ile Ala

1752 ATT GGG TTG CCG CCT TTC GAT CTG GGA TCT CGC TCC
    <Asn Pro Gln Arg Arg Glu Ile Gln Ser Arg Ala Gly

1788 TTT TGA GAC ACT CTC TGG TAT GTG CTG GAT GGT GGC
    <Lys Ser Val Ser Glu Pro Ile His Gln Ile Thr Ala

1824 CTC GTG GTT TCC GTG AAC TGG GAT GTT CTT CAA TCT
    <Glu His Asn Gly His Val Pro Ile Asn Lys Leu Arg
```

FIG. 16C

```
1860 GTG GCT GGT TTG CTT GCG GGA CCT GGT CCT GTT CAT
    <His Ser Thr Gln Lys Arg Ser Arg Thr Arg Asn Met

1896 GGT GTA GGA GAC GGG TCT GTC CGA TGT TCG AGG ATC
    <Thr Tyr Ser Val Pro Arg Asp Ser Thr Arg Pro Asp

1932 GTA GTG CGT GGA TCG CTG AGC TGA TGT TGT GCT GTG
    <Tyr His Thr Ser Arg Gln Ala Ser Thr Thr Ser His

1968 TCG TGC TCG GGA GGT CCT GGT CTC TTC GAG TTC GGT
    <Arg Ala Arg Ser Thr Arg Thr Glu Glu Leu Glu Thr

2004 GCT GGG TTG TGG GGG GCG GTC TTG TTG GGT ATG TGT
    <Ser Pro Gln Pro Pro Arg Asp Gln Gln Thr His Thr

2040 TTG GGT TTT GGA GCT TTT GGG GAT TCC CTT GTG CAT
    <Gln Thr Lys Ser Ser Lys Pro Ile Gly Lys His Met

2076 TAC GAT ACA AAC TTAACGGATATCGCGATAATGAAATAATTTATGA

2122 TTATTTCTCGCTTTCAATTTAACACAACCCTCAAGAACCTTTGTATTTAT

2172 TTTCACTTTTTAAGTATAGAATAAAGAAGCTCTAATTAATTAAGCTACAA

2222 ATAGTTTCGTTTTCACCTTGTCTAATAACTAATTAATTAACCCGGATCCG

2272 GTACCCTCGAGCCCGGGTTAATTAATTAGTCATCAGGCAGGGCGAGAACG

2322 AGACTATCTGCTCGTTAATTAATTAGAGCTTGATTCTTTATTCTATACTT

2372 AAAAGTGAAAATAAATACAAGGTTCTTGAGGGTTGTGTTAAATTGAAA

2422 GCGAGAAATAATCATAAATTATTTCATTATCGCGATATCCGTTAA GTT

2470 TGT ATC GTA ATG CTC CCC TAC CAA GAC AAG GTG GGT
              Met Leu Pro Tyr Gln Asp Lys Val Gly>

2506 GCC TTC TAC AAG GAT AAT GCA AGA GCC AAT TCA ACC
    Ala Phe Tyr Lys Asp Asn Ala Arg Ala Asn Ser Thr>

2542 AAG CTG TCC TTA GTG ACA GAA GGA CAT GGG GGC AGG
    Lys Leu Ser Leu Val Thr Glu Gly His Gly Gly Arg>

2578 AGA CCA CCT TAT TTG TTG TTT GTC CTT CTC ATC TTA
    Arg Pro Pro Tyr Leu Leu Phe Val Leu Leu Ile Leu>

2614 TTG GTT GGT ATC CTG GCC TTG CTT GCT ATC ACT GGA
    Leu Val Gly Ile Leu Ala Leu Leu Ala Ile Thr Gly>
```

FIG.16D

```
2650 GTT CGA TTT CAC CAA GTA TCA ACT AGT AAT ATG GAA
     Val Arg Phe His Gln Val Ser Thr Ser Asn Met Glu>

2686 TTT AGC AGA TTG CTG AAA GAG GAT ATG GAG AAA TCA
     Phe Ser Arg Leu Leu Lys Glu Asp Met Glu Lys Ser>

2722 GAG GCC GTA CAT CAC CAA GTC ATA GAT GTC TTG ACA
     Glu Ala Val His His Gln Val Ile Asp Val Leu Thr>

2758 CCG CTC TTC AAG ATT ATT GGA GAT GAG ATT GGG TTA
     Pro Leu Phe Lys Ile Ile Gly Asp Glu Ile Gly Leu>

2794 CGG TTG CCA CAA AAG CTA AAC GAG ATC AAA CAA TTT
     Arg Leu Pro Gln Lys Leu Asn Glu Ile Lys Gln Phe>

2830 ATC CTT CAA AAG ACA AAT TTC TTC AAT CCG AAC AGA
     Ile Leu Gln Lys Thr Asn Phe Phe Asn Pro Asn Arg>

2866 GAA TTC GAC TTC CGC GAT CTC CAC TGG TGC ATT AAC
     Glu Phe Asp Phe Arg Asp Leu His Trp Cys Ile Asn>

2902 CCG CCT AGT ACG GTC AAG GTG AAT TTT ACT AAT TAC
     Pro Pro Ser Thr Val Lys Val Asn Phe Thr Asn Tyr>

2938 TGT GAG TCA ATT GGG ATC AGA AAA GCT ATT GCA TCG
     Cys Glu Ser Ile Gly Ile Arg Lys Ala Ile Ala Ser>

2974 GCA GCA AAT CCT ATC CTT TTA TCA GCC CTA TCT GGG
     Ala Ala Asn Pro Ile Leu Leu Ser Ala Leu Ser Gly>

3010 GGC AGA GGT GAC ATA TTC CCA CCA CAC AGA TGC AGT
     Gly Arg Gly Asp Ile Phe Pro Pro His Arg Cys Ser>

3046 GGA GCT ACT ACT TCA GTA GGC AAA GTT TTC CCC CTA
     Gly Ala Thr Thr Ser Val Gly Lys Val Phe Pro Leu>

3082 TCA GTC TCA TTA TCC ATG TCT TTG ATC TCA AGA ACC
     Ser Val Ser Leu Ser Met Ser Leu Ile Ser Arg Thr>

3118 TCA GAG GTA ATC AAT ATG CTG ACC GCT ATC TCA GAC
     Ser Glu Val Ile Asn Met Leu Thr Ala Ile Ser Asp>

3154 GGC GTG TAT GGC AAA ACT TAC TTG CTA GTG CCT GAT
     Gly Val Tyr Gly Lys Thr Tyr Leu Leu Val Pro Asp>

3190 GAT ATA GAA AGA GAG TTC GAC ACT CGA GAG ATT CGA
     Asp Ile Glu Arg Glu Phe Asp Thr Arg Glu Ile Arg>

3226 GTC TTT GAA ATA GGG TTC ATC AAG AGG TGG CTG AAT
     Val Phe Glu Ile Gly Phe Ile Lys Arg Trp Leu Asn>
```

FIG. 16E

```
3262 GAC ATG CCA TTA CTC CAA ACA ACC AAC TAT ATG GTA
     Asp Met Pro Leu Leu Gln Thr Thr Asn Tyr Met Val>

3298 CTC CCG AAG AAT TCC AAA GCC AAG GTA TGT ACT ATA
     Leu Pro Lys Asn Ser Lys Ala Lys Val Cys Thr Ile>

3334 GCA GTG GGT GAG TTG ACA CTG GCT TCC TTG TGT GTA
     Ala Val Gly Glu Leu Thr Leu Ala Ser Leu Cys Val>

3370 GAA GAG AGC ACT GTA TTA TTA TAT CAT GAC AGC AGT
     Glu Glu Ser Thr Val Leu Leu Tyr His Asp Ser Ser>

3406 GGT TCA CAA GAT GGT ATT CTA GTA GTG ACA CTG GGG
     Gly Ser Gln Asp Gly Ile Leu Val Val Thr Leu Gly>

3442 ATA TTT TGG GCA ACA CCT ATG GAT CAC ATT GAG GAA
     Ile Phe Trp Ala Thr Pro Met Asp His Ile Glu Glu>

3478 GTG ATA CCT GTC GCT CAC CCA TCA ATG AAG AAA ATA
     Val Ile Pro Val Ala His Pro Ser Met Lys Lys Ile>

3514 CAT ATA ACA AAC CAC CGT GGT TTT ATA AAA GAT TCA
     His Ile Thr Asn His Arg Gly Phe Ile Lys Asp Ser>

3550 ATT GCA ACC TGG ATG GTG CCT GCC CTG GCC TCT GAG
     Ile Ala Thr Trp Met Val Pro Ala Leu Ala Ser Glu>

3586 AAA CAA GAA GAA CAA AAA GGT TGT CTG GAG TCA GCT
     Lys Gln Glu Glu Gln Lys Gly Cys Leu Glu Ser Ala>

3622 TGT CAA AGA AAA ACC TAC CCC ATG TGC AAC CAA GCG
     Cys Gln Arg Lys Thr Tyr Pro Met Cys Asn Gln Ala>

3658 TCA TGG GAA CCC TTC GGA GGA AGA CAG TTG CCA TCT
     Ser Trp Glu Pro Phe Gly Gly Arg Gln Leu Pro Ser>

3694 TAT GGG CGG TTG ACA TTA CCT CTA GAT GCA AGT GTT
     Tyr Gly Arg Leu Thr Leu Pro Leu Asp Ala Ser Val>

3730 GAC CTT CAA CTT AAC ATA TCG TTC ACA TAC GGT CCG
     Asp Leu Gln Leu Asn Ile Ser Phe Thr Tyr Gly Pro>

3766 GTT ATA CTG AAT GGA GAT GGT ATG GAT TAT TAT GAA
     Val Ile Leu Asn Gly Asp Gly Met Asp Tyr Tyr Glu>

3802 AGC CCA CTT TTG AAC TCC GGA TGG CTT ACC ATT CCC
     Ser Pro Leu Leu Asn Ser Gly Trp Leu Thr Ile Pro>

3838 CCC AAA GAC GGA ACA ATC TCT GGA TTG ATA AAC AAA
     Pro Lys Asp Gly Thr Ile Ser Gly Leu Ile Asn Lys>
```

FIG. 16F

```
3874 GCA GGT AGA GGA GAC CAG TTC ACT GTA CTC CCC CAT
     Ala Gly Arg Gly Asp Gln Phe Thr Val Leu Pro His>

3910 GTG TTA ACA TTT GCG CCC AGG GAA TCA AGT GGA AAT
     Val Leu Thr Phe Ala Pro Arg Glu Ser Ser Gly Asn>

3946 TGT TAT TTA CCT ATT CAA ACA TCT CAA ATT AGA GAT
     Cys Tyr Leu Pro Ile Gln Thr Ser Gln Ile Arg Asp>

3982 AGA GAT GTC CTC ATT GAG TCC AAT ATA GTG GTG TTG
     Arg Asp Val Leu Ile Glu Ser Asn Ile Val Val Leu>

4018 CCT ACA CAG AGT ATT AGA TAT GTC ATA GCA ACG TAT
     Pro Thr Gln Ser Ile Arg Tyr Val Ile Ala Thr Tyr>

4054 GAC ATA TCA CGA AGT GAT CAT GCT ATT GTT TAT TAT
     Asp Ile Ser Arg Ser Asp His Ala Ile Val Tyr Tyr>

4090 GTT TAT GAC CCA ATC CGG ACG ATT TCT TAT ACG CAC
     Val Tyr Asp Pro Ile Arg Thr Ile Ser Tyr Thr His>

4126 CCA TTT AGA CTA ACT ACC AAG GGT AGA CCT GAT TTC
     Pro Phe Arg Leu Thr Thr Lys Gly Arg Pro Asp Phe>

4162 CTA AGG ATT GAA TGT TTT GTG TGG GAT GAC AAT TTG
     Leu Arg Ile Glu Cys Phe Val Trp Asp Asp Asn Leu>

4198 TGG TGT CAC CAA TTT TAC AGA TTC GAG GCT GAC ATC
     Trp Cys His Gln Phe Tyr Arg Phe Glu Ala Asp Ile>

4234 GCC AAC TCT ACA ACC AGT GTT GAG AAT TTA GTC CGT
     Ala Asn Ser Thr Thr Ser Val Glu Asn Leu Val Arg>

4270 ATA AGA TTC TCA TGT AAC CGT TAATTTTTATCCCGGGAGATCT
     Ile Arg Phe Ser Cys Asn Arg>

4313 TAGCTAACTGATTTTTCTGGGAAAAAAATTA
```

```
  1 GTATCATTTTTATCTAATTTTGGAGATTTAGCAGTACTTACTTCATTAGA

51 AGAAGAATCTGCCAGTTCCTGTCTATTACTGATATTTCGTTTCATTATTA

101 TATGATTTATATTTTACTTTTTCAATTATATATACTCATTTGACTAGTTA

151 ATCAATAAAAGAATTCCTCGAGCTGCAGCCCGATCCATAAAAATCA

198 GTG TGA TCT CAC ATA GGA TTT CGA AGT TCC AGT TAG
    <His Ser Arg Val Tyr Ser Lys Ser Thr Gly Thr Leu

234 ATC AGG TTT AAA TGC CGG ATC GAC CTT AGT ATG CTG
    <Asp Pro Lys Phe Ala Pro Asp Val Lys Thr His Gln

270 CTT GAG TGT CTG TTG GTA GCG TCT TTT ACA ACA GTA
    <Lys Leu Thr Gln Gln Tyr Arg Arg Lys Cys Cys Tyr

306 AAT CAG CAA CAA CAA AGC CAG GGC TGT ACA ACT TAA
    <Ile Leu Leu Leu Leu Ala Leu Ala Thr Cys Ser Leu

342 TAT AGG AAC GCT GAG GAG ACT GCC AAA ATT GAA GGA
    <Ile Pro Val Ser Leu Leu Ser Gly Phe Asn Phe Ser

378 AGA GCG CCT AAC CGT CTC AAG GAT CTG GTT AGA GGA
    <Ser Arg Arg Val Thr Glu Leu Ile Gln Asn Ser Ser

414 GTC TAT CAG TAC CTT AGC ATC ATC CAG TTT CTT AAG
    <Asp Ile Leu Val Lys Ala Asp Asp Leu Lys Lys Leu

450 GGC GTT CCC TAA GTT TGT ACC TAC ATC TAA CCT ATC
    <Ala Asn Gly Leu Asn Thr Gly Val Asp Leu Arg Asp

486 AAG TGA TAT AGC AGG GCC TAA GGC AAC TTT GCC TTC
    <Leu Ser Ile Ala Pro Gly Leu Ala Val Lys Gly Glu

522 GTA TAC CAT ATC AGG GTA TTG CCT GCC TCC AAC TTG
    <Tyr Val Met Asp Pro Tyr Gln Arg Gly Gly Val Gln

558 GAT AGT AGC ACC ATC TAT TTC AAC CAG TGG GCA GGT
    <Ile Thr Ala Gly Asp Ile Glu Val Leu Pro Cys Thr

594 ATC GGA GGC AAT GAA TGT CAG CAA CTT ATC AGG ACT
    <Asp Ser Ala Ile Phe Thr Leu Leu Lys Asp Pro Ser

630 CTG ATT AAT AAT TGT GCT TGT GCT ATA ACA CTT ACA
    <Gln Asn Ile Ile Thr Ser Thr Ser Tyr Cys Lys Cys

666 TAG TAT AGA AGC ACA ATT TGC GAC GAT ATT ACC TTT
    <Leu Ile Ser Ala Cys Asn Ala Val Ile Asn Gly Lys
```

```
 702 TGA CAG AAT AAA TTT GTT GCC CAT AGT CCC AGA TAC
    <Ser Leu Ile Phe Lys Asn Gly Met Thr Gly Ser Val

738 CAA GGT CCG AGC ACA AGA TGA AGT GTC GCC CCT AAT
    <Leu Thr Arg Ala Cys Ser Ser Thr Asp Gly Arg Ile

774 ACA TTG TTG TAA GAG TGG GCT CAT GGG ATA CAG GGA
    <Cys Gln Gln Leu Leu Pro Ser Met Pro Tyr Leu Ser

810 GTT CTG GCT ACA AAT GGC TGA CTC TGA GAC GAA TAC
    <Asn Gln Ser Cys Ile Ala Ser Glu Ser Val Phe Val

846 ACA AGA TGA CTC ATC AAA ATT AGA TAT TAA GTA ACC
    <Cys Ser Ser Glu Asp Phe Asn Ser Ile Leu Tyr Gly

882 ATT AGT TGC AAT ATA CCT CGG GAC AGT GGT GTA CCA
    <Asn Thr Ala Ile Tyr Arg Pro Val Thr Thr Tyr Trp

918 CTC TTG TGA TCC TAT GTT GTA AGA AAC CGC TTC CAG
    <Glu Gln Ser Gly Ile Asn Tyr Ser Val Ala Glu Leu

954 TCT GTG GAC TAT AAC CCC CTT GAC TTC TGA TAA AGT
    <Arg His Val Ile Val Gly Lys Val Glu Ser Leu Thr

990 TGG GTA TGA GAT ACT TAG GAT GAT GAA TTT CCC GGG
    <Pro Tyr Ser Ile Ser Leu Ile Ile Phe Lys Gly Pro

1026 AAG ATC AAC ATG AGT TAT TTT TGT TTT TAT CCC CCG
    <Leu Asp Val His Thr Ile Lys Thr Lys Ile Gly Arg

1062 ACT CTC CAA GAT TGC AAT CAT ATC ACT TCC AGA ATA
    <Ser Glu Leu Ile Ala Ile Met Asp Ser Gly Ser Tyr

1098 TCC CAA CTT CCC AAG TAT CTT ATG AAT TTC TCC TCC
    <Gly Leu Lys Gly Leu Ile Lys His Ile Glu Gly Gly

1134 AAG AGC ATA AAT CAG TGC CTG AAT TGA TAT CTC GGC
    <Leu Ala Tyr Ile Leu Ala Gln Ile Ser Ile Glu Ala

1170 TGA AAT AGG GTC ACG TAA ACT CGG GCC AAA TAT TGA
    <Ser Ile Pro Asp Arg Leu Ser Pro Gly Phe Ile Ser

1206 CAA CAA CTC AGT ATA ATA CCG AAG CAG TCT TAA CCC
    <Leu Leu Glu Thr Tyr Tyr Arg Leu Leu Arg Leu Gly

1242 TAA TCT CTG CCC AAC TAA TTC ACA TGA CAT ATG TTG
    <Leu Arg Gln Gly Val Leu Glu Cys Ser Met His Gln

1278 CAT GGC AGG GAC GAG TTC GTT GTT GAC GTA GTC CTG
    <Met Ala Pro Val Leu Glu Asn Asn Val Tyr Asp Gln
```

*FIG. 17B*

```
1314 GAC TCC CTG AAC GGC AAT GAC GGT TTC TTG GGT AGC
    <Val Gly Gln Val Ala Ile Val Thr Glu Gln Thr Ala

1350 CTC CCT AAT TTC TTC TAT AGC TTT GTT AGA CTG TTC
    <Glu Arg Ile Glu Glu Ile Ala Lys Asn Ser Gln Glu

1386 AAG GCT GGT TCT AAG AGA TTG GAT TGC TTG AGC ATT
    <Leu Ser Thr Arg Leu Ser Gln Ile Ala Gln Ala Asn

1422 GAG GTT GGA TTG ATG TAA AGC TAT TCC TGC AGT GAT
    <Leu Asn Ser Gln His Leu Ala Ile Gly Ala Thr Ile

1458 TTG TGC AGC TGT AGC CAC TCC TAA AGC TAC ACC TGC
    <Gln Ala Ala Thr Ala Val Gly Leu Ala Val Gly Ala

1494 AAG TAC CAC TCC TGC AAA ACG CCT TTG TCT CCT ACC
    <Leu Val Val Gly Ala Phe Arg Arg Gln Arg Arg Gly

1530 TGA CCC TAA TGA CTG CAG GGG CTT CAC ATT CTT GGT
    <Ser Gly Leu Ser Gln Leu Pro Lys Val Asn Lys Thr

1566 CAT TAG AGT CAA AGC TTG GTT GAT TGG TTC GAG GAC
    <Met Leu Thr Leu Ala Gln Asn Ile Pro Glu Leu Val

1602 TGA ATT CAA TAA TTT CTC ATA CTC ACC TAA TTC TGC
    <Ser Asn Leu Leu Lys Glu Tyr Glu Gly Leu Glu Ala

1638 TTT GGT ACA ATT CTC TAT AAG TGA AAC ATT AGG CAT
    <Lys Thr Cys Asn Glu Ile Leu Ser Val Asn Pro Met

1674 CAG TTT TAT GAC CAA GTA CTG GTG ACT GGG CCT AGT
    <Leu Lys Ile Val Leu Tyr Gln His Ser Pro Arg Thr

1710 CAT GAT CTT GTA ATG GAC ACT ATC AGT CCC GAT AAT
    <Met Ile Lys Tyr His Val Ser Asp Thr Gly Ile Ile

1746 CCC AAT AGT TGA CAA ATT ATT CCA ATG TAT CTG AGC
    <Gly Ile Thr Ser Leu Asn Asn Trp His Ile Gln Ala

1782 CTT GGA ACA AAG AAA GAG ACT GGC CAT TCC GAG GCA
    <Lys Ser Cys Leu Phe Leu Ser Ala Met Gly Leu Cys

1818 CCA CAG GAC TAA CCA GGT GCA ATG AGA GCC TGA GTT
    <Trp Leu Val Leu Trp Thr Cys His Ser Gly Ser Asn

1854 GAT TGC ATT GGG TTG CCG CCT TTC GAT CTG GGA TCT
    <Ile Ala Asn Pro Gln Arg Arg Glu Ile Gln Ser Arg

1890 CGC TCC TTT TGA GAC ACT CTC TGG TAT GTG CTG GAT
    <Ala Gly Lys Ser Val Ser Glu Pro Ile His Gln Ile
```

FIG. 17C

```
1926 GGT GGC CTC GTG GTT TCC GTG AAC TGG GAT GTT CTT
    <Thr Ala Glu His Asn Gly His Val Pro Ile Asn Lys

1962 CAA TCT GTG GCT GGT TTG CTT GCG GGA CCT GGT CCT
    <Leu Arg His Ser Thr Gln Lys Arg Ser Arg Thr Arg

1998 GTT CAT GGT GTA GGA GAC GGG TCT GTC CGA TGT TCG
    <Asn Met Thr Tyr Ser Val Pro Arg Asp Ser Thr Arg

2034 AGG ATC GTA GTG CGT GGA TCG CTG AGC TGA TGT TGT
    <Pro Asp Tyr His Thr Ser Arg Gln Ala Ser Thr Thr

2070 GCT GTG TCG TGC TCG GGA GGT CCT GGT CTC TTC GAG
    <Ser His Arg Ala Arg Ser Thr Arg Thr Glu Glu Leu

2106 TTC GGT GCT GGG TTG TGG GGG GCG GTC TTG TTG GGT
    <Glu Thr Ser Pro Gln Pro Pro Arg Asp Gln Gln Thr

2142 ATG TGT TTG GGT TTT GGA GCT TTT GGG GAT TCC CTT
    <His Thr Gln Thr Lys Ser Ser Lys Pro Ile Gly Lys

2178 GTG CAT TAC GAT ACA AAC TTAACGGATATCGCGATAATGAAATA
    <His Met

2222 ATTTATGATTATTTCTCGCTTTCAATTTAACACAACCCTCAAGAACCTTT

2272 GTATTTATTTTCACTTTTTAAGTATAGAATAAAGAAGCTCTAATTAATTA

2322 AGCTACAAATAGTTTCGTTTTCACCTTGTCTAATAACTAATTAATTAACC

2372 CCGATAGCTGATTAGTTTTTGTTGGGTTAATTAATTAGTCATCAGGCAGG

2422 GCGAGAACGAGACTATCTGCTCGTTAATTAATTAGAGCTTGATTCTTTAT

2472 TCTATACTTAAAAAGTGAAAATAAATACAAAGGTTCTTGAGGGTTGTGTT

2522 AAATTGAAAGCGAGAAATAATCATAAATTATTTCATTATCGCGATATCCG

2572 TTAA GTT TGT ATC GTA ATG CTC CCC TAC CAA GAC AAG
              Met Leu Pro Tyr Gln Asp Lys>

2609 GTG GGT GCC TTC TAC AAG GAT AAT GCA AGA GCC AAT
    Val Gly Ala Phe Tyr Lys Asp Asn Ala Arg Ala Asn>

2645 TCA ACC AAG CTG TCC TTA GTG ACA GAA GGA CAT GGG
    Ser Thr Lys Leu Ser Leu Val Thr Glu Gly His Gly>

2681 GGC AGG AGA CCA CCT TAT TTG TTG TTT GTC CTT CTC
    Gly Arg Arg Pro Pro Tyr Leu Leu Phe Val Leu Leu>
```

FIG. 17D

```
2717 ATC TTA TTG GTT GGT ATC CTG GCC TTG CTT GCT ATC
     Ile Leu Leu Val Gly Ile Leu Ala Leu Leu Ala Ile>

2753 ACT GGA GTT CGA TTT CAC CAA GTA TCA ACT AGT AAT
     Thr Gly Val Arg Phe His Gln Val Ser Thr Ser Asn>

2789 ATG GAA TTT AGC AGA TTG CTG AAA GAG GAT ATG GAG
     Met Glu Phe Ser Arg Leu Leu Lys Glu Asp Met Glu>

2825 AAA TCA GAG GCC GTA CAT CAC CAA GTC ATA GAT GTC
     Lys Ser Glu Ala Val His His Gln Val Ile Asp Val>

2861 TTG ACA CCG CTC TTC AAG ATT ATT GGA GAT GAG ATT
     Leu Thr Pro Leu Phe Lys Ile Ile Gly Asp Glu Ile>

2897 GGG TTA CGG TTG CCA CAA AAG CTA AAC GAG ATC AAA
     Gly Leu Arg Leu Pro Gln Lys Leu Asn Glu Ile Lys>

2933 CAA TTT ATC CTT CAA AAG ACA AAT TTC TTC AAT CCG
     Gln Phe Ile Leu Gln Lys Thr Asn Phe Phe Asn Pro>

2969 AAC AGA GAA TTC GAC TTC CGC GAT CTC CAC TGG TGC
     Asn Arg Glu Phe Asp Phe Arg Asp Leu His Trp Cys>

3005 ATT AAC CCG CCT AGT ACG GTC AAG GTG AAT TTT ACT
     Ile Asn Pro Pro Ser Thr Val Lys Val Asn Phe Thr>

3041 AAT TAC TGT GAG TCA ATT GGG ATC AGA AAA GCT ATT
     Asn Tyr Cys Glu Ser Ile Gly Ile Arg Lys Ala Ile>

3077 GCA TCG GCA GCA AAT CCT ATC CTT TTA TCA GCC CTA
     Ala Ser Ala Ala Asn Pro Ile Leu Leu Ser Ala Leu>

3113 TCT GGG GGC AGA GGT GAC ATA TTC CCA CCA CAC AGA
     Ser Gly Gly Arg Gly Asp Ile Phe Pro Pro His Arg>

3149 TGC AGT GGA GCT ACT ACT TCA GTA GGC AAA GTT TTC
     Cys Ser Gly Ala Thr Thr Ser Val Gly Lys Val Phe>

3185 CCC CTA TCA GTC TCA TTA TCC ATG TCT TTG ATC TCA
     Pro Leu Ser Val Ser Leu Ser Met Ser Leu Ile Ser>

3221 AGA ACC TCA GAG GTA ATC AAT ATG CTG ACC GCT ATC
     Arg Thr Ser Glu Val Ile Asn Met Leu Thr Ala Ile>

3257 TCA GAC GGC GTG TAT GGC AAA ACT TAC TTG CTA GTG
     Ser Asp Gly Val Tyr Gly Lys Thr Tyr Leu Leu Val>

3293 CCT GAT GAT ATA GAA AGA GAG TTC GAC ACT CGA GAG
     Pro Asp Asp Ile Glu Arg Glu Phe Asp Thr Arg Glu>
```

FIG. 17E

```
3329 ATT CGA GTC TTT GAA ATA GGG TTC ATC AAG AGG TGG
     Ile Arg Val Phe Glu Ile Gly Phe Ile Lys Arg Trp>

3365 CTG AAT GAC ATG CCA TTA CTC CAA ACA ACC AAC TAT
     Leu Asn Asp Met Pro Leu Leu Gln Thr Thr Asn Tyr>

3401 ATG GTA CTC CCG AAG AAT TCC AAA GCC AAG GTA TGT
     Met Val Leu Pro Lys Asn Ser Lys Ala Lys Val Cys>

3437 ACT ATA GCA GTG GGT GAG TTG ACA CTG GCT TCC TTG
     Thr Ile Ala Val Gly Glu Leu Thr Leu Ala Ser Leu>

3473 TGT GTA GAA GAG AGC ACT GTA TTA TTA TAT CAT GAC
     Cys Val Glu Glu Ser Thr Val Leu Leu Tyr His Asp>

3509 AGC AGT GGT TCA CAA GAT GGT ATT CTA GTA GTG ACA
     Ser Ser Gly Ser Gln Asp Gly Ile Leu Val Val Thr>

3545 CTG GGG ATA TTT TGG GCA ACA CCT ATG GAT CAC ATT
     Leu Gly Ile Phe Trp Ala Thr Pro Met Asp His Ile>

3581 GAG GAA GTG ATA CCT GTC GCT CAC CCA TCA ATG AAG
     Glu Glu Val Ile Pro Val Ala His Pro Ser Met Lys>

3617 AAA ATA CAT ATA ACA AAC CAC CGT GGT TTT ATA AAA
     Lys Ile His Ile Thr Asn His Arg Gly Phe Ile Lys>

3653 GAT TCA ATT GCA ACC TGG ATG GTG CCT GCC CTG GCC
     Asp Ser Ile Ala Thr Trp Met Val Pro Ala Leu Ala>

3689 TCT GAG AAA CAA GAA GAA CAA AAA GGT TGT CTG GAG
     Ser Glu Lys Gln Glu Glu Gln Lys Gly Cys Leu Glu>

3725 TCA GCT TGT CAA AGA AAA ACC TAC CCC ATG TGC AAC
     Ser Ala Cys Gln Arg Lys Thr Tyr Pro Met Cys Asn>

3761 CAA GCG TCA TGG GAA CCC TTC GGA GGA AGA CAG TTG
     Gln Ala Ser Trp Glu Pro Phe Gly Gly Arg Gln Leu>

3797 CCA TCT TAT GGG CGG TTG ACA TTA CCT CTA GAT GCA
     Pro Ser Tyr Gly Arg Leu Thr Leu Pro Leu Asp Ala>

3833 AGT GTT GAC CTT CAA CTT AAC ATA TCG TTC ACA TAC
     Ser Val Asp Leu Gln Leu Asn Ile Ser Phe Thr Tyr>

3869 GGT CCG GTT ATA CTG AAT GGA GAT GGT ATG GAT TAT
     Gly Pro Val Ile Leu Asn Gly Asp Gly Met Asp Tyr>

3905 TAT GAA AGC CCA CTT TTG AAC TCC GGA TGG CTT ACC
     Tyr Glu Ser Pro Leu Leu Asn Ser Gly Trp Leu Thr>
```

FIG. 17F

```
3941 ATT CCC CCC AAA GAC GGA ACA ATC TCT GGA TTG ATA
     Ile Pro Pro Lys Asp Gly Thr Ile Ser Gly Leu Ile>

3977 AAC AAA GCA GGT AGA GGA GAC CAG TTC ACT GTA CTC
     Asn Lys Ala Gly Arg Gly Asp Gln Phe Thr Val Leu>

4013 CCC CAT GTG TTA ACA TTT GCG CCC AGG GAA TCA AGT
     Pro His Val Leu Thr Phe Ala Pro Arg Glu Ser Ser>

4049 GGA AAT TGT TAT TTA CCT ATT CAA ACA TCT CAA ATT
     Gly Asn Cys Tyr Leu Pro Ile Gln Thr Ser Gln Ile>

4085 AGA GAT AGA GAT GTC CTC ATT GAG TCC AAT ATA GTG
     Arg Asp Arg Asp Val Leu Ile Glu Ser Asn Ile Val>

4121 GTG TTG CCT ACA CAG AGT ATT AGA TAT GTC ATA GCA
     Val Leu Pro Thr Gln Ser Ile Arg Tyr Val Ile Ala>

4157 ACG TAT GAC ATA TCA CGA AGT GAT CAT GCT ATT GTT
     Thr Tyr Asp Ile Ser Arg Ser Asp His Ala Ile Val>

4193 TAT TAT GTT TAT GAC CCA ATC CGG ACG ATT TCT TAT
     Tyr Tyr Val Tyr Asp Pro Ile Arg Thr Ile Ser Tyr>

4229 ACG CAC CCA TTT AGA CTA ACT ACC AAG GGT AGA CCT
     Thr His Pro Phe Arg Leu Thr Thr Lys Gly Arg Pro>

4265 GAT TTC CTA AGG ATT GAA TGT TTT GTG TGG GAT GAC
     Asp Phe Leu Arg Ile Glu Cys Phe Val Trp Asp Asp>

4301 AAT TTG TGG TGT CAC CAA TTT TAC AGA TTC GAG GCT
     Asn Leu Trp Cys His Gln Phe Tyr Arg Phe Glu Ala>

4337 GAC ATC GCC AAC TCT ACA ACC AGT GTT GAG AAT TTA
     Asp Ile Ala Asn Ser Thr Thr Ser Val Glu Asn Leu>

4373 GTC CGT ATA AGA TTC TCA TGT AAC CGT TAATTTTATCCCG
     Val Arg Ile Arg Phe Ser Cys Asn Arg>

4414 GGTTTTTATAGCTAATTAGTCATTTTTTCGTAAGTAAGTATTTTTATTTA

4464 ATACTTTTTATTGTACTTATGTTAAATATAACTGATGATAACAAAATCCA

4514 TTATGTATTATTTATAACTGTAATTTCTTTAGCGTAGTTAGATGTCCAAT

4564 CTCTCTCAAATACATCGGCTATCTTTTAGTGAGATTTTGA
```

FIG. 17G

SEQUENCE LISTING ( 1 ) GENERAL INFORMATION:

( i i i ) NUMBER OF SEQUENCES: 122

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

TAATTAACTA GCTACCCGGG                                                      20

( 2 ) INFORMATION FOR SEQ ID NO:2:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

GTACATTAAT TGATCGATGG GCCCTTAA                                             28

( 2 ) INFORMATION FOR SEQ ID NO:3:

( i ) SEQUENCE CHARACTERISTICS:
    ( A ) LENGTH: 73 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

AGCTTCCCGG GTAAGTAATA CGTCAAGGAG AAAACGAAAC GATCTGTAGT TAGCGGCCGC          60

CTAATTAACT AAT                                                            73

( 2 ) INFORMATION FOR SEQ ID NO:4:

( i ) SEQUENCE CHARACTERISTICS:
    ( A ) LENGTH: 69 base pairs
    ( B ) TYPE: nucleic acid ( C ) STRANDEDNESS: single
            ( D ) TOPOLOGY: linear ( i i ) MOLECULE TYPE: cDNA ( x i ) SEQUENCE DESCRIPTION: SEQ ID NO:4:

AGGGCCCATT CATTATGCAG TTCCTCTTTT GCTTTGCTAG ACATCAATCG CCGGCGGATT       60

AATTGATTA                                                               69

( 2 ) INFORMATION FOR SEQ ID NO:5:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:5:

TTAGTTAATT AGGCGGCCGC                                                   20

( 2 ) INFORMATION FOR SEQ ID NO:6:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

CGATTACTAT GAAGGATCCG TT                                                22

( 2 ) INFORMATION FOR SEQ ID NO:7:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:7:

TAATGATACT TCCTAGGCAA                                                   20

( 2 ) INFORMATION FOR SEQ ID NO:8:

( i ) SEQUENCE CHARACTERISTICS:
            ( A ) LENGTH: 41 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:8:

CGATTACTAG ATCTGAGCTC CCCGGGCTCG AGGGATCCGT T                           41

( 2 ) INFORMATION FOR SEQ ID NO:9:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:9:

TAATGATCTA GACTCGAGGG GCCCGAGCTC CCTAGGCAA 39

( 2 ) INFORMATION FOR SEQ ID NO:10:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:10:

GATCCGAATT CTAGCT 16

( 2 ) INFORMATION FOR SEQ ID NO:11:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:11:

GCTTAAGATC GA 12

( 2 ) INFORMATION FOR SEQ ID NO:12:

( i ) SEQUENCE CHARACTERISTICS:
       ( A ) LENGTH: 75 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:12:

TATGAGTAAC TTAACTCTTT TGTTAATTAA AAGTATATTC AAAAAATAAG TTATATAAAT 60

AGATCTGAAT TCGTT 75

( 2 ) INFORMATION FOR SEQ ID NO:13:

( i ) SEQUENCE CHARACTERISTICS:
       ( A ) LENGTH: 73 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:13:

ACTCATTGAA TTGAGAAAAC AATTAATTTT CATATAAGTT TTTTATTCAA TATATTTATC 60

TAGACTTAAG CAA 73

( 2 ) INFORMATION FOR SEQ ID NO:14:

( i ) SEQUENCE CHARACTERISTICS:
       ( A ) LENGTH: 49 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:14:

AAAATGGGCG TGGATTGTTA ACTTTATATA ACTTATTTTT TGAATATAC          49

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

ACACGAATGA TTTTCTAAAG TATTGGAAA GTTTATAGG TAGTTGATAG AACAAATAC          60

ATAATTT          67

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

TGTGCTTACT AAAAGATTTC ATAAACCTTT CAAAATATCC ATCAACTATC T          51

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

TGTAAAAATA AATCACTTTT TATACTAAGA TCTCCCGGGC TGCAGC          46

( 2 ) INFORMATION FOR SEQ ID NO:18:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

TGTTTTATGT ATTAAAACAT TTTTATTTAG TGAAAAATAT GATTCTAGAG GGCCCGACGT          60

CGCCGG          66

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA (x i) SEQUENCE DESCRIPTION: SEQ ID NO:19:

TTTCTGTATA TTTGCACCAA TTTAGATCTT ACTCAAAATA TGTAACAATA                    50

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:20:

TGTCATTTAA CACTATACTC ATATTAATAA AAATAATATT TATT                          44

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:21:

GATCCTGAGT ACTTTGTAAT ATAATGATAT ATATTTCAC TTTATCTCAT TTGAGAATAA          60

AAAGATCTTA GG                                                             72

(2) INFORMATION FOR SEQ ID NO:22:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:22:

GACTCATGAA ACATTATATT ACTATATATA AAAGTGAAAT AGAGTAAACT CTTATTTTTC         60

TAGAATCCTT AA                                                             72

(2) INFORMATION FOR SEQ ID NO:23:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:23:

GATCCAGATC TCCCGGGAAA AAAATTATTT AACTTTTCAT TAATAGGGAT TTGACGTATG         60

TAGCGTACTA GG                                                             72

(2) INFORMATION FOR SEQ ID NO:24:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:24:

GTCTAGAGGG CCCTTTTTTT AATAAATTGA AAAGTAATTA TCCCTAAACT GCATACTACG    60

CATGATCCTT AA    72

( 2 ) INFORMATION FOR SEQ ID NO:25:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GGGAGATCTC TCGAGCTGCA GGGCGCCGGA TCCTTTTTCT    40

( 2 ) INFORMATION FOR SEQ ID NO:26:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CCCTCTAGAG AGCTCGACGT CCCGCGGCCT AGGAAAAAGA    40

( 2 ) INFORMATION FOR SEQ ID NO:27:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CGATATCCGT TAAGTTTGTA TCGTAATGGG CTCCAGATCT TCTACCAGGA TCCCGGTAC    59

( 2 ) INFORMATION FOR SEQ ID NO:28:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CGGGATCCTG GTAGAAGATC TGGAGCCCAT TACGATACAA ACTTAACGGA TATCG    55

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

AATTCGAGCT CCCCGGG                                                                                17

( 2 ) INFORMATION FOR SEQ ID NO:30:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

CCCGGGGAGC TCG                                                                                    13

( 2 ) INFORMATION FOR SEQ ID NO:31:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

CTTTTTATAA AAAGTTAACT ACGTAG                                                                      26

( 2 ) INFORMATION FOR SEQ ID NO:32:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

GATCCTACGT AGTTAACTTT TTATAAAAAG AGCT                                                              34

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

CTTAACTCAG CTGACTATCC                                                                             20

( 2 ) INFORMATION FOR SEQ ID NO:34:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TACGTAGTTA ACTTTTTATA AAAATCATAT TTTGTAGTG GCTC                                                    44

( 2 ) INFORMATION FOR SEQ ID NO:35:

(i) SEQUENCE CHARACTERISTICS:
    (A) LENGTH: 67 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:35:

```
AATTCAGGAT CGTTCCTTTA CTAGTTGAGA TTCTCAAGGA TGATGGGATT TAATTTTTAT      60
AAGCTTG                                                                67
```

(2) INFORMATION FOR SEQ ID NO:36:

(i) SEQUENCE CHARACTERISTICS:
    (A) LENGTH: 67 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:36:

```
AATTCAAGCT TATAAAAATT AAATCCCATC ATCCTTGAGA ATCTCAACTA GTAAAGGAAC      60
GATCCTG                                                                67
```

(2) INFORMATION FOR SEQ ID NO:37:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:37:

```
CTAGACACTT TATGTTTTTT AATATCCGGT CTTAAAAGCT TCCCGGGGAT CCTTATACGG      60
GGAATAAT                                                               68
```

(2) INFORMATION FOR SEQ ID NO:38:

(i) SEQUENCE CHARACTERISTICS:
    (A) LENGTH: 65 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:38:

```
ATTATTCCCC GTATAAGGAT CCCCCGGGAA GCTTTTAAGA CCGGATATTA AAAACATAA       60
AGTGT                                                                  65
```

(2) INFORMATION FOR SEQ ID NO:39:

(i) SEQUENCE CHARACTERISTICS:
    (A) LENGTH: 3209 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:39:

```
TGAATGTTAA ATGTTATACT TTGGATGAAG CTATAAATAT GCATTGGAAA AATAATCCAT      60
```

| | | | | |
|---|---|---|---|---|
| TTAAAGAAAG | GATTCAAATA | CTACAAAACC | TAAGCGATAA | TATGTTAACT AAGCTTATTC | 120 |
| TTAACGACGC | TTTAAATATA | CACAAATAAA | CATAATTTTT | GTATAACCTA ACAAATAACT | 180 |
| AAAACATAAA | AATAATAAAA | GGAAATGTAA | TATCGTAATT | ATTTACTCA GGAATGGGGT | 240 |
| TAAATATTTA | TATCACGTGT | ATATCTATAC | TGTTATCGTA | TACTCTTTAC AATTACTATT | 300 |
| ACGAATATGC | AAGAGATAAT | AAGATTACGT | ATTAAGAGA | ATCTTGTCAT GATAATTGGG | 360 |
| TACGACATAG | TGATAAATGC | TATTTCGCAT | CGTTACATAA | AGTCAGTTGG AAAGATGGAT | 420 |
| TTGACAGATG | TAACTTAATA | GGTGCAAAAA | TGTTAAATAA | CAGCATTCTA TCGGAAGATA | 480 |
| GGATACCAGT | TATATTATAC | AAAAATCACT | GGTTGGATAA | AACAGATTCT GCAATATTCG | 540 |
| TAAAAGATGA | AGATTACTGC | GAATTTGTAA | ACTATGACAA | TAAAAAGCCA TTTATCTCAA | 600 |
| CGACATCGTG | TAATTCTTCC | ATGTTTTATG | TATGTGTTTC | AGATATTATG AGATTACTAT | 660 |
| AAACTTTTTG | TATACTTATA | TTCCGTAAAC | TATATTAATC | ATGAAGAAAA TGAAAAAGTA | 720 |
| TAGAAGCTGT | TCACGAGCGG | TTGTTGAAAA | CAACAAAATT | ATACATTCAA GATGGCTTAC | 780 |
| ATATACGTCT | GTGAGGCTAT | CATGGATAAT | GACAATGCAT | CTCTAAATAG GTTTTGGAC | 840 |
| AATGGATTCG | ACCCTAACAC | GGAATATGGT | ACTCTACAAT | CTCCTCTTGA AATGGCTGTA | 900 |
| ATGTTCAAGA | ATACCGAGGC | TATAAAAATC | TTGATGAGGT | ATGGAGCTAA ACCTGTAGTT | 960 |
| ACTGAATGCA | CAACTTCTTG | TCTGCATGAT | GCGGTGTTGA | GAGACGACTA CAAAATAGTG | 1020 |
| AAAGATCTGT | TGAAGAATAA | CTATGTAAAC | AATGTTCTTT | ACAGCGGAGG CTTTACTCCT | 1080 |
| TTGTGTTTGG | CAGCTTACCT | TAACAAAGTT | AATTTGGTTA | AACTTCTATT GGCTCATTCG | 1140 |
| GCGGATGTAG | ATATTTCAAA | CACGGATCGG | TTAACTCCTC | TACATATAGC CGTATCAAAT | 1200 |
| AAAAATTTAA | CAATGGTTAA | ACTTCTATTG | AACAAAGGTG | CTGATACTGA CTTGCTGGAT | 1260 |
| AACATGGGAC | GTACTCCTTT | AATGATCGCT | GTACAATCTG | GAAATATTGA AATATGTAGC | 1320 |
| ACACTACTTA | AAAAAAATAA | AATGTCCAGA | ACTGGGAAAA | ATTGATCTTG CCAGCTGTAA | 1380 |
| TTCATGGTAG | AAAAGAAGTG | CTCAGGCTAC | TTTTCAACAA | AGGAGCAGAT GTAAACTACA | 1440 |
| TCTTTGAAAG | AAATGGAAAA | TCATATACTG | TTTTGGAATT | GATTAAAGAA AGTTACTCTG | 1500 |
| AGACACAAAA | GAGGTAGCTG | AAGTGGTACT | CTCAAAATGC | AGAACGATGA CTGCGAAGCA | 1560 |
| AGAAGTAGAG | AAATAACACT | TTATGACTTT | CTTAGTTGTA | GAAAGATAG AGATATAATG | 1620 |
| ATGGTCATAA | ATAACTCTGA | TATTGCAAGT | AAATGCAATA | ATAAGTTAGA TTTATTTAAA | 1680 |
| AGGATAGTTA | AAAATAGAAA | AAAAGAGTTA | ATTTGTAGGG | TTAAAATAAT ACATAAGATC | 1740 |
| TTAAAATTTA | TAAATACGCA | TAATAATAAA | AATAGATTAT | ACTTATTACC TTCAGAGATA | 1800 |
| AAATTTAAGA | TATTTACTTA | TTTAACTTAT | AAAGATCTAA | AATGCATAAT TTCTAAATAA | 1860 |
| TGAAAAAAAA | GTACATCATG | AGCAACGCGT | TAGTATATTT | TACAATGGAG ATTAACGCTC | 1920 |
| TATACCGTTC | TATGTTTATT | GATTCAGATG | ATGTTTTAGA | AAAGAAAGTT ATTGAATATG | 1980 |
| AAAACTTTAA | TGAAGATGAA | GATGACGACG | ATGATTATTG | TTGTAAATCT GTTTAGATG | 2040 |
| AAGAAGATGA | CGCGCTAAAG | TATACTATGG | TTACAAAGTA | TAAGTCTATA CTACTAATGG | 2100 |
| CGACTTGTGC | AAGAAGGTAT | AGTATAGTGA | AAATGTTGTT | AGATTATGAT TATGAAAAAC | 2160 |
| CAAATAAATC | AGATCCATAT | CTAAAGGTAT | CTCCTTTGCA | CATAATTTCA TCTATTCCTA | 2220 |
| GTTTAGAATA | CTTTTCATTA | TATTTGTTTA | CAGCTGAAGA | CGAAAAAAAT ATATCGATAA | 2280 |
| TAGAAGATTA | TGTTAACTCT | GCTAATAAGA | TGAAATTGAA | TGAGTCTGTG ATAATAGCTA | 2340 |
| TAATCAGAGA | AGTTCTAAAA | GGAAATAAAA | ATCTAACTGA | TCAGGATATA AAAACATTGG | 2400 |
| CTGATGAAAT | CAACAAGGAG | GAACTGAATA | TAGCTAAACT | ATTGTTAGAT AGAGGGGCCA | 2460 |

-continued

| | | | | | |
|---|---|---|---|---|---|
| AAGTAAATTA | CAAGGATGTT | TACGGTTCTT | CAGCTCTCCA | TAGAGCTGCT | ATTGGTAGGA | 2520
| AACAGGATAT | GATAAAGCTG | TTAATCGATC | ATGGAGCTGA | TGTAAACTCT | TTAACTATTG | 2580
| CTAAAGATAA | TCTTATTAAA | AAAAAATAAT | ATCACGTTTA | GTAATATTAA | AATATATTAA | 2640
| TAACTCTATT | ACTAATAACT | CCAGTGGATA | TGAACATAAT | ACGAAGTTTA | TACATTCTCA | 2700
| TCAAAATCTT | ATTGACATCA | AGTTAGATTG | TGAAAATGAG | ATTATGAAAT | TAAGGAATAC | 2760
| AAAAATAGGA | TGTAAGAACT | TACTAGAATG | TTTTATCAAT | AATGATATGA | ATACAGTATC | 2820
| TAGGGCTATA | AACAATGAAA | CGATTAAAAA | TTATAAAAAT | CATTTCCCTA | TATATAATAC | 2880
| GCTCATAGAA | AAATTCATTT | CTGAAAGTAT | ACTAAGACAC | GAATTATTGG | ATGGAGTTAT | 2940
| AAATTCTTTT | CAAGGATTCA | ATAATAAATT | GCCTACGAG | ATTCAGTACA | TTATACTGGA | 3000
| GAATCTTAAT | AACCATGAAC | TAAAAAAAAT | TTTAGATAAT | ATACATTAAA | AAGGTAAATA | 3060
| GATCATCTGT | TATTATAAGC | AAAGATGCTT | GTTGCCAATA | ATATACAACA | GGTATTTGTT | 3120
| TTTATTTTTA | ACTACATATT | TGATGTTCAT | TCTCTTTATA | TAGTATACAC | AGAAAATTCA | 3180
| TAATCCACTT | AGAATTTCTA | GTTATCTAG | | | | 3209

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

GCTTCCCGGG AATTCTAGCT AGCTAGTTT                                                                                       29

( 2 ) INFORMATION FOR SEQ ID NO:41:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

ACTCTCAAAA GCTTCCCGGG AATTCTAGCT AGCTAGTTTT TATAAA                        46

( 2 ) INFORMATION FOR SEQ ID NO:42:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

GATCTTTATA AAAACTAGCT AGCTAGAATT CCCGGGAAGC TTTTGAGAGT          50

( 2 ) INFORMATION FOR SEQ ID NO:43:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

CTGAAATTAT TTCATTATCG CGATATCCGT TAAGTTTGTA TCGTAATGGT TCCTCAGGCT    60

CTCCTGTTTG T    71

( 2 ) INFORMATION FOR SEQ ID NO:44:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

CATTACGATA CAAACTTAAC GGATATCGCG ATAATGAAAT AATTTCAG    48

( 2 ) INFORMATION FOR SEQ ID NO:45:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

ACCCCTTCTG GTTTTCCGT TGTGTTTTGG GAAATTCCCT ATTTACACGA TCCCAGACAA    60

GCTTAGATCT CAG    73

( 2 ) INFORMATION FOR SEQ ID NO:46:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

CTGAGATCTA AGCTTGTCTG GGATCGTGTA AATAGGGAAT TTCCCAAAAC A    51

( 2 ) INFORMATION FOR SEQ ID NO:47:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

CAACGGAAAA ACCAGAAGGG GTACAAACAG GAGAGCCTGA GGAAC    45

( 2 ) INFORMATION FOR SEQ ID NO:48:

( i ) SEQUENCE CHARACTERISTICS:
        ( A ) LENGTH: 3659 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

| | | | | | | |
|---|---|---|---|---|---|---|
| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAAGAAGTAC | CAGTAAAAAG | 120 |
| TGTGGCATAT | GCATAGAAGA | AATAAACAAA | AAACATATTT | CCGAACAGTA | TTTTGGAATT | 180 |
| CTCCCAAGTT | GTAAACATAT | TTTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAAA | TATTATATAA | TAGATATAAG | 360 |
| AAAATGATTT | TTACAAAAAT | ACCTATAAGA | ACAATAAAAA | TATAATTACA | TTTACGGAAA | 420 |
| ATAGCTGGTT | TTAGTTTACC | AACTTAGAGT | AATTATCATA | TTGAATCTAT | ATTGTTTTTT | 480 |
| AGTTATATAA | AAACATGATT | AGCCCCCAAT | CGGATGAAAA | TATAAAGAT | GTTGAGAATT | 540 |
| TCGAATACAA | CAAAAGAGG | AATCGTACGT | TGTCCATATC | CAAACATATA | AATAAAAATT | 600 |
| CAAAAGTAGT | ATTATACTGG | ATGTTTAGAG | ATCAACGTGT | ACAAGATAAT | TGGGCTTTAA | 660 |
| TTTACGCACA | ACGATTAGCG | TTAAAACTCA | AAATACCTCT | AAGAATATGC | TTTTGTGTCG | 720 |
| TGCCAAAATT | TCACACTACT | ACTTCTAGAC | ACTTTATGTT | TTTAATATCC | GGTCTTAAAG | 780 |
| AAGTCGCGGA | AGAATGTAAA | AGACTATGTA | TAGGGTTTTC | ATTGATATAT | GGCGTACCAA | 840 |
| AAGTAATAAT | TCCGTGTATA | GTAAAAAAAT | ACAGAGTCGG | AGTAATCATA | ACGGATTTCT | 900 |
| TTCCATTACG | TGTTCCCGAA | AGATTAATGA | AACAGACTGT | AATATCTCTT | CCAGATAACA | 960 |
| TACCTTTTAT | ACAAGTAGAC | GCTCATAATA | TAGTACCTTG | TTGGGAAGCT | TCTGATAAAG | 1020 |
| AAGAATACGG | TGCACGAACT | TTAAGAAAAA | AGATATTTGA | TAAATTATAT | GAATATATGA | 1080 |
| CAGAATTTCC | TGTTGTTCGT | AAACATCCAT | ACGGTCCATT | TTCTATATCT | ATTGCAAAAC | 1140 |
| CCAAAAATAT | ATCATTAGAC | AAGACGGTAT | TACCCGTAAA | ATGGGCAACG | CCTGGAACAA | 1200 |
| AAGCTGGAAT | AATTGTTTTA | AAAGAATTTA | TAAAAAACAG | ATTACCGTCA | TACGACGCGG | 1260 |
| ATCATAACAA | TCCTACGTGT | GACGCTTTGA | GTAACTTATC | TCCGTGGCTA | CATTTGGTC | 1320 |
| ATGTATCCGC | ACAACGTGTT | GCCTTAGAAG | TATTAAAATG | TATACGAGAA | AGCAAAAAAA | 1380 |
| ACGTTGAAAC | GTTTATAGAT | GAAATAATTG | TAAGAAGAGA | ACTATCGGAT | AATTTTTGTT | 1440 |
| ACTATAACAA | ACATTATGAT | AGTATCCAGT | CTACTCATTC | ATGGGTTAGA | AAAACATTAG | 1500 |
| AAGATCACAT | TAATGATCCT | AGAAAGTATA | TATATTCCAT | TAAACAACTC | GAAAAGCGG | 1560 |
| AAACTCATGA | TCCTCTATGG | AACGCGTCAC | AAATGCAGAT | GGTGAGAGAA | GGAAAAATGC | 1620 |
| ATAGTTTTTT | ACGAATGTAT | TGGGCTAAGA | AGATACTTGA | ATGGACTAGA | ACACCTGAAG | 1680 |
| ACGCTTTGAG | TTATAGTATC | TATTTGAACA | ACAAGTACGA | ACTAGACGGC | ACGGATCCTA | 1740 |
| ACGGATACGT | AGGTTGTATG | TGGTCTATTT | GCGGATTACA | CGATAGAGCG | TGGAAAGCAA | 1800 |
| GACCGATATT | TGGAAAGATA | AGATATATGA | ATTATGAGAG | TTCTAAGAAG | AAATTTGATG | 1860 |
| TTGCTGTATT | TATACAGAAA | TACAATTAAG | ATAAATAATA | TACAGCATTG | TAACCATCGT | 1920 |
| CATCCGTTAT | ACGGGAATA | ATATTACCAT | ACAGTATTAT | TAAATTTTCT | TACGAAGAAT | 1980 |
| ATAGATCGGT | ATTTATCGTT | AGTTTATTTT | ACATTTATTA | ATTAAACATG | TCTACTATTA | 2040 |
| CCTGTTATGG | AAATGACAAA | TTTAGTTATA | TAATTTATGA | TAAAATTAAG | ATAATAATAA | 2100 |
| TGAAATCAAA | TAATTATGTA | AATGCTACTA | GATTATGTGA | ATTACGAGGA | AGAAAGTTTA | 2160 |
| CGAACTGGAA | AAAATTAAGT | GAATCTAAAA | TATTAGTCGA | TAATGTAAAA | AAAATAAATG | 2220 |
| ATAAAACTAA | CCAGTTAAAA | ACGGATATGA | TTATATACGT | TAAGGATATT | GATCATAAAG | 2280 |
| GAAGAGATAC | TTGCGGGTTAC | TATGTACACC | AAGATCTGGT | ATCTTCTATA | TCAAATTGGA | 2340 |

```
TATCTCCGTT  ATTCGCCGTT  AAGGTAAATA  AAATTATTAA  CTATTATATA  TGTAATGAAT      2400
ATGATATACG  ACTTAGCGAA  ATGGAATCTG  ATATGACAGA  AGTAATAGAT  GTAGTTGATA      2460
AATTAGTAGG  AGGATACAAT  GATGAAATAG  CAGAAATAAT  ATATTTGTTT  AATAAATTTA      2520
TAGAAAAATA  TATTGCTAAC  ATATCGTTAT  CAACTGAATT  ATCTAGTATA  TTAAATAATT      2580
TTATAAATTT  TATAAATTTT  AATAAAAAAT  ACAATAACGA  CATAAAGATA  TTTAATCTTT      2640
AATTCTTGAT  CTGAAAAACA  CATCTATAAA  ACTAGATAAA  AAGTTATTCG  ATAAAGATAA      2700
TAATGAATCG  AACGATGAAA  AATTGGAAAC  AGAAGTTGAT  AAGCTAATTT  TTTTCATCTA      2760
AATAGTATTA  TTTTATTGAA  GTACGAAGTT  TTACGTTAGA  TAAATAATAA  AGGTCGATTT      2820
TTACTTTGTT  AAATATCAAA  TATGTCATTA  TCTGATAAAG  ATACAAAAAC  ACACGGTGAT      2880
TATCAACCAT  CTAACGAACA  GATATTACAA  AAATACGTC  GGACTATGGA  AAACGAAGCT       2940
GATAGCCTCA  ATAGAAGAAG  CATTAAAGAA  ATTGTTGTAG  ATGTTATGAA  GAATTGGGAT      3000
CATCCTCAAC  GAAGAAATAG  ATAAAGTTCT  AAACTGGAAA  AATGATACAT  TAAACGATTT      3060
AGATCATCTA  AATACAGATG  ATAATATTAA  GGAAATCATA  CAATGTCTGA  TTAGAGAATT      3120
TGCGTTTAAA  AAGATCAATT  CTATTATGTA  TAGTTATGCT  ATGGTAAAAC  TCAATTCAGA      3180
TAACGAACAT  TGAAAGATAA  AATTAAGGAT  TATTTTATAG  AAACTATTCT  TAAAGACAAA      3240
CGTGGTTATA  AACAAAGCC   ATTACCCGGA  TTGGAAACTA  AATACTAGA   TAGTATTATA      3300
AGATTTTAAA  AACATAAAAT  TAATAGGTTT  TTATAGATTG  ACTTATTATA  TACAATATGG      3360
ATAAAAGATA  TATATCAACT  AGAAAGTTGA  ATGACGGATT  CTTAATTTTA  TATTATGATT      3420
CAATAGAAAT  TATTGTCATG  TCGTGTAATC  ATTTTATAAA  TATATCAGCG  TTACTAGCTA      3480
AGAAAAACAA  GGACTTTAAT  GAATGGCTAA  AGATAGAATC  ATTAGAGAA   ATAATAGATA      3540
CTTTAGATAA  AATTAATTAC  GATCTAGGAC  AACGATATTG  TGAAGAACTT  ACGGCGCATC      3600
ACATTCCAGT  GTAATTATTG  AGGTCAAAGC  TAGTAACTTA  ATAGATGACA  GGACAGCTG       3659
```

( 2 ) INFORMATION FOR SEQ ID NO:49:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

```
TCATTATCGC  GATATCCGTG  TTAACTAGCT  AGCTAATTTT  TATTCCCGGG  ATCCTTATCA        60
```

( 2 ) INFORMATION FOR SEQ ID NO:50:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

```
GTATAAGGAT  CCCGGGAATA  AAAATTAGCT  AGCTAGTTAA  CACGGATATC  GCGATAATGA        60
```

( 2 ) INFORMATION FOR SEQ ID NO:51:

( i ) SEQUENCE CHARACTERISTICS:
        ( A ) LENGTH: 2356 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:51:

| | | | | | | |
|---|---|---|---|---|---|---|
| TGTCTGGACT | AACTGATTTC | ATGGAACAAT | TTTCATCAAA | AATATCAGTT | ATACCTAGTT | 60 |
| CTACAAAGAC | AGAACTTTGA | TGTTATGTTT | GTGTTTGTAT | AGAAAATTTT | GGGATACTAA | 120 |
| CTGATATTTC | TGAATATTTC | TGAATATTTC | ATGTTACTTA | CTTACTCCTA | TCTTAGACGA | 180 |
| TAATAAAATT | CGAGGCGTAA | TATGTTTTC | CAAATATTTG | AAATTCTTAT | ACGTATCGGC | 240 |
| GAAGAAAAGT | AACATACTAT | AAGTGTTATG | CAAGTAAGGT | ATGTAATGA | TATTGGATTT | 300 |
| AATTTCATTG | ACAATACATA | TGTCCAAACA | TTCCACTCGT | AATTATGTAC | GGAACGACTT | 360 |
| TAGTTAAATA | CTTAGTCACA | AAAAACTTAT | GACTGTCATT | ATCTGAAAAC | GGTGATTCCC | 420 |
| ATAAATCAGA | ATACTTAATA | TTAAATAGAA | TGCTCGCTTC | TGGAGGTTTC | CGGATACTAG | 480 |
| ATAACATATC | TTCTGTATTA | TAGTTTAATT | CACTCATTTT | ATTACATAAT | ACAGTAACAT | 540 |
| CTCCCGAAAC | CAATGATGTT | ATATTAGATT | TACTTACATA | CTTCTTGTAA | CTATCATGAA | 600 |
| TACGTTGTT | ATGATCTATA | AAGAAGATGG | ATGTATATTC | TGTTCTAGAT | AGCAAGTTCT | 660 |
| TTAAGTTATT | CTTTGTCTGT | ATTACTATCA | TCGTCTTCAT | CATCGTCTAA | AGGTAGCATT | 720 |
| ATATAATAAA | TCTAATAGTT | GATTTCTCGA | TCTATCAGTA | CTCGCTTTCA | ATAACATTTT | 780 |
| TACTATAAGC | ATAATAGAAG | GCGGTGATAT | CACTATATTT | TTATCGGGTA | TTCTTTTAGT | 840 |
| AATTAGTTAG | TTCGTAGAAT | TTCGTAGAGA | TAAAAGCCAA | TTTGTTGTTG | ATACTGCTTA | 900 |
| CGTTACTCAT | GTTTCTTGTT | TCTGTTAATT | AACAGGTATA | CCCTTACAAT | AAGTTTAATT | 960 |
| AACTTTTAGG | TTTTTGTGAA | GAACTTTTAG | CTTCTAGTTC | CCTTATCCAT | AATTGGGTCT | 1020 |
| TAGATCTAGA | TTCTTCCCAT | GTATAAAGGG | GGACATACCC | AAAATCTTTA | AATGCTTTGT | 1080 |
| CCGTTTCTAT | AGTAAATGTC | GTACATTCCT | TAATCAAAGT | ATAAGGATTT | AGTAAAGGCG | 1140 |
| TGTAAGAACA | AATAGGTGAT | AGTAATACTC | TTAAACCTTT | ATTAATATTA | GCGATAAACC | 1200 |
| TTAAACACCA | TAAAGGAAGA | CATGTATTCC | GTAGATCCAT | CCCTAATTGA | TTAAAGAAAT | 1260 |
| GCATGTTAAA | ATCATGATAA | TGTTCAGTAG | GAGAGGTATC | GTAACAGTAA | TACACGTTAT | 1320 |
| TGCAGAGAGG | ACTATGTTGA | CCATTTTCTA | TCATATTTCT | TGCTGCTAAA | ATATGCATCC | 1380 |
| AAGCTACGTT | TCCTGCATAG | ACTCTGCTAT | GAAATACTTT | ATCATCCGCA | TATTTATACA | 1440 |
| TTTTCCTGCT | TTTATACGAT | CTTCTGTATA | AAGTTCTAG | TACTGGACAG | TATTCTCCGA | 1500 |
| AAACACCTAA | TGGGCGTAGC | GACAAGTGCA | TAATCTAAGT | CCTATATTAG | ACATAGTACC | 1560 |
| GTTAGCTTCT | AGTATATATT | TCTCAGATAA | CTTGTTTACT | AAGAGGATAA | GCCTCTTTAT | 1620 |
| GGTTAGATTG | ATAATACGTA | TTCTCGTTTC | CTCTTATCAT | CGCATCTCCG | GAGAAAGTTA | 1680 |
| GGACCTACCG | CAGAATAACT | ACTCGTATAT | ACTAAGACTC | TTACGCCGTT | ATACAGACAA | 1740 |
| GAATCTACTA | CGTTCTTCGT | TCCGTTGATA | TTAACGTCCA | TTATAGAGTC | GTTAGTAAAC | 1800 |
| TTACCCGCTA | CATCATTTAT | CGAAGCAATA | TGAATGACCA | CATCTGCTGA | TCTAAGCGCT | 1860 |
| TCGTCCAAAG | TACTTTTATT | TCTAACATCT | CCAATCACGG | GAACTATCTT | TATTATATTA | 1920 |
| CATTTTCTA | CAAGATCTAG | TAACCATTGG | TCGATTCTAA | TATCGTAAAC | ACGAACTTCT | 1980 |
| TTTTAAAGAG | GATTCGAACA | AGATAAGATT | ATTTATAATG | TGTCTACCTA | AAAATCCACA | 2040 |
| CCCTCCGGTT | ACCACGTATA | CTAGTGTACG | CATTTGAGT | ATTAACTATA | TAAGACCAAA | 2100 |
| ATTATATTTT | CATTTCTGT | TATATTATAC | TATATAATAA | AAACAAATAA | ATATACGAAT | 2160 |

| ATTATAAGAA | ATTTAGAACA | CGTTATTAAA | GTATTGCCTT | TTTTATTAAC | GGCGTGTTCT | 2220 |
| TGTAATTGCC | GTTTAGAATA | GTCTTTATTT | ACTTTAGATA | ACTCTTCTAT | CATAACCGTC | 2280 |
| TCCTTATTCC | AATCTTCTTC | AGAAGTACAT | GAGTACTTAC | CGAAGTTTAT | CATCATAGAG | 2340 |
| ATTATATATG | AAGAAA | | | | | 2356 |

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

| GACAATCTAA | GTCCTATATT | AGAC | 24 |

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

| GGATTTTTAG | GTAGACAC | 18 |

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

| TCATCGTCTT | CATCATCG | 18 |

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

| GTCTTAAACT | TATTGTAAGG | GTATACCTG | 29 |

(2) INFORMATION FOR SEQ ID NO:56:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

```
AACGATTAGT TAGTTACTAA AAGCTTGCTG CAGCCCGGGT TTTTTATTAG TTTAGTTAGT    60

C                                                                  61
```

( 2 ) INFORMATION FOR SEQ ID NO:57:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

```
GACTAACTAA CTAATAAAAA ACCCGGGCTG CAGCAAGCTT TTTGTAACTA ACTAATCGTT    60
```

( 2 ) INFORMATION FOR SEQ ID NO:58:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
GCACGGAACA AAGCTTATCG CGATATCCGT TAAGTTTGTA TCGTAATGCT ATCAATCACG    60

ATTCTGTTCC TGCTCATAGC AGAGGGCTCA TCTCAGAAT                           99
```

( 2 ) INFORMATION FOR SEQ ID NO:59:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

```
ATTCTGAGAT GAGCCCTCTG CTATGAGCAG GAACAGAATC GTGATTGATA GCATTACGAT    60

ACAAACTTAA CGGATATCGC GATAAGCTTT GTTCCGTGC                           99
```

( 2 ) INFORMATION FOR SEQ ID NO:60:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

```
GAAAAATTTA AAGTCGACCT GTTTGTTGA GTTGTTTGCG TGGTAACCAA TGCAAATCTG    60

GTCACT                                                              66
```

( 2 ) INFORMATION FOR SEQ ID NO:61:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

TCTAGCAAGA CTGACTATTG CAAAAAGAAG CACTATTTCC TCCATTACGA TACAAACTTA    60

ACGGAT    66

( 2 ) INFORMATION FOR SEQ ID NO:62:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:62:

ATCCGTTAAG TTTGTATCGT AATGGAGGAA ATAGTGCTTC TTTTTGCAAT AGTCAGTCTT    60

GCTAGAAGTG ACCAGATTTG CATTGGT    87

( 2 ) INFORMATION FOR SEQ ID NO:63:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:63:

TACCACGCAA ACAACTCAAC AAAACAGGTC GACTTAAAT TTTTCTGCA    49

( 2 ) INFORMATION FOR SEQ ID NO:64:

( i ) SEQUENCE CHARACTERISTICS:
    ( A ) LENGTH: 132 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:64:

GTACAGGTCG ACAAGCTTCC CGGGTATCGC GATATCCGTT AAGTTTGTAT CGTAATGAAT    60

ACTCAAATTC TAATACTCAC TCTTGTGGCA GCCATTCACA CAAATGCAGA CAAAATCTGC    120

CTTGGACATC AT    132

( 2 ) INFORMATION FOR SEQ ID NO:65:

( i ) SEQUENCE CHARACTERISTICS:
    ( A ) LENGTH: 132 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:65:

ATGATGTCCA AGGCAGATTT TGTCTGCATT TGTGTGAATG GCTGCCACAA GAGTGAGTAT    60

TAGAATTTGA GTATTCATTA CGATACAAAC TTAACGGATA TCGCGATACC CGGGAAGCTT    120

GTCGACCTGT AC    132

( 2 ) INFORMATION FOR SEQ ID NO:66:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:66:

ATAACATGCG GTGCACCATT TGTATATAAG TTAACGAATT CCAAGTCAAG C        51

( 2 ) INFORMATION FOR SEQ ID NO:67:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:67:

GCTTGACTTG GAATTCGTTA ACTTATATAC AAATGGTGCA CCGCATGTTA T        51

( 2 ) INFORMATION FOR SEQ ID NO:68:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:68:

CCAGGACATA GCAAGCCAAC AGGTC        25

( 2 ) INFORMATION FOR SEQ ID NO:69:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:69:

CGATATCCGT TAAGTTTGTA TCGTAATGCT CCCCTACCAA GAC        43

( 2 ) INFORMATION FOR SEQ ID NO:70:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:70:

GGGATAAAAA TTAACGGTTA CATGAGAATC TTATACGGAC        40

( 2 ) INFORMATION FOR SEQ ID NO:71:

( i ) SEQUENCE CHARACTERISTICS:
        ( A ) LENGTH: 45 base pairs
        ( B ) TYPE: nucleic acid
        ( C ) STRANDEDNESS: single -continued (D) TOPOLOGY: linear (i i) MOLECULE TYPE: cDNA (x i) SEQUENCE DESCRIPTION: SEQ ID NO:71:

GGGCTGAAGC TTGCTGGCCG CTCATTAGAC AAGCGAATGA GGGAC  45

(2) INFORMATION FOR SEQ ID NO:72:

(i) SEQUENCE CHARACTERISTICS:
(A) LENGTH: 62 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:72:

AGATCTCCCG GGCTCGAGTA ATTAATTAAT TTTATTACA CCAGAAAAGA CGGCTTGAGA  60

TC  62

(2) INFORMATION FOR SEQ ID NO:73:

(i) SEQUENCE CHARACTERISTICS:
(A) LENGTH: 64 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:73:

TAATTACTCG AGCCCGGGAG ATCTAATTTA ATTAATTTA TATAACTCAT TTTTGAATA  60

TACT  64

(2) INFORMATION FOR SEQ ID NO:74:

(i) SEQUENCE CHARACTERISTICS:
(A) LENGTH: 45 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:74:

TATCTCGAAT TCCCGCGGCT TTAAATGGAC GGAACTCTTT TCCCC  45

(2) INFORMATION FOR SEQ ID NO:75:

(i) SEQUENCE CHARACTERISTICS:
(A) LENGTH: 62 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:75:

GATCTTTTGT TAACAAAAAC TAATCAGCTA TCGCGAATCG ATTCCCGGGG GATCCGGTAC  60

CC  62

(2) INFORMATION FOR SEQ ID NO:76:

(i) SEQUENCE CHARACTERISTICS:
(A) LENGTH: 62 base pairs
(B) TYPE: nucleic acid (C) STRANDEDNESS: single
(D) TOPOLOGY: linear (i i) MOLECULE TYPE: cDNA (x i) SEQUENCE DESCRIPTION: SEQ ID NO:76:

TCGAGGGTAC CGGATCCCCC GGGAATCGAT TCGCGATAGC TGATTAGTTT TTGTTAACAA 60

AA 62

(2) INFORMATION FOR SEQ ID NO:77:

(i) SEQUENCE CHARACTERISTICS:
(A) LENGTH: 43 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:77:

CGATATCCGT TAAGTTTGTA TCGTAATCTG CAGCCCGGGG GGG 43

(2) INFORMATION FOR SEQ ID NO:78:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:78:

GATCCCCCGG GCTGCAGATT ACGATACAAA CTTAACGGAT ATCG 44

(2) INFORMATION FOR SEQ ID NO:79:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:79:

ATCATCAAGC TTGATTCTTT ATTCTATAC 29

(2) INFORMATION FOR SEQ ID NO:80:

(i) SEQUENCE CHARACTERISTICS:
(A) LENGTH: 36 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:80:

GTCTTGGTAG GGGAGCATTA CGATACAAAC TTAACG 36

(2) INFORMATION FOR SEQ ID NO:81:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:81:

ATGCTCCCCT ACCAAGAC                                                                            18

(2) INFORMATION FOR SEQ ID NO:82:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:82:

GTAATTAGTA AAATTCACCT TG                                                                       22

(2) INFORMATION FOR SEQ ID NO:83:

(i) SEQUENCE CHARACTERISTICS:
        (A) LENGTH: 1939 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:83:

```
TTCTTTATTC TATACTTAAA AAGTGAAAAT AAATACAAAG GTTCTTGAGG GTTGTGTTAA      60
ATTGAAAGCG AGAAATAATC ATAAATTATT TCATTATCGC GATATCCGTT AAGTTTGTAT     120
CGTAATGCTC CCCTACCAAG ACAAGGTGGG TGCCTTCTAC AAGGATAATG CAAGAGCCAA     180
TTCAACCAAG CTGTCCTTAG TGACAGAAGG ACATGGGGGC AGGAGACCAC CTTATTTGTT     240
GTTTGTCCTT CTCATCTTAT TGGTTGGTAT CCTGGCCTTG CTTGCTATCA CTGGAGTTCG     300
ATTTCACCAA GTATCAACTA GTAATATGGA ATTTAGCAGA TTGCTGAAAG AGGATATGGA     360
GAAATCAGAG GCCGTACATC ACCAAGTCAT AGATGTCTTG ACACCGCTCT TCAAGATTAT     420
TGGAGATGAG ATTGGGTTAC GGTTGCCACA AAAGCTAAAC GAGATCAAAC AATTTATCCT     480
TCAAAAGACA AATTTCTTCA ATCCGAACAG AGAATTCGAC TTCCGCGATC TCCACTGGTG     540
CATTAACCCG CCTAGTACGG TCAAGGTGAA TTTTACTAAT TACTGTGAGT CAATTGGGAT     600
CAGAAAAGCT ATTGCATCGG CAGCAAATCC TATCCTTTTA TCAGCCCTAT CTGGGGGCAG     660
AGGTGACATA TTCCCACCAC ACAGATGCAG TGGAGCTACT ACTTCAGTAG GCAAAGTTTT     720
CCCCCTATCA GTCTCATTAT CCATGTCTTT GATCTCAAGA ACCTCAGAGG TAATCAATAT     780
GCTGACCGCT ATCTCAGACG GCGTGTATGG CAAAACTTAC TTGCTAGTGC CTGATGATAT     840
AGAAAGAGAG TTCGACACTC GAGAGATTCG AGTCTTTGAA ATAGGGTTCA TCAAGAGGTG     900
GCTGAATGAC ATGCCATTAC TCCAAACAAC CAACTATATG GTACTCCCGA AGAATTCCAA     960
AGCCAAGGTA TGTACTATAG CAGTGGGTGA GTTGACACTG GCTTCCTTGT GTGTAGAAGA    1020
GAGCACTGTA TTATTATATC ATGACAGCAG TGGTTCACAA GATGGTATTC TAGTAGTGAC    1080
ACTGGGGATA TTTTGGGCAA CACCTATGGA TCACATTGAG GAAGTGATAC CTGTCGCTCA    1140
CCCATCAATG AAGAAAATAC ATATAACAAA CCACCGTGGT TTTATAAAAG ATTCAATTGC    1200
AACCTGGATG GTGCCTGCCC TGGCCTCTGA GAAACAAGAA GAACAAAAAG GTTGTCTGGA    1260
GTCAGCTTGT CAAAGAAAAA CCTACCCCAT GTGCAACCAA GCGTCATGGG AACCCTTCGG    1320
AGGAAGACAG TTGCCATCTT ATGGGCGGTT GACATTACCT CTAGATGCAA GTGTTGACCT    1380
```

-continued

```
TCAACTTAAC ATATCGTTCA CATACGGTCC GGTTATACTG AATGGAGATG GTATGGATTA    1440
TTATGAAAGC CCACTTTTGA ACTCCGGATG GCTTACCATT CCCCCCAAAG ACGGAACAAT    1500
CTCTGGATTG ATAAACAAAG CAGGTAGAGG AGACCAGTTC ACTGTACTCC CCATGTGTT    1560
AACATTTGCG CCCAGGGAAT CAAGTGGAAA TTGTTATTTA CCTATTCAAA CATCTCAAAT    1620
TAGAGATAGA GATGTCCTCA TTGAGTCCAA TATAGTGGTG TTGCCTACAC AGAGTATTAG    1680
ATATGTCATA GCAACGTATG ACATATCACG AAGTGATCAT GCTATTGTTT ATTATGTTTA    1740
TGACCCAATC CGGACGATTT CTTATACGCA CCCATTAGA CTAACTACCA AGGGTAGACC     1800
TGATTTCCTA AGGATTGAAT GTTTGTGTG GGATGACAAT TTGTGGTGTC ACCAATTTTA     1860
CAGATTCGAG GCTGACATCG CCAACTCTAC AACCAGTGTT GAGAATTTAG TCCGTATAAG    1920
ATTCTCATGT AACCGTTAA                                                  1939
```

( 2 ) INFORMATION FOR SEQ ID NO:84:

( i ) SEQUENCE CHARACTERISTICS:
        ( A ) LENGTH: 604 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:84:

```
Met Leu Pro Tyr Gln Asp Lys Val Gly Ala Phe Tyr Lys Asp Asn Ala
 1               5                  10                  15

Arg Ala Asn Ser Thr Lys Leu Ser Leu Val Thr Glu Gly His Gly Gly
            20                  25                  30

Arg Arg Pro Pro Tyr Leu Leu Phe Val Leu Leu Ile Leu Val Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Thr Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Val Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240
```

```
Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Lys Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Gln Lys Gly Cys Leu Glu Ser Ala Cys Gln Arg
    370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
    450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
    515                 520                 525

Arg Ser Asp His Ala Ile Val Tyr Tyr Val Tyr Asp Pro Ile Arg Thr
530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600
```

( 2 ) INFORMATION FOR SEQ ID NO:85:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:85:

| | | | | | |
|---|---|---|---|---|---|
| CATAAATTAT | TTCATTATCG | CGATATCCGT | TAAGTTTGTA | TCGTAATGCA | CAAGGGAATC | 60
| CCCAAAAGC | | | | | 69

( 2 ) INFORMATION FOR SEQ ID NO:86:

( i ) SEQUENCE CHARACTERISTICS:
  ( A ) LENGTH: 48 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:86:

ATCATCGGAT CCATAAAAAT CAGTGTGATC TCACATAGGA TTTCGAAG    48

( 2 ) INFORMATION FOR SEQ ID NO:87:

( i ) SEQUENCE CHARACTERISTICS:
  ( A ) LENGTH: 2113 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:87:

| | | | | | |
|---|---|---|---|---|---|
| TTCTTTATTC | TATACTTAAA | AAGTGAAAAT | AAATACAAAG | GTTCTTGAGG | GTTGTGTTAA | 60
| ATTGAAAGCG | AGAAATAATC | ATAAATTATT | TCATTATCGC | GATATCCGTT | AAGTTTGTAT | 120
| CGTAATGCAC | AAGGGAATCC | CCAAAAGCTC | CAAAACCCAA | ACACATACCC | AACAAGACCG | 180
| CCCCCCACAA | CCCAGCACCG | AACTCGAAGA | GACCAGGACC | TCCCGAGCAC | GACACAGCAC | 240
| AACATCAGCT | CAGCGATCCA | CGCACTACGA | TCCTCGAACA | TCGGACAGAC | CCGTCTCCTA | 300
| CACCATGAAC | AGGACCAGGT | CCCGCAAGCA | AACCAGCCAC | AGATTGAAGA | ACATCCCAGT | 360
| TCACGGAAAC | CACGAGGCCA | CCATCCAGCA | CATACCAGAG | AGTGTCTCAA | AAGGAGCGAG | 420
| ATCCCAGATC | GAAAGGCGGC | AACCCAATGC | AATCAACTCA | GGCTCTCATT | GCACCTGGTT | 480
| AGTCCTGTGG | TGCCTCGGAA | TGGCCAGTCT | CTTTCTTTGT | TCCAAGGCTC | AGATACATTG | 540
| GAATAATTTG | TCAACTATTG | GGATTATCGG | GACTGATAGT | GTCCATTACA | AGATCATGAC | 600
| TAGGCCCAGT | CACCAGTACT | TGGTCATAAA | ACTGATGCCT | AATGTTTCAC | TTATAGAGAA | 660
| TTGTACCAAA | GCAGAATTAG | GTGAGTATGA | GAAATTATTG | AATTCAGTCC | TCGAACCAAT | 720
| CAACCAAGCT | TTGACTCTAA | TGACCAAGAA | TGTGAAGCCC | CTGCAGTCAT | TAGGGTCAGG | 780
| TAGGAGACAA | AGGCGTTTTG | CAGGAGTGGT | ACTTGCAGGT | GTAGCTTTAG | GAGTGGCTAC | 840
| AGCTGCACAA | ATCACTGCAG | GAATAGCTTT | ACATCAATCC | AACCTCAATG | CTCAAGCAAT | 900
| CCAATCTCTT | AGAACCAGCC | TTGAACAGTC | TAACAAAGCT | ATAGAAGAAA | TTAGGGAGGC | 960
| TACCCAAGAA | ACCGTCATTG | CCGTTCAGGG | AGTCCAGGAC | TACGTCAACA | ACGAACTCGT | 1020
| CCCTGCCATG | CAACATATGT | CATGTGAATT | AGTTGGGCAG | AGATTAGGGT | TAAGACTGCT | 1080
| TCGGTATTAT | ACTGAGTTGT | TGTCAATATT | TGGCCCGAGT | TTACGTGACC | CTATTTCAGC | 1140
| CGAGATATCA | ATTCAGGCAC | TGATTTATGC | TCTTGGAGGA | GAAATTCATA | AGATACTTGG | 1200
| GAAGTTGGGA | TATTCTGGAA | GTGATATGAT | TGCAATCTTG | GAGAGTCGGG | GGATAAAAAC | 1260
| AAAAATAACT | CATGTTGATC | TTCCCGGGAA | ATTCATCATC | CTAAGTATCT | CATACCCAAC | 1320
| TTTATCAGAA | GTCAAGGGGG | TTATAGTCCA | CAGACTGGAA | GCGGTTTCTT | ACAACATAGG | 1380

-continued

```
ATCACAAGAG  TGGTACACCA  CTGTCCCGAG  GTATATTGCA  ACTAATGGTT  ACTTAATATC   1440
TAATTTTGAT  GAGTCATCTT  GTGTATTCGT  CTCAGAGTCA  GCCATTTGTA  GCCAGAACTC   1500
CCTGTATCCC  ATGAGCCCAC  TCTTACAACA  ATGTATTAGG  GGCGACACTT  CATCTTGTGC   1560
TCGGACCTTG  GTATCTGGGA  CTATGGGCAA  CAAATTTATT  CTGTCAAAAG  GTAATATCGT   1620
CGCAAATTGT  GCTTCTATAC  TATGTAAGTG  TTATAGCACA  AGCACAATTA  TTAATCAGAG   1680
TCCTGATAAG  TTGCTGACAT  TCATTGCCTC  CGATACCTGC  CCACTGGTTG  AAATAGATGG   1740
TGCTACTATC  CAAGTTGGAG  GCAGGCAATA  CCCTGATATG  GTATACGAAG  GCAAAGTTGC   1800
CTTAGGCCCT  GCTATATCAC  TTGATAGGTT  AGATGTAGGT  ACAAACTTAG  GGAACGCCCT   1860
TAAGAAACTG  GATGATGCTA  AGGTACTGAT  AGACTCCTCT  AACCAGATCC  TTGAGACGGT   1920
TAGGCGCTCT  TCCTTCAATT  TTGGCAGTCT  CCTCAGCGTT  CCTATATTAA  GTTGTACAGC   1980
CCTGGCTTTG  TTGTTGCTGA  TTTACTGTTG  TAAAAGACGC  TACCAACAGA  CACTCAAGCA   2040
GCATACTAAG  GTCGATCCGG  CATTTAAACC  TGATCTAACT  GGAACTTCGA  AATCCTATGT   2100
GAGATCACAC  TGA                                                          2113
```

( 2 ) INFORMATION FOR SEQ ID NO:88:

( i ) SEQUENCE CHARACTERISTICS:
        ( A ) LENGTH: 662 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:88:

```
Met His Lys Gly Ile Pro Lys Ser Ser Lys Thr Gln Thr His Thr Gln
 1               5                  10                  15

Gln Asp Arg Pro Pro Gln Pro Ser Thr Glu Leu Glu Glu Thr Arg Thr
                20                  25                  30

Ser Arg Ala Arg His Ser Thr Thr Ser Ala Gln Arg Ser Thr His Tyr
            35                  40                  45

Asp Pro Arg Thr Ser Asp Arg Pro Val Ser Tyr Thr Met Asn Arg Thr
        50                  55                  60

Arg Ser Arg Lys Gln Thr Ser His Arg Leu Lys Asn Ile Pro Val His
65                  70                  75                  80

Gly Asn His Glu Ala Thr Ile Gln His Ile Pro Glu Ser Val Ser Lys
                85                  90                  95

Gly Ala Arg Ser Gln Ile Glu Arg Arg Gln Pro Asn Ala Ile Asn Ser
               100                 105                 110

Gly Ser His Cys Thr Trp Leu Val Leu Trp Cys Leu Gly Met Ala Ser
           115                 120                 125

Leu Phe Leu Cys Ser Lys Ala Gln Ile His Trp Asn Asn Leu Ser Thr
       130                 135                 140

Ile Gly Ile Ile Gly Thr Asp Ser Val His Tyr Lys Ile Met Thr Arg
145                 150                 155                 160

Pro Ser His Gln Tyr Leu Val Ile Lys Leu Met Pro Asn Val Ser Leu
                165                 170                 175

Ile Glu Asn Cys Thr Lys Ala Glu Leu Gly Glu Tyr Glu Lys Leu Leu
            180                 185                 190

Asn Ser Val Leu Glu Pro Ile Asn Gln Ala Leu Thr Leu Met Thr Lys
        195                 200                 205
```

```
Asn Val Lys Pro Leu Gln Ser Leu Gly Ser Gly Arg Arg Gln Arg Arg
    210             215             220

Phe Ala Gly Val Val Leu Ala Gly Val Ala Leu Gly Val Ala Thr Ala
225             230             235                     240

Ala Gln Ile Thr Ala Gly Ile Ala Leu His Gln Ser Asn Leu Asn Ala
            245             250                     255

Gln Ala Ile Gln Ser Leu Arg Thr Ser Leu Glu Gln Ser Asn Lys Ala
            260             265             270

Ile Glu Glu Ile Arg Glu Ala Thr Gln Glu Thr Val Ile Ala Val Gln
            275             280             285

Gly Val Gln Asp Tyr Val Asn Asn Glu Leu Val Pro Ala Met Gln His
    290             295             300

Met Ser Cys Glu Leu Val Gly Gln Arg Leu Gly Leu Arg Leu Leu Arg
305             310             315             320

Tyr Tyr Thr Glu Leu Leu Ser Ile Phe Gly Pro Ser Leu Arg Asp Pro
            325             330             335

Ile Ser Ala Glu Ile Ser Ile Gln Ala Leu Ile Tyr Ala Leu Gly Gly
            340             345             350

Glu Ile His Lys Ile Leu Gly Lys Leu Gly Tyr Ser Gly Ser Asp Met
            355             360             365

Ile Ala Ile Leu Glu Ser Arg Gly Ile Lys Thr Lys Ile Thr His Val
    370             375             380

Asp Leu Pro Gly Lys Phe Ile Ile Leu Ser Ile Ser Tyr Pro Thr Leu
385             390             395             400

Ser Glu Val Lys Gly Val Ile Val His Arg Leu Glu Ala Val Ser Tyr
            405             410             415

Asn Ile Gly Ser Gln Glu Trp Tyr Thr Thr Val Pro Arg Tyr Ile Ala
            420             425             430

Thr Asn Gly Tyr Leu Ile Ser Asn Phe Asp Glu Ser Ser Cys Val Phe
            435             440             445

Val Ser Glu Ser Ala Ile Cys Ser Gln Asn Ser Leu Tyr Pro Met Ser
    450             455             460

Pro Leu Leu Gln Gln Cys Ile Arg Gly Asp Thr Ser Ser Cys Ala Arg
465             470             475             480

Thr Leu Val Ser Gly Thr Met Gly Asn Lys Phe Ile Leu Ser Lys Gly
            485             490             495

Asn Ile Val Ala Asn Cys Ala Ser Ile Leu Cys Lys Cys Tyr Ser Thr
            500             505             510

Ser Thr Ile Ile Asn Gln Ser Pro Asp Lys Leu Leu Thr Phe Ile Ala
        515             520             525

Ser Asp Thr Cys Pro Leu Val Glu Ile Asp Gly Ala Thr Ile Gln Val
    530             535             540

Gly Gly Arg Gln Tyr Pro Asp Met Val Tyr Glu Gly Lys Val Ala Leu
545             550             555             560

Gly Pro Ala Ile Ser Leu Asp Arg Leu Asp Val Gly Thr Asn Leu Gly
            565             570             575

Asn Ala Leu Lys Lys Leu Asp Asp Ala Lys Val Leu Ile Asp Ser Ser
            580             585             590

Asn Gln Ile Leu Glu Thr Val Arg Arg Ser Ser Phe Asn Phe Gly Ser
        595             600             605

Leu Leu Ser Val Pro Ile Leu Ser Cys Thr Ala Leu Ala Leu Leu Leu
    610             615             620

Leu Ile Tyr Cys Cys Lys Arg Arg Tyr Gln Gln Thr Leu Lys Gln His
625             630             635             640
```

```
          Thr  Lys  Val  Asp  Pro  Ala  Phe  Lys  Pro  Asp  Leu  Thr  Gly  Thr  Ser  Lys
                         645                      650                      655

Ser  Tyr  Val  Arg  Ser  His
                         660
```

( 2 ) INFORMATION FOR SEQ ID NO:89:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:89:

```
AGCTTCCCGG  GTTAATTAAT  TAGTCATCAG  GCAGGGCGAG  AACGAGACTA  TCTGCTCGTT        60

AATTAATTAG                                                                    70
```

( 2 ) INFORMATION FOR SEQ ID NO:90:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:90:

```
AGCTCTAATT  AATTAACGAG  CAGATAGTCT  CGTTCTCGCC  CTGCCTGATG  ACTAATTAAT        60

TAACCCGGGA                                                                    70
```

( 2 ) INFORMATION FOR SEQ ID NO:91:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:91:

```
AGAAAAATCA  GTTAGCTAAG  ATCTCCCGGG  CTCGAGGGTA  CCGGATCCTG  ATTAGTTAAT        60

TTTTGT                                                                        66
```

( 2 ) INFORMATION FOR SEQ ID NO:92:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:92:

```
GATCACAAAA  ATTAACTAAT  CAGGATCCGG  TACCCTCGAG  CCCGGGAGAT  CTTAGCTAAC        60

TGATTTTTCT                                                                    70
```

( 2 ) INFORMATION FOR SEQ ID NO:93:

( i ) SEQUENCE CHARACTERISTICS:
    ( A ) LENGTH: 4343 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:93:

```
TTTGTAATAT AATGATATAT ATTTTCACTT TATCTCATTT GAGAATAAAA AGATCACAAA    60
AATTAACTAA TCAGGATCCA TAAAAATCAG TGTGATCTCA CATAGGATTT CGAAGTTCCA   120
GTTAGATCAG GTTTAAATGC CGGATCGACC TTAGTATGCT GCTTGAGTGT CTGTTGGTAG   180
CGTCTTTTAC AACAGTAAAT CAGCAACAAC AAAGCCAGGG CTGTACAACT TAATATAGGA   240
ACGCTGAGGA GACTGCCAAA ATTGAAGGAA GAGCGCCTAA CCGTCTCAAG GATCTGGTTA   300
GAGGAGTCTA TCAGTACCTT AGCATCATCC AGTTTCTTAA GGGCGTTCCC TAAGTTTGTA   360
CCTACATCTA ACCTATCAAG TGATATAGCA GGGCCTAAGG CAACTTGCC TTCGTATACC    420
ATATCAGGGT ATTGCCTGCC TCCAACTTGG ATAGTAGCAC CATCTATTTC AACCAGTGGG   480
CAGGTATCGG AGGCAATGAA TGTCAGCAAC TTATCAGGAC TCTGATTAAT AATTGTGCTT   540
GTGCTATAAC ACTTACATAG TATAGAAGCA CAATTGCGA CGATATTACC TTTTGACAGA    600
ATAAATTTGT TGCCCATAGT CCCAGATACC AAGGTCCGAG CACAAGATGA AGTGTCGCCC   660
CTAATACATT GTTGTAAGAG TGGGCTCATG GGATACAGGG AGTTCTGGCT ACAAATGGCT   720
GACTCTGAGA CGAATACACA AGATGACTCA TCAAAATTAG ATATTAAGTA ACCATTAGTT   780
GCAATATACC TCGGGACAGT GGTGTACCAC TCTTGTGATC CTATGTTGTA AGAAACCGCT   840
TCCAGTCTGT GGACTATAAC CCCCTTGACT TCTGATAAAG TTGGGTATGA GATACTTAGG   900
ATGATGAATT TCCCGGGAAG ATCAACATGA GTTATTTTG TTTTATCCC CCGACTCTCC     960
AAGATTGCAA TCATATCACT TCCAGAATAT CCCAACTTCC CAAGTATCTT ATGAATTTCT  1020
CCTCCAAGAG CATAAATCAG TGCCTGAATT GATATCTCGG CTGAAATAGG GTCACGTAAA  1080
CTCGGGCCAA ATATTGACAA CAACTCAGTA TAATACCGAA GCAGTCTTAA CCCTAATCTC  1140
TGCCCAACTA ATTCACATGA CATATGTTGC ATGGCAGGGA CGAGTTCGTT GTTGACGTAG  1200
TCCTGGACTC CCTGAACGGC AATGACGGTT TCTTGGGTAG CCTCCCTAAT TTCTTCTATA  1260
GCTTTGTTAG ACTGTTCAAG GCTGGTTCTA AGAGATTGGA TTGCTTGAGC ATTGAGGTTG  1320
GATTGATGTA AAGCTATTCC TGCAGTGATT TGTGCAGCTG TAGCCACTCC TAAAGCTACA  1380
CCTGCAAGTA CCACTCCTGC AAAACGCCTT TGTCTCCTAC CTGACCCTAA TGACTGCAGG  1440
GGCTTCACAT TCTTGGTCAT TAGAGTCAAA GCTTGGTTGA TTGGTTCGAG GACTGAATTC  1500
AATAATTTCT CATACTCACC TAATTCTGCT TTGGTACAAT TCTCTATAAG TGAAACATTA  1560
GGCATCAGTT TTATGACCAA GTACTGGTGA CTGGGCCTAG TCATGATCTT GTAATGGACA  1620
CTATCAGTCC CGATAATCCC AATAGTTGAC AAATTATTCC AATGTATCTG AGCCTTGGAA  1680
CAAAGAAAGA GACTGGCCAT TCCGAGGCAC CACAGGACTA ACCAGGTGCA ATGAGAGCCT  1740
GAGTTGATTG CATTGGGTTG CCGCCTTTCG ATCTGGGATC TCGCTCCTTT TGAGACACTC  1800
TCTGGTATGT GCTGGATGGT GGCCTCGTGG TTTCCGTGAA CTGGGATGTT CTTCAATCTG  1860
TGGCTGGTTT GCTTGCGGGA CCTGGTCCTG TTCATGGTGT AGGAGACGGG TCTGTCCGAT  1920
GTTCGAGGAT CGTAGTGCGT GGATCGCTGA GCTGATGTTG TGCTGTGTCG TGCTCGGGAG  1980
GTCCTGGTCT CTTCGAGTTC GGTGCTGGGT TGTGGGGGGC GGTCTTGTTG GGTATGTGTT  2040
TGGGTTTTGG AGCTTTTGGG GATTCCCTTG TGCATTACGA TACAAACTTA ACGGATATCG  2100
CGATAATGAA ATAATTTATG ATTATTTCTC GCTTTCAATT TAACACAACC CTCAAGAACC  2160
```

| | | | | | |
|---|---|---|---|---|---|
| TTTGTATTTA | TTTTCACTTT | TTAAGTATAG | AATAAAGAAG | CTCTAATTAA | TTAAGCTACA | 2220
| AATAGTTTCG | TTTTCACCTT | GTCTAATAAC | TAATTAATTA | ACCCGGATCC | GGTACCCTCG | 2280
| AGCCCGGGTT | AATTAATTAG | TCATCAGGCA | GGGCGAGAAC | GAGACTATCT | GCTCGTTAAT | 2340
| TAATTAGAGC | TTGATTCTTT | ATTCTATACT | TAAAAAGTGA | AATAAATAC | AAAGGTTCTT | 2400
| GAGGGTTGTG | TTAAATTGAA | AGCGAGAAAT | AATCATAAAT | TATTTCATTA | TCGCGATATC | 2460
| CGTTAAGTTT | GTATCGTAAT | GCTCCCCTAC | CAAGACAAGG | TGGGTGCCTT | CTACAAGGAT | 2520
| AATGCAAGAG | CCAATTCAAC | CAAGCTGTCC | TTAGTGACAG | AAGGACATGG | GGCAGGAGA | 2580
| CCACCTTATT | TGTTGTTTGT | CCTTCTCATC | TTATTGGTTG | GTATCCTGGC | CTTGCTTGCT | 2640
| ATCACTGGAG | TTCGATTTCA | CCAAGTATCA | ACTAGTAATA | TGGAATTTAG | CAGATTGCTG | 2700
| AAAGAGGATA | TGGAGAAATC | AGAGGCCGTA | CATCACCAAG | TCATAGATGT | CTTGACACCG | 2760
| CTCTTCAAGA | TTATTGGAGA | TGAGATTGGG | TTACGGTTGC | CACAAAAGCT | AAACGAGATC | 2820
| AAACAATTTA | TCCTTCAAAA | GACAAATTTC | TTCAATCCGA | ACAGAGAATT | CGACTTCCGC | 2880
| GATCTCCACT | GGTGCATTAA | CCCGCCTAGT | ACGGTCAAGG | TGAATTTTAC | TAATTACTGT | 2940
| GAGTCAATTG | GGATCAGAAA | AGCTATTGCA | TCGGCAGCAA | ATCCTATCCT | TTTATCAGCC | 3000
| CTATCTGGGG | GCAGAGGTGA | CATATTCCCA | CCACACAGAT | GCAGTGGAGC | TACTACTTCA | 3060
| GTAGGCAAAG | TTTTCCCCCT | ATCAGTCTCA | TTATCCATGT | CTTTGATCTC | AAGAACCTCA | 3120
| GAGGTAATCA | ATATGCTGAC | CGCTATCTCA | GACGGCGTGT | ATGGCAAAAC | TTACTTGCTA | 3180
| GTGCCTGATG | ATATAGAAAG | AGAGTTCGAC | ACTCGAGAGA | TTCGAGTCTT | TGAAATAGGG | 3240
| TTCATCAAGA | GGTGGCTGAA | TGACATGCCA | TTACTCCAAA | CAACCAACTA | TATGGTACTC | 3300
| CCGAAGAATT | CCAAAGCCAA | GGTATGTACT | ATAGCAGTGG | GTGAGTTGAC | ACTGGCTTCC | 3360
| TTGTGTGTAG | AAGAGAGCAC | TGTATTATTA | TATCATGACA | GCAGTGGTTC | ACAAGATGGT | 3420
| ATTCTAGTAG | TGACACTGGG | GATATTTTGG | GCAACACCTA | TGGATCACAT | TGAGGAAGTG | 3480
| ATACCTGTCG | CTCACCCATC | AATGAAGAAA | ATACATATAA | CAAACCACCG | TGGTTTTATA | 3540
| AAAGATTCAA | TTGCAACCTG | GATGGTGCCT | GCCCTGGCCT | CTGAGAAACA | AGAAGAACAA | 3600
| AAAGGTTGTC | TGGAGTCAGC | TTGTCAAAGA | AAAACCTACC | CCATGTGCAA | CCAAGCGTCA | 3660
| TGGGAACCCT | TCGGAGGAAG | ACAGTTGCCA | TCTTATGGGC | GGTTGACATT | ACCTCTAGAT | 3720
| GCAAGTGTTG | ACCTTCAACT | TAACATATCG | TTCACATACG | GTCCGGTTAT | ACTGAATGGA | 3780
| GATGGTATGG | ATTATTATGA | AAGCCCACTT | TTGAACTCCG | GATGGCTTAC | CATTCCCCCC | 3840
| AAAGACGGAA | CAATCTCTGG | ATTGATAAAC | AAAGCAGGTA | GAGGAGACCA | GTTCACTGTA | 3900
| CTCCCCCATG | TGTTAACATT | TGCGCCCAGG | GAATCAAGTG | GAAATTGTTA | TTTACCTATT | 3960
| CAAACATCTC | AAATTAGAGA | TAGAGATGTC | CTCATTGAGT | CCAATATAGT | GGTGTTGCCT | 4020
| ACACAGAGTA | TTAGATATGT | CATAGCAACG | TATGACATAT | CACGAAGTGA | TCATGCTATT | 4080
| GTTTATTATG | TTTATGACCC | AATCCGGACG | ATTTCTTATA | CGCACCCATT | TAGACTAACT | 4140
| ACCAAGGGTA | GACCTGATTT | CCTAAGGATT | GAATGTTTTG | TGTGGGATGA | CAATTTGTGG | 4200
| TGTCACCAAT | TTACAGATT | CGAGGCTGAC | ATCGCCAACT | CTACAACCAG | TGTTGAGAAT | 4260
| TTAGTCCGTA | TAAGATTCTC | ATGTAACCGT | TAATTTTTAT | CCCGGGAGAT | CTTAGCTAAC | 4320
| TGATTTTTCT | GGGAAAAAAA | TTA | | | | 4343

( 2 ) INFORMATION FOR SEQ ID NO:94:

( i ) SEQUENCE CHARACTERISTICS:
( A ) LENGTH: 662 amino acids
( B ) TYPE: amino acid ( C ) STRANDEDNESS: single
( D ) TOPOLOGY: linear ( i i ) MOLECULE TYPE: peptide ( v ) FRAGMENT TYPE: internal ( x i ) SEQUENCE DESCRIPTION: SEQ ID NO:94:

```
His Ser Arg Val Tyr Ser Lys Ser Thr Gly Thr Leu Asp Pro Lys Phe
1               5                   10                  15

Ala Pro Asp Val Lys Thr His Gln Lys Leu Thr Gln Gln Tyr Arg Arg
                20                  25                  30

Lys Cys Cys Tyr Ile Leu Leu Leu Leu Ala Leu Ala Thr Cys Ser Leu
            35                  40                  45

Ile Pro Val Ser Leu Leu Ser Gly Phe Asn Phe Ser Ser Arg Arg Val
        50                  55                  60

Thr Glu Leu Ile Gln Asn Ser Ser Asp Ile Leu Val Lys Ala Asp Asp
65                  70                  75                  80

Leu Lys Lys Leu Ala Asn Gly Leu Asn Thr Gly Val Asp Leu Arg Asp
                85                  90                  95

Leu Ser Ile Ala Pro Gly Leu Ala Val Lys Gly Glu Tyr Val Met Asp
            100                 105                 110

Pro Tyr Gln Arg Gly Gly Val Gln Ile Thr Ala Gly Asp Ile Glu Val
        115                 120                 125

Leu Pro Cys Thr Asp Ser Ala Ile Phe Thr Leu Leu Lys Asp Pro Ser
    130                 135                 140

Gln Asn Ile Ile Thr Ser Thr Ser Tyr Cys Lys Cys Leu Ile Ser Ala
145                 150                 155                 160

Cys Asn Ala Val Ile Asn Gly Lys Ser Leu Ile Phe Lys Asn Gly Met
                165                 170                 175

Thr Gly Ser Val Leu Thr Arg Ala Cys Ser Ser Thr Asp Gly Arg Ile
            180                 185                 190

Cys Gln Gln Leu Leu Pro Ser Met Pro Tyr Leu Ser Asn Gln Ser Cys
        195                 200                 205

Ile Ala Ser Glu Ser Val Phe Val Cys Ser Ser Glu Asp Phe Asn Ser
    210                 215                 220

Ile Leu Tyr Gly Asn Thr Ala Ile Tyr Arg Pro Val Thr Thr Tyr Trp
225                 230                 235                 240

Glu Gln Ser Gly Ile Asn Tyr Ser Val Ala Glu Leu Arg His Val Ile
                245                 250                 255

Val Gly Lys Val Glu Ser Leu Thr Pro Tyr Ser Ile Ser Leu Ile Ile
            260                 265                 270

Phe Lys Gly Pro Leu Asp Val His Thr Ile Lys Thr Lys Ile Gly Arg
        275                 280                 285

Ser Glu Leu Ile Ala Ile Met Asp Ser Gly Ser Tyr Gly Leu Lys Gly
    290                 295                 300

Leu Ile Lys His Ile Glu Gly Gly Leu Ala Tyr Ile Leu Ala Gln Ile
305                 310                 315                 320

Ser Ile Glu Ala Ser Ile Pro Asp Arg Leu Ser Pro Gly Phe Ile Ser
                325                 330                 335

Leu Leu Glu Thr Tyr Tyr Arg Leu Leu Arg Leu Gly Leu Arg Gln Gly
            340                 345                 350

Val Leu Glu Cys Ser Met His Gln Met Ala Pro Val Leu Glu Asn Asn
        355                 360                 365

Val Tyr Asp Gln Val Gly Gln Val Ala Ile Val Thr Glu Gln Thr Ala
    370                 375                 380
```

| Glu<br>385 | Arg | Ile | Glu | Glu<br>390 | Ile | Ala | Lys | Asn | Ser<br>395 | Gln | Glu | Leu | Ser | Thr | Arg<br>400 |
|---|---|---|---|---|---|---|---|---|---|---|---|---|---|---|---|
| Leu | Ser | Gln | Ile | Ala<br>405 | Gln | Ala | Asn | Leu | Asn<br>410 | Ser | Gln | His | Leu | Ala<br>415 | Ile |
| Gly | Ala | Thr | Ile<br>420 | Gln | Ala | Ala | Thr | Ala<br>425 | Val | Gly | Leu | Ala | Val<br>430 | Gly | Ala |
| Leu | Val | Val<br>435 | Gly | Ala | Phe | Arg | Arg<br>440 | Gln | Arg | Arg | Gly | Ser<br>445 | Gly | Leu | Ser |
| Gln | Leu | Pro<br>450 | Lys | Val | Asn | Lys<br>455 | Thr | Met | Leu | Thr | Leu<br>460 | Ala | Gln | Asn | Ile |
| Pro<br>465 | Glu | Leu | Val | Ser | Asn<br>470 | Leu | Leu | Lys | Glu | Tyr<br>475 | Glu | Gly | Leu | Glu | Ala<br>480 |
| Lys | Thr | Cys | Asn | Glu<br>485 | Ile | Leu | Ser | Val | Asn<br>490 | Pro | Met | Leu | Lys | Ile<br>495 | Val |
| Leu | Tyr | Gln | His<br>500 | Ser | Pro | Arg | Thr | Met<br>505 | Ile | Lys | Tyr | His | Val<br>510 | Ser | Asp |
| Thr | Gly | Ile | Ile<br>515 | Gly | Ile | Thr | Ser<br>520 | Leu | Asn | Asn | Trp | His<br>525 | Ile | Gln | Ala |
| Lys | Ser<br>530 | Cys | Leu | Phe | Leu | Ser<br>535 | Ala | Met | Gly | Leu | Cys<br>540 | Trp | Leu | Val | Leu |
| Trp<br>545 | Thr | Cys | His | Ser | Gly<br>550 | Ser | Asn | Ile | Ala | Asn<br>555 | Pro | Gln | Arg | Arg | Glu<br>560 |
| Ile | Gln | Ser | Arg | Ala<br>565 | Gly | Lys | Ser | Val | Ser<br>570 | Glu | Pro | Ile | His | Gln<br>575 | Ile |
| Thr | Ala | Glu | His<br>580 | Asn | Gly | His | Val | Pro<br>585 | Ile | Asn | Lys | Leu | Arg<br>590 | His | Ser |
| Thr | Gln | Lys<br>595 | Arg | Ser | Arg | Thr | Arg<br>600 | Asn | Met | Thr | Tyr | Ser<br>605 | Val | Pro | Arg |
| Asp | Ser | Thr<br>610 | Arg | Pro | Asp | Tyr | His<br>615 | Thr | Ser | Arg | Gln | Ala<br>620 | Ser | Thr | Thr |
| Ser<br>625 | His | Arg | Ala | Arg | Ser<br>630 | Thr | Arg | Thr | Glu | Glu<br>635 | Leu | Glu | Thr | Ser | Pro<br>640 |
| Gln | Pro | Pro | Arg | Asp<br>645 | Gln | Gln | Thr | His | Thr<br>650 | Gln | Thr | Lys | Ser | Ser<br>655 | Lys |
| Pro | Ile | Gly | Lys | His<br>660 | Met | | | | | | | | | | |

( 2 ) INFORMATION FOR SEQ ID NO:95:

( i ) SEQUENCE CHARACTERISTICS:
        ( A ) LENGTH: 604 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:95:

| Met<br>1 | Leu | Pro | Tyr | Gln<br>5 | Asp | Lys | Val | Gly | Ala<br>10 | Phe | Tyr | Lys | Asp | Asn<br>15 | Ala |
|---|---|---|---|---|---|---|---|---|---|---|---|---|---|---|---|
| Arg | Ala | Asn | Ser | Thr<br>20 | Lys | Leu | Ser | Leu | Val<br>25 | Thr | Glu | Gly | His<br>30 | Gly | Gly |
| Arg | Arg | Pro | Pro<br>35 | Tyr | Leu | Leu | Phe | Val<br>40 | Leu | Leu | Ile | Leu | Leu<br>45 | Val | Gly |
| Ile | Leu | Ala | Leu | Leu | Ala | Ile | Thr | Gly | Val | Arg | Phe | His | Gln | Val | Ser |

```
                    50                          55                          60
Thr  Ser  Asn  Met  Glu  Phe  Ser  Arg  Leu  Leu  Lys  Glu  Asp  Met  Glu  Lys
 65            70                       75                           80

Ser  Glu  Ala  Val  His  His  Gln  Val  Ile  Asp  Val  Leu  Thr  Pro  Leu  Phe
                     85                       90                       95

Lys  Ile  Ile  Gly  Asp  Glu  Ile  Gly  Leu  Arg  Leu  Pro  Gln  Lys  Leu  Asn
               100                      105                      110

Glu  Ile  Lys  Gln  Phe  Ile  Leu  Gln  Lys  Thr  Asn  Phe  Phe  Asn  Pro  Asn
               115                      120                      125

Arg  Glu  Phe  Asp  Phe  Arg  Asp  Leu  His  Trp  Cys  Ile  Asn  Pro  Pro  Ser
          130                      135                      140

Thr  Val  Lys  Val  Asn  Phe  Thr  Asn  Tyr  Cys  Glu  Ser  Ile  Gly  Ile  Arg
145                      150                      155                      160

Lys  Ala  Ile  Ala  Ser  Ala  Ala  Asn  Pro  Ile  Leu  Leu  Ser  Ala  Leu  Ser
                    165                      170                      175

Gly  Gly  Arg  Gly  Asp  Ile  Phe  Pro  Pro  His  Arg  Cys  Ser  Gly  Ala  Thr
               180                      185                      190

Thr  Ser  Val  Gly  Lys  Val  Phe  Pro  Leu  Ser  Val  Ser  Leu  Ser  Met  Ser
               195                      200                      205

Leu  Ile  Ser  Arg  Thr  Ser  Glu  Val  Ile  Asn  Met  Leu  Thr  Ala  Ile  Ser
     210                      215                      220

Asp  Gly  Val  Tyr  Gly  Lys  Thr  Tyr  Leu  Leu  Val  Pro  Asp  Asp  Ile  Glu
225                      230                      235                      240

Arg  Glu  Phe  Asp  Thr  Arg  Glu  Ile  Arg  Val  Phe  Glu  Ile  Gly  Phe  Ile
                    245                      250                      255

Lys  Arg  Trp  Leu  Asn  Asp  Met  Pro  Leu  Leu  Gln  Thr  Thr  Asn  Tyr  Met
               260                      265                      270

Val  Leu  Pro  Lys  Asn  Ser  Lys  Ala  Lys  Val  Cys  Thr  Ile  Ala  Val  Gly
          275                      280                      285

Glu  Leu  Thr  Leu  Ala  Ser  Leu  Cys  Val  Glu  Glu  Ser  Thr  Val  Leu  Leu
          290                      295                      300

Tyr  His  Asp  Ser  Ser  Gly  Ser  Gln  Asp  Gly  Ile  Leu  Val  Val  Thr  Leu
305                      310                      315                      320

Gly  Ile  Phe  Trp  Ala  Thr  Pro  Met  Asp  His  Ile  Glu  Glu  Val  Ile  Pro
                    325                      330                      335

Val  Ala  His  Pro  Ser  Met  Lys  Lys  Ile  His  Ile  Thr  Asn  His  Arg  Gly
               340                      345                      350

Phe  Ile  Lys  Asp  Ser  Ile  Ala  Thr  Trp  Met  Val  Pro  Ala  Leu  Ala  Ser
          355                      360                      365

Glu  Lys  Gln  Glu  Glu  Gln  Lys  Gly  Cys  Leu  Glu  Ser  Ala  Cys  Gln  Arg
     370                      375                      380

Lys  Thr  Tyr  Pro  Met  Cys  Asn  Gln  Ala  Ser  Trp  Glu  Pro  Phe  Gly  Gly
385                      390                      395                      400

Arg  Gln  Leu  Pro  Ser  Tyr  Gly  Arg  Leu  Thr  Leu  Pro  Leu  Asp  Ala  Ser
                    405                      410                      415

Val  Asp  Leu  Gln  Leu  Asn  Ile  Ser  Phe  Thr  Tyr  Gly  Pro  Val  Ile  Leu
               420                      425                      430

Asn  Gly  Asp  Gly  Met  Asp  Tyr  Tyr  Glu  Ser  Pro  Leu  Leu  Asn  Ser  Gly
          435                      440                      445

Trp  Leu  Thr  Ile  Pro  Pro  Lys  Asp  Gly  Thr  Ile  Ser  Gly  Leu  Ile  Asn
     450                      455                      460

Lys  Ala  Gly  Arg  Gly  Asp  Gln  Phe  Thr  Val  Leu  Pro  His  Val  Leu  Thr
465                      470                      475                      480
```

```
Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600
```

( 2 ) INFORMATION FOR SEQ ID NO:96:

( i ) SEQUENCE CHARACTERISTICS:
      ( A ) LENGTH: 4604 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:96:

```
GTATCATTTT TATCTAATTT TGGAGATTTA GCAGTACTTA CTTCATTAGA AGAAGAATCT        60
GCCAGTTCCT GTCTATTACT GATATTTCGT TTCATTATTA TATGATTTAT ATTTTACTTT       120
TTCAATTATA TATACTCATT TGACTAGTTA ATCAATAAAA AGAATTCCTC GAGCTGCAGC       180
CCGATCCATA AAAATCAGTG TGATCTCACA TAGGATTTCG AAGTTCCAGT TAGATCAGGT       240
TTAAATGCCG GATCGACCTT AGTATGCTGC TTGAGTGTCT GTTGGTAGCG TCTTTTACAA       300
CAGTAAATCA GCAACAACAA AGCCAGGGCT GTACAACTTA ATATAGGAAC GCTGAGGAGA       360
CTGCCAAAAT TGAAGGAAGA GCGCCTAACC GTCTCAAGGA TCTGGTTAGA GGAGTCTATC       420
AGTACCTTAG CATCATCCAG TTTCTTAAGG GCGTTCCCTA AGTTTGTACC TACATCTAAC       480
CTATCAAGTG ATATAGCAGG GCCTAAGGCA ACTTTGCCTT CGTATACCAT ATCAGGGTAT       540
TGCCTGCCTC CAACTTGGAT AGTAGCACCA TCTATTTCAA CCAGTGGGCA GGTATCGGAG       600
GCAATGAATG TCAGCAACTT ATCAGGACTC TGATTAATAA TTGTGCTTGT GCTATAACAC       660
TTACATAGTA TAGAAGCACA ATTTGCGACG ATATTACCTT TTGACAGAAT AAATTTGTTG       720
CCCATAGTCC CAGATACCAA GGTCCGAGCA CAAGATGAAG TGTCGCCCCT AATACATTGT       780
TGTAAGAGTG GGCTCATGGG ATACAGGGAG TTCTGGCTAC AAATGGCTGA CTCTGAGACG       840
AATACACAAG ATGACTCATC AAAATTAGAT ATTAAGTAAC CATTAGTTGC AATATACCTC       900
GGGACAGTGG TGTACCACTC TTGTGATCCT ATGTTGTAAG AAACCGCTTC CAGTCTGTGG       960
ACTATAACCC CCTTGACTTC TGATAAAGTT GGGTATGAGA TACTTAGGAT GATGAATTTC      1020
CCGGGAAGAT CAACATGAGT TATTTTTGTT TTTATCCCCC GACTCTCCAA GATTGCAATC      1080
ATATCACTTC CAGAATATCC CAACTTCCCA AGTATCTTAT GAATTTCTCC TCCAAGAGCA      1140
TAAATCAGTG CCTGAATTGA TATCTCGGCT GAAATAGGGT CACGTAAACT CGGGCCAAAT      1200
ATTGACAACA ACTCAGTATA ATACCGAAGC AGTCTTAACC CTAATCTCTG CCCAACTAAT      1260
TCACATGACA TATGTTGCAT GGCAGGGACG AGTTCGTTGT TGACGTAGTC CTGGACTCCC      1320
```

```
TGAACGGCAA TGACGGTTTC TTGGGTAGCC TCCCTAATTT CTTCTATAGC TTTGTTAGAC  1380
TGTTCAAGGC TGGTTCTAAG AGATTGGATT GCTTGAGCAT TGAGGTTGGA TTGATGTAAA  1440
GCTATTCCTG CAGTGATTTG TGCAGCTGTA GCCACTCCTA AAGCTACACC TGCAAGTACC  1500
ACTCCTGCAA AACGCCTTTG TCTCCTACCT GACCCTAATG ACTGCAGGGG CTTCACATTC  1560
TTGGTCATTA GAGTCAAAGC TTGGTTGATT GGTTCGAGGA CTGAATTCAA TAATTTCTCA  1620
TACTCACCTA ATTCTGCTTT GGTACAATTC TCTATAAGTG AAACATTAGG CATCAGTTTT  1680
ATGACCAAGT ACTGGTGACT GGGCCTAGTC ATGATCTTGT AATGGACACT ATCAGTCCCG  1740
ATAATCCCAA TAGTTGACAA ATTATTCCAA TGTATCTGAG CCTTGGAACA AAGAAAGAGA  1800
CTGGCCATTC CGAGGCACCA CAGGACTAAC CAGGTGCAAT GAGAGCCTGA GTTGATTGCA  1860
TTGGGTTGCC GCCTTTCGAT CTGGGATCTC GCTCCTTTTG AGACACTCTC TGGTATGTGC  1920
TGGATGGTGG CCTCGTGGTT TCCGTGAACT GGGATGTTCT TCAATCTGTG GCTGGTTTGC  1980
TTGCGGGACC TGGTCCTGTT CATGGTGTAG GAGACGGGTC TGTCCGATGT TCGAGGATCG  2040
TAGTGCGTGG ATCGCTGAGC TGATGTTGTG CTGTGTCGTG CTCGGGAGGT CCTGGTCTCT  2100
TCGAGTTCGG TGCTGGGTTG TGGGGGGCGG TCTTGTTGGG TATGTGTTTG GGTTTGGAG   2160
CTTTTGGGGA TTCCCTTGTG CATTACGATA CAAACTTAAC GGATATCGCG ATAATGAAAT  2220
AATTTATGAT TATTTCTCGC TTTCAATTTA ACACAACCCT CAAGAACCTT TGTATTTATT  2280
TTCACTTTTT AAGTATAGAA TAAAGAAGCT CTAATTAATT AAGCTACAAA TAGTTTCGTT  2340
TTCACCTTGT CTAATAACTA ATTAATTAAC CCCGATAGCT GATTAGTTTT TGTTGGGTTA  2400
ATTAATTAGT CATCAGGCAG GGCGAGAACG AGACTATCTG CTCGTTAATT AATTAGAGCT  2460
TGATTCTTTA TTCTATACTT AAAAAGTGAA AATAAATACA AAGGTTCTTG AGGGTTGTGT  2520
TAAATTGAAA GCGAGAAATA ATCATAAATT ATTTCATTAT CGCGATATCC GTTAAGTTTG  2580
TATCGTAATG CTCCCCTACC AAGACAAGGT GGGTGCCTTC TACAAGGATA ATGCAAGAGC  2640
CAATTCAACC AAGCTGTCCT TAGTGACAGA AGGACATGGG GGCAGGAGAC CACCTTATTT  2700
GTTGTTTGTC CTTCTCATCT TATTGGTTGG TATCCTGGCC TTGCTTGCTA TCACTGGAGT  2760
TCGATTTCAC CAAGTATCAA CTAGTAATAT GGAATTTAGC AGATTGCTGA AAGAGGATAT  2820
GGAGAAATCA GAGGCCGTAC ATCACCAAGT CATAGATGTC TTGACACCGC TCTTCAAGAT  2880
TATTGGAGAT GAGATTGGGT TACGGTTGCC ACAAAAGCTA AACGAGATCA AACAATTTAT  2940
CCTTCAAAAG ACAAATTTCT TCAATCCGAA CAGAGAATTC GACTTCCGCG ATCTCCACTG  3000
GTGCATTAAC CCGCCTAGTA CGGTCAAGGT GAATTTTACT AATTACTGTG AGTCAATTGG  3060
GATCAGAAAA GCTATTGCAT CGGCAGCAAA TCCTATCCTT TTATCAGCCC TATCTGGGGG  3120
CAGAGGTGAC ATATTCCCAC CACACAGATG CAGTGGAGCT ACTACTTCAG TAGGCAAAGT  3180
TTTCCCCCTA TCAGTCTCAT TATCCATGTC TTTGATCTCA AGAACCTCAG AGGTAATCAA  3240
TATGCTGACC GCTATCTCAG ACGGCGTGTA TGGCAAAACT TACTTGCTAG TGCCTGATGA  3300
TATAGAAAGA GAGTTCGACA CTCGAGAGAT TCGAGTCTTT GAAATAGGGT TCATCAAGAG  3360
GTGGCTGAAT GACATGCCAT TACTCCAAAC AACCAACTAT ATGGTACTCC CGAAGAATTC  3420
CAAAGCCAAG GTATGTACTA TAGCAGTGGG TGAGTTGACA CTGGCTTCCT TGTGTGTAGA  3480
AGAGAGCACT GTATTATTAT ATCATGACAG CAGTGGTTCA CAAGATGGTA TTCTAGTAGT  3540
GACACTGGGG ATATTTTGGG CAACACCTAT GGATCACATT GAGGAAGTGA TACCTGTCGC  3600
TCACCCATCA ATGAAGAAAA TACATATAAC AAACCACCGT GGTTTTATAA AAGATTCAAT  3660
TGCAACCTGG ATGGTGCCTG CCCTGGCCTC TGAGAAACAA GAAGAACAAA AAGGTTGTCT  3720
```

-continued

```
GGAGTCAGCT TGTCAAAGAA AAACCTACCC CATGTGCAAC CAAGCGTCAT GGGAACCCTT    3780
CGGAGGAAGA CAGTTGCCAT CTTATGGGCG GTTGACATTA CCTCTAGATG CAAGTGTTGA    3840
CCTTCAACTT AACATATCGT TCACATACGG TCCGGTTATA CTGAATGGAG ATGGTATGGA    3900
TTATTATGAA AGCCCACTTT TGAACTCCGG ATGGCTTACC ATTCCCCCA  AAGACGGAAC    3960
AATCTCTGGA TTGATAAACA AAGCAGGTAG AGGAGACCAG TTCACTGTAC TCCCCCATGT    4020
GTTAACATTT GCGCCCAGGG AATCAAGTGG AAATTGTTAT TTACCTATTC AAACATCTCA    4080
AATTAGAGAT AGAGATGTCC TCATTGAGTC CAATATAGTG GTGTTGCCTA CACAGAGTAT    4140
TAGATATGTC ATAGCAACGT ATGACATATC ACGAAGTGAT CATGCTATTG TTTATTATGT    4200
TTATGACCCA ATCCGGACGA TTTCTTATAC GCACCCATTT AGACTAACTA CCAAGGGTAG    4260
ACCTGATTTC CTAAGGATTG AATGTTTTGT GTGGGATGAC AATTTGTGGT GTCACCAATT    4320
TTACAGATTC GAGGCTGACA TCGCCAACTC TACAACCAGT GTTGAGAATT TAGTCCGTAT    4380
AAGATTCTCA TGTAACCGTT AATTTTATC  CCGGGTTTTT ATAGCTAATT AGTCATTTTT    4440
TCGTAAGTAA GTATTTTTAT TTAATACTTT TTATTGTACT TATGTTAAAT ATAACTGATG    4500
ATAACAAAAT CCATTATGTA TTATTTATAA CTGTAATTTC TTTAGCGTAG TTAGATGTCC    4560
AATCTCTCTC AAATACATCG GCTATCTTTT TAGTGAGATT TTGA                     4604
```

( 2 ) INFORMATION FOR SEQ ID NO:97:

( i ) SEQUENCE CHARACTERISTICS:
( A ) LENGTH: 650 amino acids
( B ) TYPE: amino acid
( C ) STRANDEDNESS: single
( D ) TOPOLOGY: linear ( i i ) MOLECULE TYPE: peptide ( v ) FRAGMENT TYPE: internal ( x i ) SEQUENCE DESCRIPTION: SEQ ID NO:97:

| His | Ser | Arg | Val | Tyr | Ser | Lys | Ser | Thr | Gly | Thr | Leu | Asp | Pro | Lys | Phe |
|---|---|---|---|---|---|---|---|---|---|---|---|---|---|---|---|
| 1 | | | | 5 | | | | | 10 | | | | | 15 | |
| Ala | Pro | Asp | Val | Lys | Thr | His | Gln | Lys | Leu | Thr | Gln | Gln | Tyr | Arg | Arg |
| | | | 20 | | | | 25 | | | | | 30 | | | |
| Lys | Cys | Cys | Tyr | Ile | Leu | Leu | Leu | Ala | Leu | Ala | Thr | Cys | Ser | Leu |
| | | 35 | | | | 40 | | | | 45 | | | | |
| Ile | Pro | Val | Ser | Leu | Leu | Ser | Gly | Phe | Asn | Phe | Ser | Ser | Arg | Arg | Val |
| | 50 | | | | | 55 | | | | 60 | | | | | |
| Thr | Glu | Leu | Ile | Gln | Asn | Ser | Ser | Asp | Ile | Leu | Val | Lys | Ala | Asp | Asp |
| 65 | | | | | 70 | | | | 75 | | | | | 80 | |
| Leu | Lys | Lys | Leu | Ala | Asn | Gly | Leu | Asn | Thr | Gly | Val | Asp | Leu | Arg | Asp |
| | | | | 85 | | | | | 90 | | | | 95 | | |
| Leu | Ser | Ile | Ala | Pro | Gly | Leu | Ala | Val | Lys | Gly | Glu | Tyr | Val | Met | Asp |
| | | | 100 | | | | | 105 | | | | 110 | | | |
| Pro | Tyr | Gln | Arg | Gly | Gly | Val | Gln | Ile | Thr | Ala | Gly | Asp | Ile | Glu | Val |
| | | | 115 | | | | 120 | | | | 125 | | | | |
| Leu | Pro | Cys | Thr | Asp | Ser | Ala | Ile | Phe | Thr | Leu | Leu | Lys | Asp | Pro | Ser |
| | 130 | | | | 135 | | | | 140 | | | | | | |
| Gln | Asn | Ile | Ile | Thr | Ser | Thr | Ser | Tyr | Cys | Lys | Cys | Leu | Ile | Ser | Ala |
| 145 | | | | 150 | | | | | 155 | | | | | 160 | |
| Cys | Asn | Ala | Val | Ile | Asn | Gly | Lys | Ser | Leu | Ile | Phe | Lys | Asn | Gly | Met |
| | | | 165 | | | | | 170 | | | | | 175 | | |
| Thr | Gly | Ser | Val | Leu | Thr | Arg | Ala | Cys | Ser | Ser | Thr | Asp | Gly | Arg | Ile |

|     |     |     |     |     |     |     | 180 |     |     |     |     | 185 |     |     |     |     | 190 |     |     |
|-----|-----|-----|-----|-----|-----|-----|-----|-----|-----|-----|-----|-----|-----|-----|-----|-----|-----|-----|-----|

Cys Gln Gln Leu Leu Pro Ser Met Pro Tyr Leu Ser Asn Gln Ser Cys
      195                    200                    205

Ile Ala Ser Glu Ser Val Phe Val Cys Ser Ser Glu Asp Phe Asn Ser
210                          215                         220

Ile Leu Tyr Gly Asn Thr Ala Ile Tyr Arg Pro Val Thr Thr Tyr Trp
225                 230                 235                  240

Glu Gln Ser Gly Ile Asn Tyr Ser Val Ala Glu Leu Pro Tyr Ser Ile
                245                 250                 255

Ser Leu Ile Ile Phe Lys Gly Pro Leu Asp Val His Thr Ile Lys Thr
            260                 265                 270

Lys Ile Gly Arg Ser Glu Leu Ile Ala Ile Met Asp Ser Gly Ser Tyr
        275                 280                 285

Gly Leu Lys Gly Leu Ile Lys His Ile Glu Gly Gly Leu Ala Tyr Ile
        290                 295                 300

Leu Ala Gln Ile Ser Ile Glu Ala Ser Ile Pro Asp Arg Leu Ser Pro
305                 310                 315                  320

Gly Phe Ile Ser Leu Glu Thr Tyr Tyr Arg Leu Leu Arg Leu Gly
                325                 330                 335

Leu Arg Gln Gly Val Leu Glu Cys Ser Met His Gln Met Ala Pro Val
            340                 345                 350

Leu Glu Asn Asn Val Tyr Asp Gln Val Gly Gln Val Ala Ile Val Thr
            355                 360                 365

Glu Gln Thr Ala Glu Arg Ile Glu Ile Ala Lys Asn Ser Gln Glu
        370                 375                 380

Leu Ser Thr Arg Leu Ser Gln Ile Ala Gln Ala Asn Leu Asn Ser Gln
385                 390                 395                  400

His Leu Ala Ile Gly Ala Thr Ile Gln Ala Ala Thr Ala Val Gly Leu
                405                 410                 415

Ala Val Gly Ala Leu Val Val Gly Ala Phe Arg Arg Gln Arg Arg Gly
            420                 425                 430

Ser Gly Leu Ser Gln Leu Pro Lys Val Asn Lys Thr Met Leu Thr Leu
        435                 440                 445

Ala Gln Asn Ile Pro Glu Leu Val Ser Asn Leu Leu Lys Glu Tyr Glu
    450                 455                 460

Gly Leu Glu Ala Lys Thr Cys Asn Glu Ile Leu Ser Val Asn Pro Met
465                 470                 475                  480

Leu Lys Ile Val Leu Tyr Gln His Ser Pro Arg Thr Met Ile Lys Tyr
                485                 490                 495

His Val Ser Asp Thr Gly Ile Ile Gly Ile Thr Ser Leu Asn Asn Trp
            500                 505                 510

His Ile Gln Ala Lys Ser Cys Leu Phe Leu Ser Ala Met Gly Leu Cys
        515                 520                 525

Trp Leu Val Leu Trp Thr Cys His Ser Gly Ser Asn Ile Ala Asn Pro
    530                 535                 540

Gln Arg Arg Glu Ile Gln Ser Arg Ala Gly Lys Ser Val Ser Glu Pro
545                 550                 555                  560

Ile His Gln Ile Thr Ala Glu His Asn Gly His Val Pro Ile Asn Lys
                565                 570                 575

Leu Arg His Ser Thr Gln Lys Arg Ser Arg Thr Arg Asn Met Thr Tyr
            580                 585                 590

Ser Val Pro Arg Asp Ser Thr Arg Pro Asp Tyr His Thr Ser Arg Gln
        595                 600                 605

```
Ala  Ser  Thr  Thr  Ser  His  Arg  Ala  Arg  Ser  Thr  Arg  Thr  Glu  Glu  Leu
     610                 615                 620

Glu  Thr  Ser  Pro  Gln  Pro  Arg  Asp  Gln  Gln  Thr  His  Thr  Gln  Thr
625                 630                 635                          640

Lys  Ser  Ser  Lys  Pro  Ile  Gly  Lys  His  Met
                    645                      650
```

( 2 ) INFORMATION FOR SEQ ID NO:98:

( i ) SEQUENCE CHARACTERISTICS:
    ( A ) LENGTH: 604 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:98:

```
Met  Leu  Pro  Tyr  Gln  Asp  Lys  Val  Gly  Ala  Phe  Tyr  Lys  Asp  Asn  Ala
1                   5                        10                      15

Arg  Ala  Asn  Ser  Thr  Lys  Leu  Ser  Leu  Val  Thr  Glu  Gly  His  Gly  Gly
               20                  25                       30

Arg  Arg  Pro  Pro  Tyr  Leu  Leu  Phe  Val  Leu  Leu  Ile  Leu  Leu  Val  Gly
          35                      40                      45

Ile  Leu  Ala  Leu  Leu  Ala  Ile  Thr  Gly  Val  Arg  Phe  His  Gln  Val  Ser
     50                  55                       60

Thr  Ser  Asn  Met  Glu  Phe  Ser  Arg  Leu  Leu  Lys  Glu  Asp  Met  Glu  Lys
65                       70                  75                           80

Ser  Glu  Ala  Val  His  His  Gln  Val  Ile  Asp  Val  Leu  Thr  Pro  Leu  Phe
                    85                  90                       95

Lys  Ile  Ile  Gly  Asp  Glu  Ile  Gly  Leu  Arg  Leu  Pro  Gln  Lys  Leu  Asn
               100                 105                      110

Glu  Ile  Lys  Gln  Phe  Ile  Leu  Gln  Lys  Thr  Asn  Phe  Phe  Asn  Pro  Asn
          115                      120                      125

Arg  Glu  Phe  Asp  Phe  Arg  Asp  Leu  His  Trp  Cys  Ile  Asn  Pro  Pro  Ser
     130                      135                 140

Thr  Val  Lys  Val  Asn  Phe  Thr  Asn  Tyr  Cys  Glu  Ser  Ile  Gly  Ile  Arg
145                      150                 155                           160

Lys  Ala  Ile  Ala  Ser  Ala  Ala  Asn  Pro  Ile  Leu  Leu  Ser  Ala  Leu  Ser
                    165                 170                      175

Gly  Gly  Arg  Gly  Asp  Ile  Phe  Pro  Pro  His  Arg  Cys  Ser  Gly  Ala  Thr
               180                      185                 190

Thr  Ser  Val  Gly  Lys  Val  Phe  Pro  Leu  Ser  Val  Ser  Leu  Ser  Met  Ser
          195                      200                 205

Leu  Ile  Ser  Arg  Thr  Ser  Glu  Val  Ile  Asn  Met  Leu  Thr  Ala  Ile  Ser
     210                 215                      220

Asp  Gly  Val  Tyr  Gly  Lys  Thr  Tyr  Leu  Leu  Val  Pro  Asp  Asp  Ile  Glu
225                      230                 235                           240

Arg  Glu  Phe  Asp  Thr  Arg  Glu  Ile  Arg  Val  Phe  Glu  Ile  Gly  Phe  Ile
               245                      250                      255

Lys  Arg  Trp  Leu  Asn  Asp  Met  Pro  Leu  Leu  Gln  Thr  Thr  Asn  Tyr  Met
               260                      265                      270

Val  Leu  Pro  Lys  Asn  Ser  Lys  Ala  Lys  Val  Cys  Thr  Ile  Ala  Val  Gly
          275                      280                      285

Glu  Leu  Thr  Leu  Ala  Ser  Leu  Cys  Val  Glu  Glu  Ser  Thr  Val  Leu  Leu
     290                      295                      300
```

```
Tyr His Asp Ser Ser Gly Ser Gln Asp Gly Ile Leu Val Val Thr Leu
305                     310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Gln Lys Gly Cys Leu Glu Ser Ala Cys Gln Arg
    370                 375                 380

Lys Thr Tyr Pro Met Cys Asn Gln Ala Ser Trp Glu Pro Phe Gly Gly
385             390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
450                 455                 460

Lys Ala Gly Arg Gly Asp Gln Phe Thr Val Leu Pro His Val Leu Thr
465             470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545             550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600
```

(2) INFORMATION FOR SEQ ID NO:99:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:99:

CAGTTGGTAC CACTGGTATT TTATTTCAG                    29

(2) INFORMATION FOR SEQ ID NO:100:

(i) SEQUENCE CHARACTERISTICS:
    (A) LENGTH: 61 base pairs
    (B) TYPE: nucleic acid
    (C) STRANDEDNESS: single ( D ) TOPOLOGY: linear ( i i ) MOLECULE TYPE: cDNA ( x i ) SEQUENCE DESCRIPTION: SEQ ID NO:100:

TATCTGAATT CCTGCAGCCC GGGTTTTTAT AGCTAATTAG TCAAATGTGA GTTAATATTA    60

G    61

( 2 ) INFORMATION FOR SEQ ID NO:101:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:101:

TCGCTGAATT CGATATCAAG CTTATCGATT TTTATGACTA GTTAATCAAA TAAAAAGCAT    60

ACAAGC    66

( 2 ) INFORMATION FOR SEQ ID NO:102:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:102:

TTATCGAGCT CTGTAACATC AGTATCTAAC    30

( 2 ) INFORMATION FOR SEQ ID NO:103:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:103:

TCCGGTACCG CGGCCGCAGA TATTTGTTAG CTTCTGC    37

( 2 ) INFORMATION FOR SEQ ID NO:104:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:104:

TCGCTCGAGT AGGATACCTA CCTACTACCT ACG    33

( 2 ) INFORMATION FOR SEQ ID NO:105:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i i  ) MOLECULE TYPE: cDNA ( x i ) SEQUENCE DESCRIPTION: SEQ ID NO:105:

TCGCTCGAGC TTTCTTGACA ATAACATAG　　　　　　　　　　　　　　　　　　　29

( 2 ) INFORMATION FOR SEQ ID NO:106:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:106:

TAGGAGCTCT TTATACTACT GGGTTACAAC　　　　　　　　　　　　　　　　　　　30

( 2 ) INFORMATION FOR SEQ ID NO:107:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:107:

AATTCCTCGA GGGATCC　　　　　　　　　　　　　　　　　　　　　　　　　　17

( 2 ) INFORMATION FOR SEQ ID NO:108:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:108:

CGGGATCCCT CGAGG　　　　　　　　　　　　　　　　　　　　　　　　　　　15

( 2 ) INFORMATION FOR SEQ ID NO:109:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:109:

TCGGGATCCG GGTTAATTAA TTAGTTATTA GACAAGGTG　　　　　　　　　　　　　　39

( 2 ) INFORMATION FOR SEQ ID NO:110:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:110:

TAGGAATTCC TCGAGTACGA TACAAACTTA AGCGGATATC G    41

( 2 ) INFORMATION FOR SEQ ID NO:111:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:111:

GGCCGCGTCG ACATGCA    17

( 2 ) INFORMATION FOR SEQ ID NO:112:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:112:

TGTCGACGC    9

( 2 ) INFORMATION FOR SEQ ID NO:113:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:113:

ATCATCGAAT TCTGAATGTT AAATGTTATA CTTTG    35

( 2 ) INFORMATION FOR SEQ ID NO:114:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:114:

GGGGGTACCT TTGAGAGTAC CACTTCAG    28

( 2 ) INFORMATION FOR SEQ ID NO:115:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:115:

GGGTCTAGAG CGGCCGCTTA TAAAGATCTA AAATGCATAA TTTC    44

( 2 ) INFORMATION FOR SEQ ID NO:116:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:116:

```
ATCATCCTGC AGGTATTCTA AACTAGGAAT AGATG                                   35
```

( 2 ) INFORMATION FOR SEQ ID NO:117:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:117:

```
GTACGTGACT AATTAGCTAT AAAAGGATC CGGTACCCTC GAGTCTAGAA TCGATCCGG           60
GTTTTTATGA CTAGTTAATC AC                                                 82
```

( 2 ) INFORMATION FOR SEQ ID NO:118:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:118:

```
GGCCGTGATT AACTAGTCAT AAAAACCCGG GATCGATTCT AGACTCGAGG GTACCGGATC         60
CTTTTTATAG CTAATTAGTC AC                                                 82
```

( 2 ) INFORMATION FOR SEQ ID NO:119:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:119:

```
ATCATCGAGC TCGCGGCCGC CTATCAAAAG TCTTAATGAG TT                           42
```

( 2 ) INFORMATION FOR SEQ ID NO:120:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:120:

```
GAATTCCTCG AGCTGCAGCC CGGGTTTTTA TAGCTAATTA GTCATTTTTT CGTAAGTAAG         60
TATTTTTATT TAA                                                           73
```

( 2 ) INFORMATION FOR SEQ ID NO:121:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:121:

CCCGGGCTGC AGCTCGAGGA ATTCTTTTA TTGATTAACT AGTCAAATGA GTATATATAA      60

TTGAAAAAGT AA      72

(2) INFORMATION FOR SEQ ID NO:122:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:122:

GATGATGGTA CCTTCATAAA TACAAGTTTG ATTAAACTTA AGTTG      45

POXVIRUS-CANINE DISTEMPER VIRUS (CDV) RECOMBINANTS AND COMPOSITIONS AND METHODS EMPLOYING THE RECOMBINANTS

RELATED APPLICATIONS

This application is a continuation-in-part of application Ser. No. 08/073,962, U.S. Pat. No. 5,503,834, filed Jun. 8, 1993 as a continuation of application Ser. No. 07/776,867, filed Oct. 22, 1991, abandoned which in turn is a continuation-in-part of application Ser. No. 07/621,614, filed Nov. 30, 1990, abandoned. This application is also a continuation-in-part of application Ser. No. 07/938,283, filed Aug. 31, 1992, abandoned which in turn is a continuation-in-part application of Ser. No. 07/621,614, filed Nov. 30, 1990, abandoned. This application is also a continuation-in-part of application Ser. No. 08/105,483, U.S. Pat. No. 5,454,807, filed Aug. 12, 1993, which in turn is a continuation of application Ser. No. 07/847,951 filed Mar. 6, 1992, abandoned, which in turn is a continuation-in-part of application Ser. No. 07/713,967, filed Jun. 11, 1991, abandoned, which in turn is a continuation-in-part of application Ser. No. 07/666,056, filed Mar. 7, 1991, abandoned. Each of the aforementioned applications is hereby incorporated herein by reference.

FIELD OF THE INVENTION

The present invention relates to poxvirus-canine distemper virus (CDV) recombinants, especially NYVAC-CDV and ALVAC-CDV recombinants, expression products from such recombinants, compositions, such as an antigenic, immunological or vaccine composition, containing a poxvirus-CDV recombinant or an expression product from such a recombinant; to methods of making and using the poxvirus-CDV recombinant; and, to methods of making and using the composition.

Various publications are cited throughout the following text, with the full citation of these publications appearing in the section headed References. Each of the publications cited in the following text is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990, 1993a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993 a,b; Taylor et al., 1992; 1991b; 1988b).

Canine distemper (CD) is a highly infectious, febrile disease of dogs and other carnivores (reviewed by Fenner, et al., 1987). The mortality rate is high; ranging between 30 and 80 percent. Dogs surviving often have permanent central nervous system damage (Fenner, et al. 1987). Similarly, measles virus (MV) causes an acute infectious febrile disease characterized by a generalized macropapular eruption. The disease mainly affects children. The established etiology of CD is infection by a member of the Paramyxovirus family; morbillivirus genus known as CD virus (CDV). In general, Paramyxoviruses are enveloped viruses containing a 18–20 kb single-stranded RNA genome of negative polarity. The genome encodes 5 to 7 structural proteins including a fusion (F) and either a hemagglutinin-neuraminidase (HN) or hemagglutinin (HA) glycoprotein. The membrane glycoprotein hemagglutinin (HA), is responsible for hemagglutination and attachment of the virus to the host cell, and the fusion glycoprotein (F), causes membrane fusion between the virus and the infected cell or between the infected and adjacent uninfected cells (Graves et al., 1978). The order of genes in the MV genome has been deduced by Richardson et al. (1985) and Dowling et al. (1986). The nucleotide sequence of the MVHA gene and MVF gene has been determined by Alkhatib and Briedis (1986) and Richardson et al. (1986), respectively. In the case of CDV, both an F and HA glycoprotein are found present in the viral envelope and on the surface of infected cells.

By inference from analyses with other morbillivirus members, in particular measles virus, the CDV F and HA glycoproteins appear important for CDV infectivity and its immunobiology (reviewed by Diallo, 1990). From studies with measles virus, it has been established that the HA and F proteins induce neutralizing antibodies (Norrby et al., 1975). Further, poxvirus-based recombinants expressing the measles HA or F alone or in combination have been shown to elicit protective immune responses in mice against MV encephalitis (Drillien et al., 1988; Wild et al., 1990) and in dogs against a lethal CDV challenge (Taylor et al., 1991d; Taylor et al., 1992). Specific to CDV, purified F protein has been shown to provide protection in dogs against CDV challenge (Norrby et al., 1986).

CDV and MV are structurally similar and share a close serological relationship. Immunoprecipitation studies have shown that antiserum to MV will precipitate all CDV proteins (P, NP, F, HA and M). By contrast, antiserum to CDV will precipitate all MV proteins except the HA glycoprotein (Hall et al., 1980; Orvell et al., 1980; Stephenson et al., 1979). In light of this close serological relationship, it has previously been demonstrated that vaccination with MV will elicit protection against CDV challenge in dogs (Gillespie et al., 1960; Moura et al., 1961; Warren et al., 1960). Neutralizing antibodies against CDV have been reported in human anti-MV sera (Adams et al., 1957; Imagawa et al., 1960; Karzon, 1955; Karzon, 1962) but neutralizing antibodies against MV have not been found in anti-CDV sera from dogs (Delay et al., 1965; Karzon, 1962; Roberts, 1965).

Thus, the protection of dogs with MV antigens or with MV antigens expressed by a recombinant poxvirus fails to teach or suggest protection from CDV antigens or from a recombinant poxvirus expressing CDV antigens. Indeed, heretofore coding sequences for CDV antigens and a recombinant poxvirus containing coding sequences for CDV antigens were not known or suggested.

Presently, vaccination with live, attenuated vaccine strains provides an effective means for controlling canine distemper. However, vaccine-associated complications stemming from the replication competency of these vaccine strains in the vaccinated animal have been documented (Tizard, 1990). It can therefore be appreciated that NYVAC and ALVAC based CDV recombinants, not heretofore taught or suggested, provide a means for eliminating the deliberate introduction of live, modified CDV into the environment while providing safe and efficacious means for expressing CDV gene products from the expression thereof and antigenic, immunological or vaccine compositions.

OBJECTS AND SUMMARY OF INVENTION

It is therefore an object of this invention to provide modified recombinant viruses, which viruses have enhanced safety, and to provide a method of making such recombinant viruses.

It is an additional object of this invention to provide a recombinant poxvirus antigenic, immunological or vaccine composition having an increased level of safety compared to known recombinant poxvirus vaccines, or antigenic or immunological compositions.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

In one aspect, the present invention relates to a modified recombinant virus having inactivated virus-encoded genetic functions so that the recombinant virus has attenuated virulence and enhanced safety. The functions can be nonessential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes an antigenic protein, e.g., derived from a pathogen, such as Morbillivirus, preferably CDV.

In another aspect, the present invention relates to a vaccine for inducing an antigenic response in a host animal inoculated with an antigenic or immunological composition vaccine, said composition including a carrier and a modified recombinant virus having inactivated nonessential virus-encoded genetic functions so that the recombinant virus has attenuated virulence and enhanced safety. The virus used in the vaccine antigenic or immunological composition according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from a pathogen, such as Morbillivirus, preferably CDV.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein (e.g., derived from a pathogen, such as Morbillivirus, preferably CDV) wherein the composition, when administered to a host, is capable of inducing an immunological response specific to the protein encoded by the pathogen.

In a further aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., from a pathogen, such as Morbillivirus, preferably CDV.

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome.

The DNA codes for an antigen, of Morbillivirus, preferably CDV, and, more preferably, codes for the F and/HA antigens of CDV. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992).

The antigenic, immunological or vaccine composition preferably elicits Morbillivirus neutralizing antibodies, hemagglutination-inhibiting antibodies and protective immunity against Morbillivirus, especially CDV, and especially in dogs.

Other objects and embodiment of the invention are disclosed in or obvious from the following detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 8 shows the DNA sequence (SEQ ID NO:39) of a canarypox PvuII fragment containing the C5 ORF.

FIG. 11 shows the nucleotide sequence (SEQ ID NO:48) of a fragment of TROVAC DNA containing an F8 ORF;

FIG. 12 shows the DNA sequence (SEQ ID NO:51) of a 2356 base pair fragment of TROVAC DNA containing the F7 ORF;

FIGS. 14A–D show the nucleotide sequence of H6 promoted CDV HA and CDV HA translation (SEQ ID NOS:83, 84);

FIGS. 15A–D show the nucleotide sequence of H6 promoted CDV F and CDV F translation (SEQ ID NOS:87, 88);

FIGS. 16A–G show the nucleotide sequence derived from plasmid pMM126 of the H6 promoted canine distemper virus (CDV) F, H6 promoted CDV HA, NYVAC sequences flanking I4L, and translations of CDV open reading frames (SEQ ID NOS:93, 94, 95), and;

FIGS. 17A–G show the predicted nucleotide sequence of the H6 promoted canine distemper virus (CDV) F, H6 promoted CDV HA, ALVAC sequences flanking C6, and translations of CDV open reading frames (SEQ ID NOS: 96, 97, 98).

DETAILED DESCRIPTION OF THE INVENTION

Figure 1:
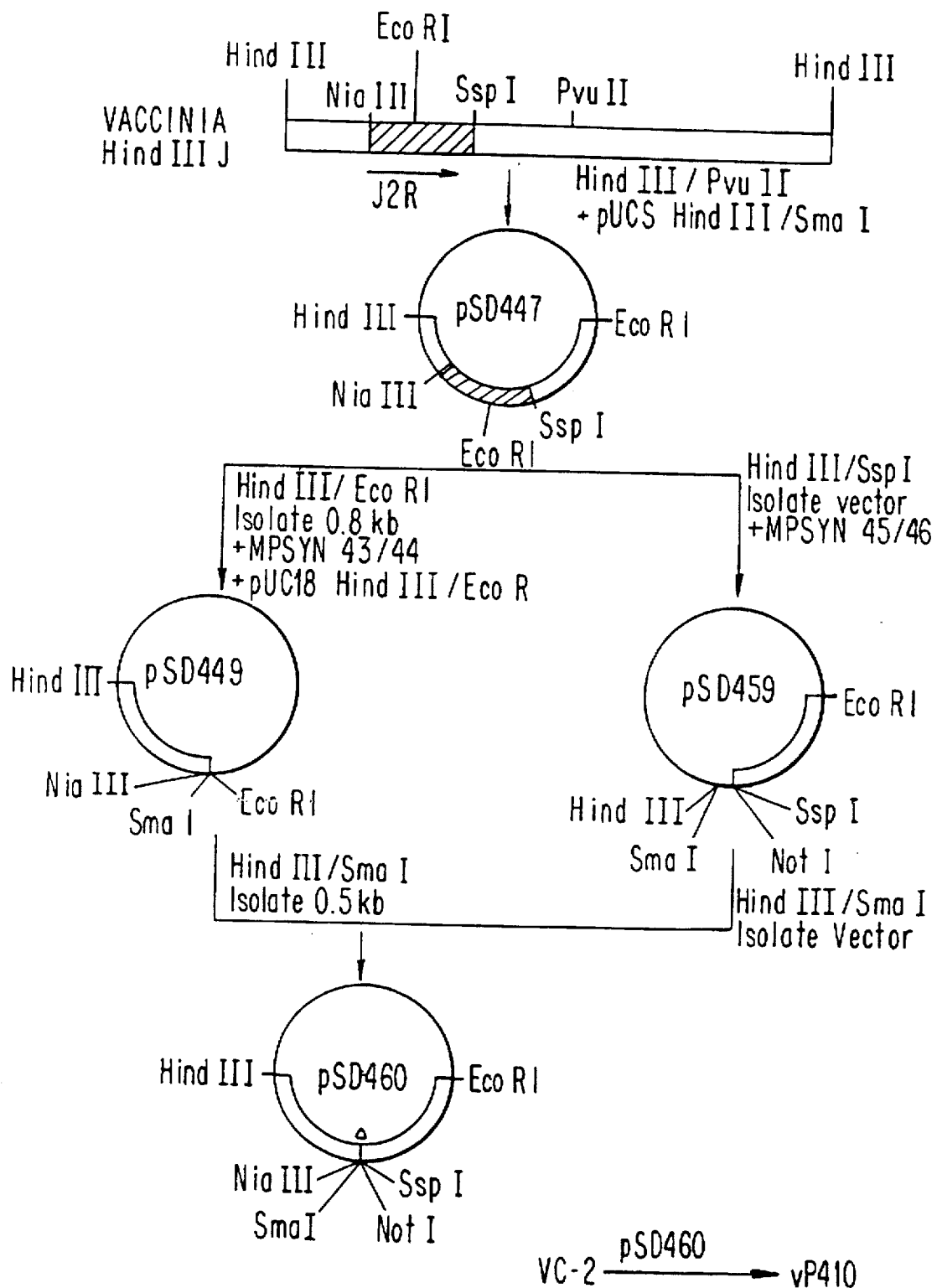
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L–K1L) vP804; and (6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991c). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

Accordingly, NYVAC, ALVAC and TROVAC are preferred vectors for insertion of coding for Morbillivirus antigens, especially CDV antigens and, preferably coding for CDV F and/or HA. In the vaccine, antigenic or immunological compositions, the recombinant poxvirus according to the invention is preferably in admixture with a suitable carrier, diluent or excipient such as sterile water, physiological saline, glucose or the like.

More generally, the inventive antigenic, immunological or vaccine compositions (compositions containing the poxvirus recombinants of the invention) can be prepared in accordance with standard techniques well known to those skilled in the pharmaceutical or veterinary art. Such compositions can be administered to an animal or human patient in need of such administration in dosages and by techniques well known to those skilled in the medical or veterinary arts taking into consideration such factors as the age, sex, weight, and condition of the particular human or animal patient, and the route of administration.

Examples of compositions of the invention include liquid preparations for orifice, e.g., oral, nasal, anal, vaginal, etc., administration such as suspensions, syrups or elixirs; and, preparations for parental, subcutaneous, intradermal, intramuscular or intravenous administration (e.g., injectable administration) such as sterile suspensions or emulsions.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC. ALVAC was deposited on Nov. 14, 1996, under the terms of the Budapest Treaty with the ATCC, accession number VR-2547.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

CONSTRUCTION OF PLASMID pSD460 FOR DELETION OF THYMIDINE KINASE GENE (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

```
                          SmaI
MPSYN43  5'    TAATTAACTAGCTACCCGGG          3'
MPSYN44  3'    GTACATTAATTGATCGATGGGCCCTAA   5'
              NlaIII                  EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
         HindIII  SmaI
MPSYN45  5'  AGCTTCCCGGGTAAGTAATACGTCAAGGAGAAAACGAA
MPSYN46  3'      AGGGCCCATTCATTATGCAGTTCCTCTTTTGCTT
                               NotI         SspI
             ACGATCTGTAGTTAGCGGCCGCCTAATTAACTAAT  3' MPSYN45
             TGCTAGACATCAATCGCCGGCGGATTAATTGATTA  5' MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

Example 2

CONSTRUCTION OF PLASMID pSD486 FOR DELETION OF HEMORRHAGIC REGION (B13R+B14R)

Figure 2:
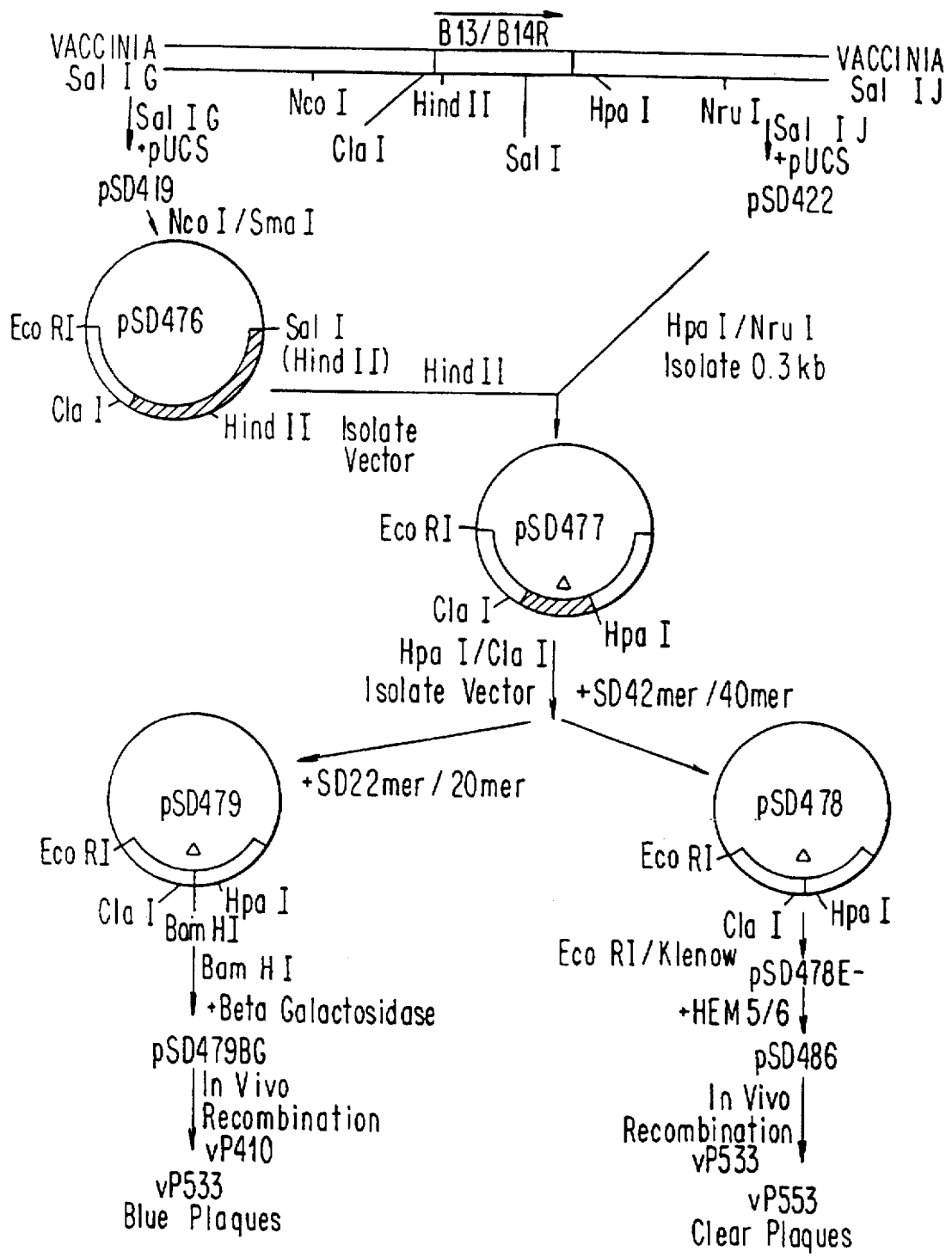
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right. SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

|  |  | ClaI | BamHI HpaI |  |
|---|---|---|---|---|
| SD22mer | 5' | CGATTACTATGAAGGATCCGTT | | 3' |
| SD20mer | 3' | TAATGATACTTCCTAGGCAA | | 5' | generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO:11)

|  |  | BamHI EcoRI HpaI |  |
|---|---|---|---|
| HEM5 | 5' | GATCCGAATTCTAGCT | 3' |
| HEM6 | 3' | GCTTAAGATCGA | 5' | generating plasmid pSD486. pSD486 was used as donor plasmid for recombination with recombinant vaccinia virus vP533, generating vP553, which was isolated as a clear plaque in the presence of X-gal.

Example 3

CONSTRUCTION OF PLASMID pMP494Δ FOR DELETION OF ATI REGION (A26L)

Figure 3:
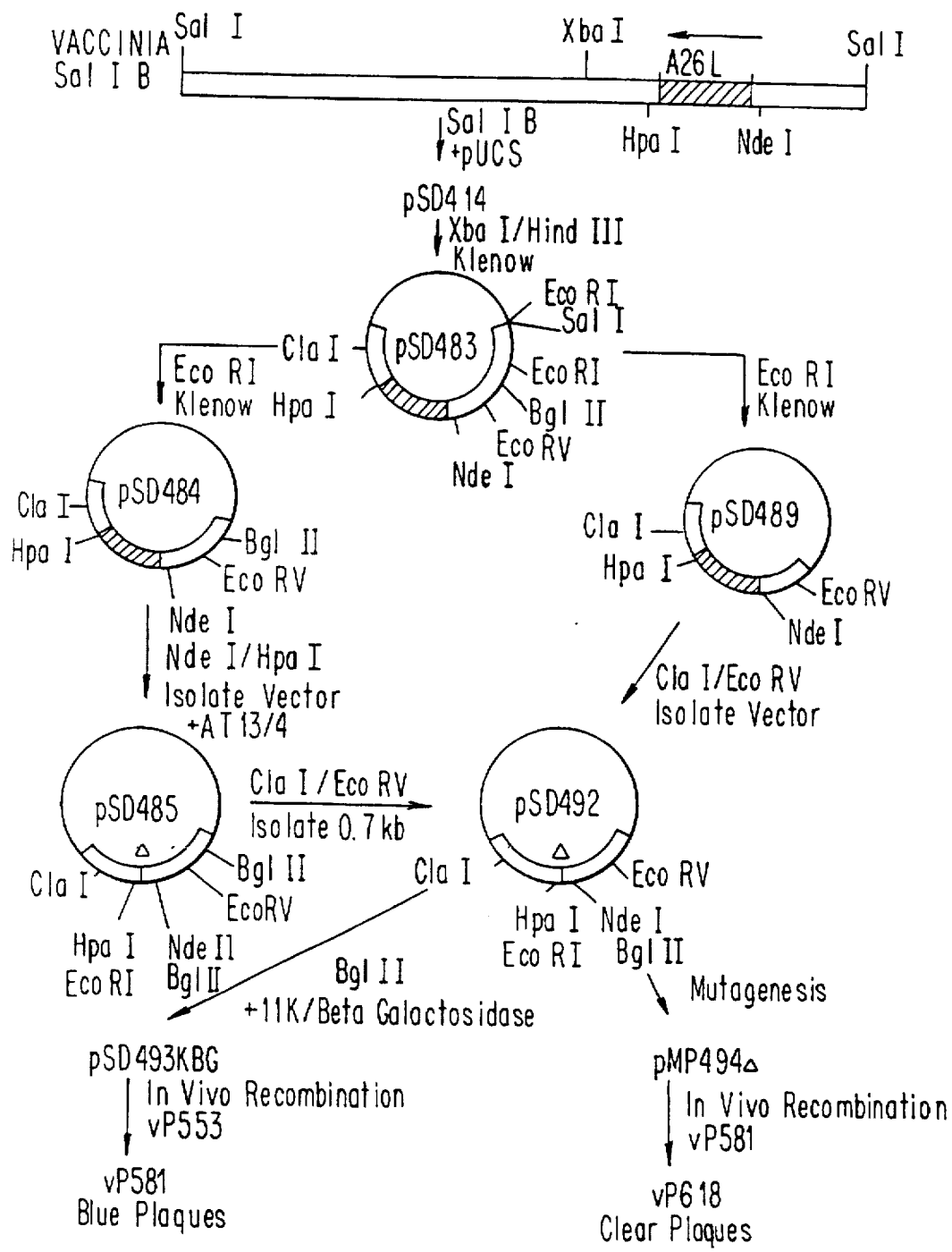
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

|  |  | ClaI | SacI | XhoI | HpaI |  |
|---|---|---|---|---|---|---|
| SD42mer | 5' | CGATTACTAGATCTGAGCTCCCCGGGCTCGAGGGATCCGTT | | | | 3' |
| SD40mer | 3' | TAATGATCTAGACTCGAGGGGCCCGAGCTCCCTAGGCAA | | | | 5' |
|  |  | BglII | SmaI | | BamHI | |

|  |  | NdeI |
|---|---|---|
| ATI3 | 5' | TATGAGTAACTTAACTCTTTTGTTAATTAAAAGTATATTCAAAAAATAAGT |
| ATI4 | 3' | ACTCATTGAATTGAGAAAACAATTAATTTTCATATAAGTTTTTTATTCA |
|  |  | BglII EcoRI HpaI |
|  |  | TATATAAATAGATCTGAATTCGTT 3' ATI3 |
|  |  | ATATATTTATCTAGACTTAAGCAA 5' ATI4 | reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 4

CONSTRUCTION OF PLASMID pSD467 FOR DELETION OF HEMAGGLUTININ GENE (A56R)

Figure 4:
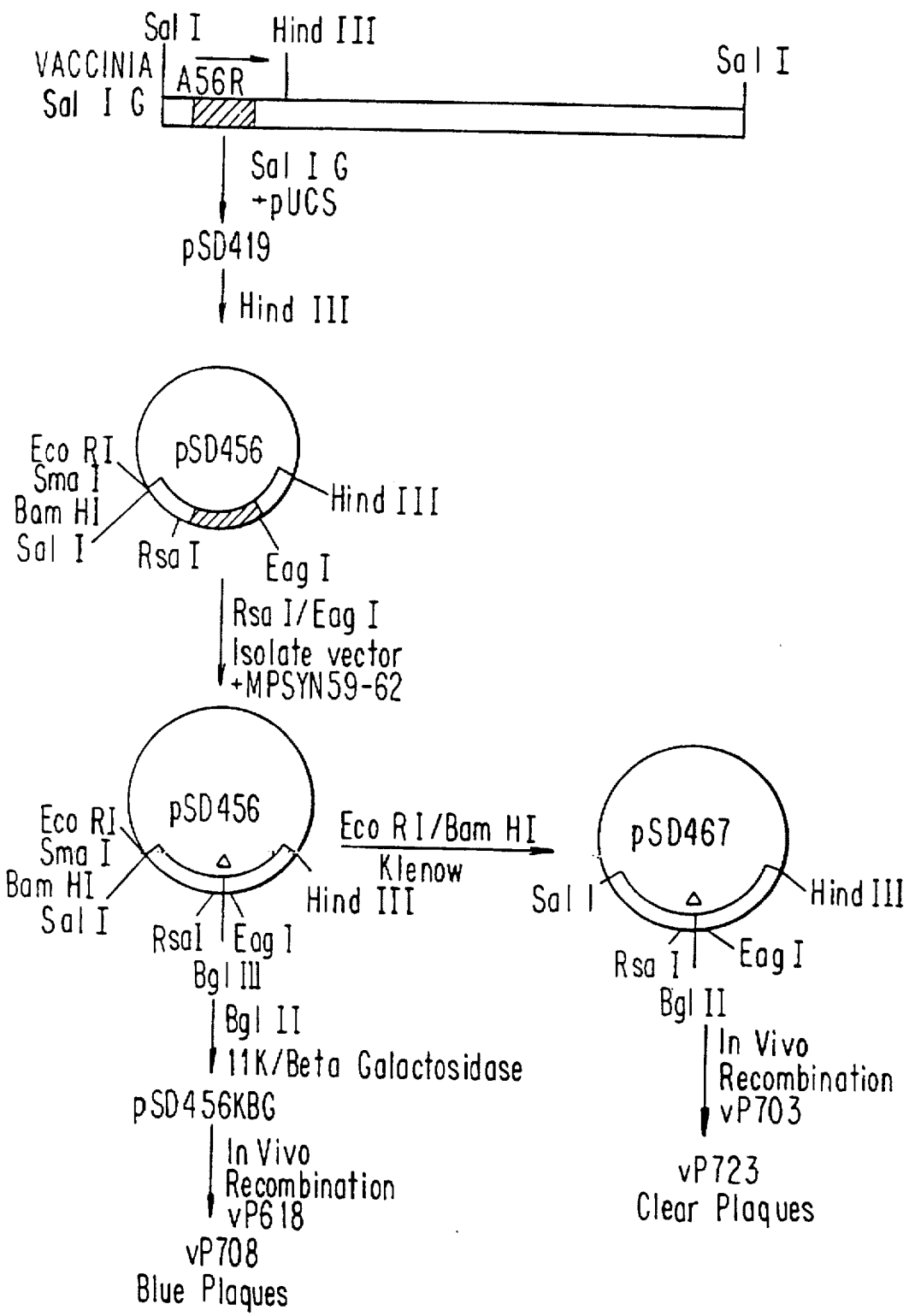
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

```
           RsaI
MPSYN59  5' ACACGAATGATTTTCTAAAGTATTTGGAAAGTTTTATAGGT-
MPSYN62  3' TGTGCTTACTAAAAGATTTCATAAACCTTTCAAAATATCCA-
MPSYN59     AGTTGATAGAACAAAATACATAATTT 3'
MPSYN62     TCAACTATCT 5'
MPSYN60  5'                            TGTAAAAATAAATCACTTTTTATA-
MPSYN61  3' TGTTTTATGTATTAAAACATTTTTATTTAGTGAAAAATAT-
            BglII  SmaI   PstI   EagI
MPSYN60     CTAAGATCTCCCGGGCTGCAGC       3'
MPSYN61     GATTCTAGAGGGCCCGACGTCGCCGG   5'
``` reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Example 5

CONSTRUCTION OF PLASMID pMPCSK1Δ FOR DELETION OF OPEN READING FRAMES [C7L–K1L]

Figure 5:
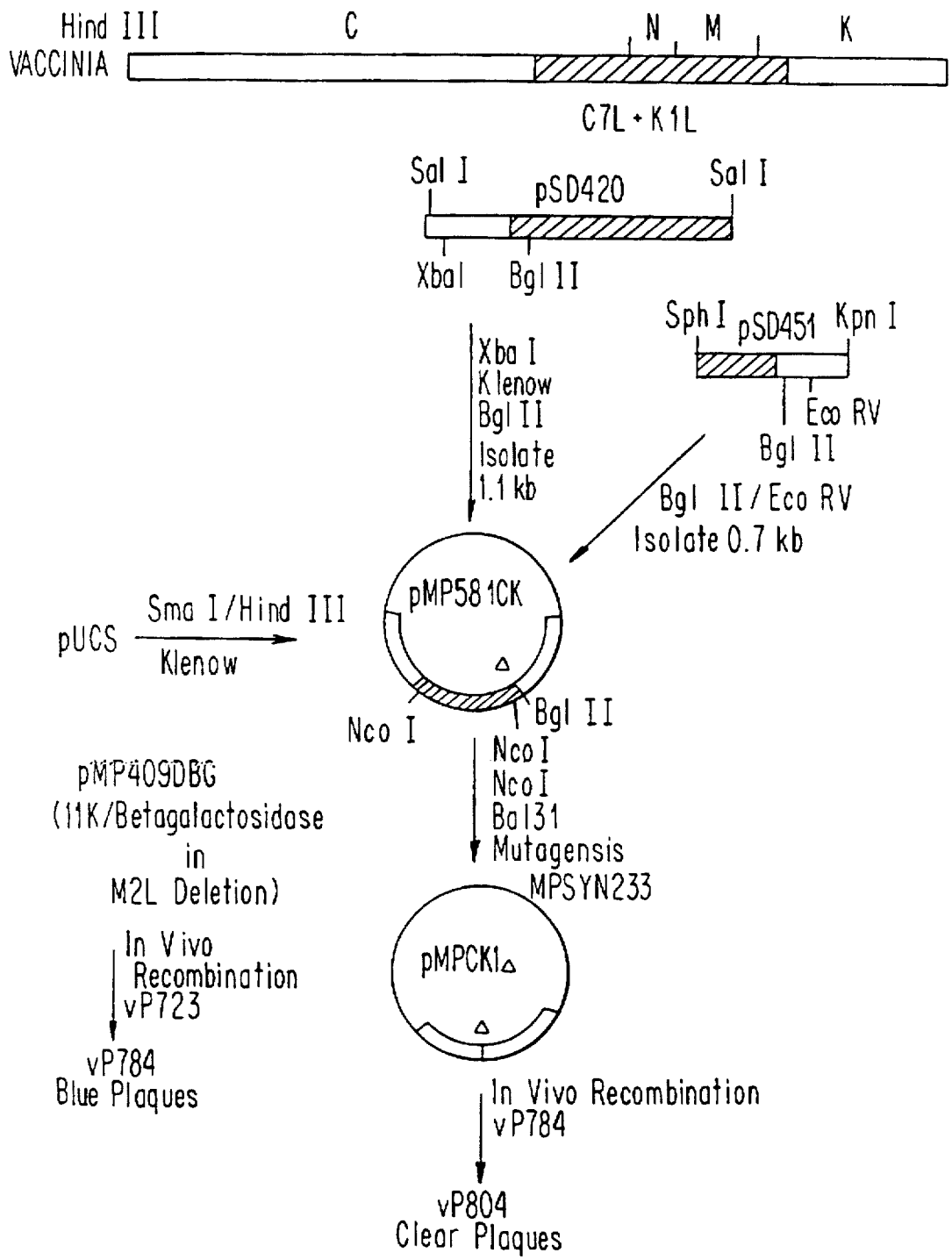
FIG. 5 schematically shows a method for the construction of plasmid pMPCK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

|  | BglII |
|---|---|
| MPSYN82 (SEQ ID NO:19) | 5' TTTCTGTATATTTGCACCAATTTAGATCTT-ACTCAAAATATGTAACAATA 3' |

The resulting plasmid, pMP409D, contains a unique BglII site inserted into the M2L deletion locus as indicated above. A 3.2 kb BamHI (partial)/BglII cassette containing the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of *E. coli* polymerase. The left flanking arm consisting of vaccinia HindIII C sequences was obtained by digestion of pSD420 with XbaI (pos. 18,628) followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTT-AACACTATACTCATATTAATAAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Example 6
CONSTRUCTION OF PLASMID pSD548 FOR DELETION OF LARGE SUBUNIT, RIBONUCLEOTIDE REDUCTASE (I4L)

Figure 6:
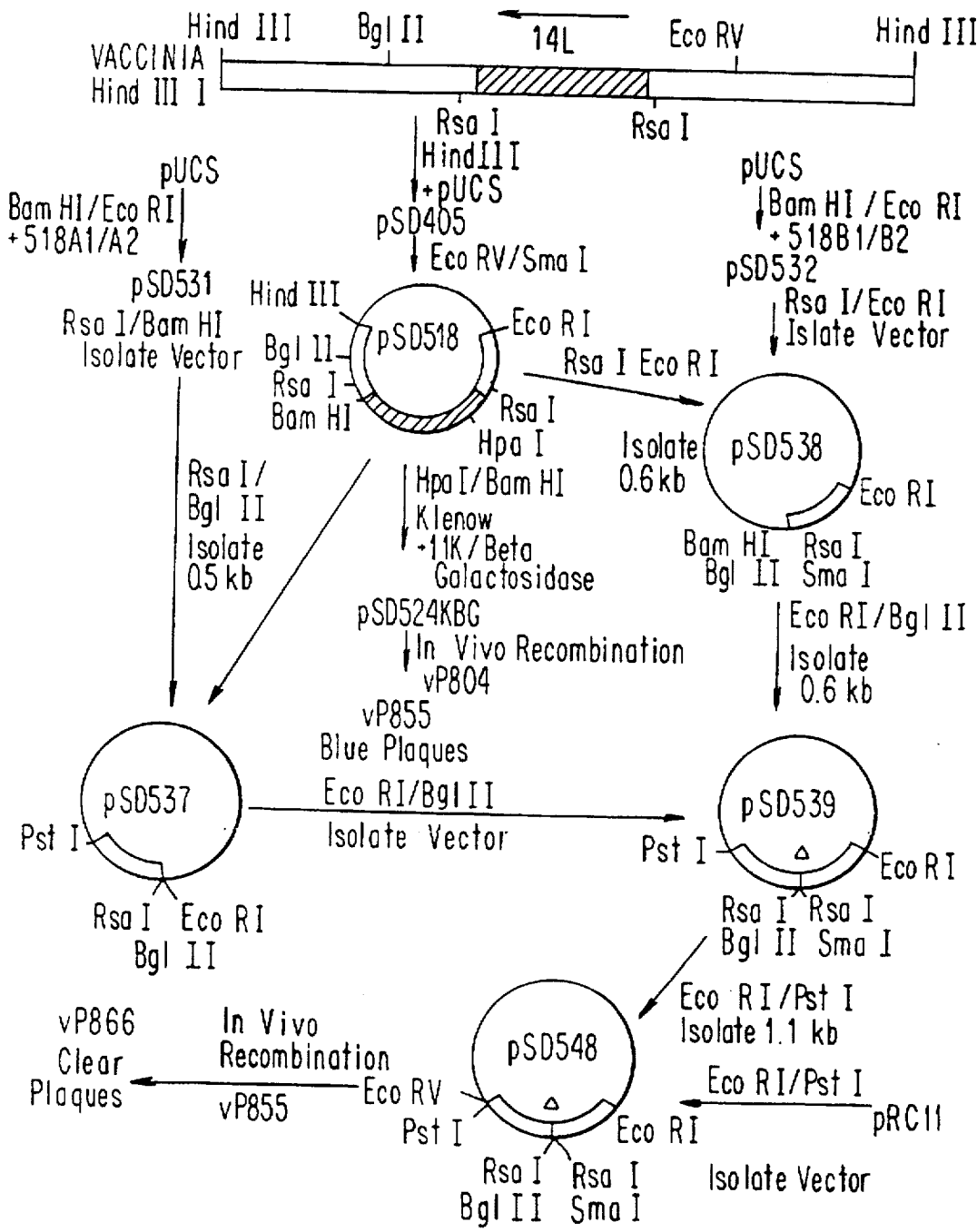
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NOS:21, 22)

|  | BamHI | RsaI |  |  |
|---|---|---|---|---|
| 518A1 | 5' | GATCCTGAGTACTTTGTAATATAATGATATATATTTTCACTTTATCTCAT | | |
| 518A2 | 3' | GACTCATGAAACATTATATTACTATATATAAAAGTGAAATAGAGTA | | |
|  |  | BglII | EcoRI |  |
|  |  | TTGAGAATAAAAAGATCTTAGG | 3' | 518A1 |
|  |  | AACTCTTATTTTTCTAGAATCCTTAA | 5' | 518A2 | forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23, 24)

```
       BamHI   BglII   SmaI
518B1  5'  GATCCAGATCTCCCGGGAAAAAAATTATTTAACTTTTCATTAATAG-
518B2  3'      GTCTAGAGGGCCCTTTTTTTAATAAATTGAAAAGTAATTATC-
                              RsaI      EcoRI
       GGATTTGACGTATGTAGCGTACTAGG          3'  518B1
       CCTAAACTGCATACTACGCATGATCCTTAA      5'  518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 7

INSERTION OF A RABIES GLYCOPROTEIN G GENE INTO NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Figure 7:
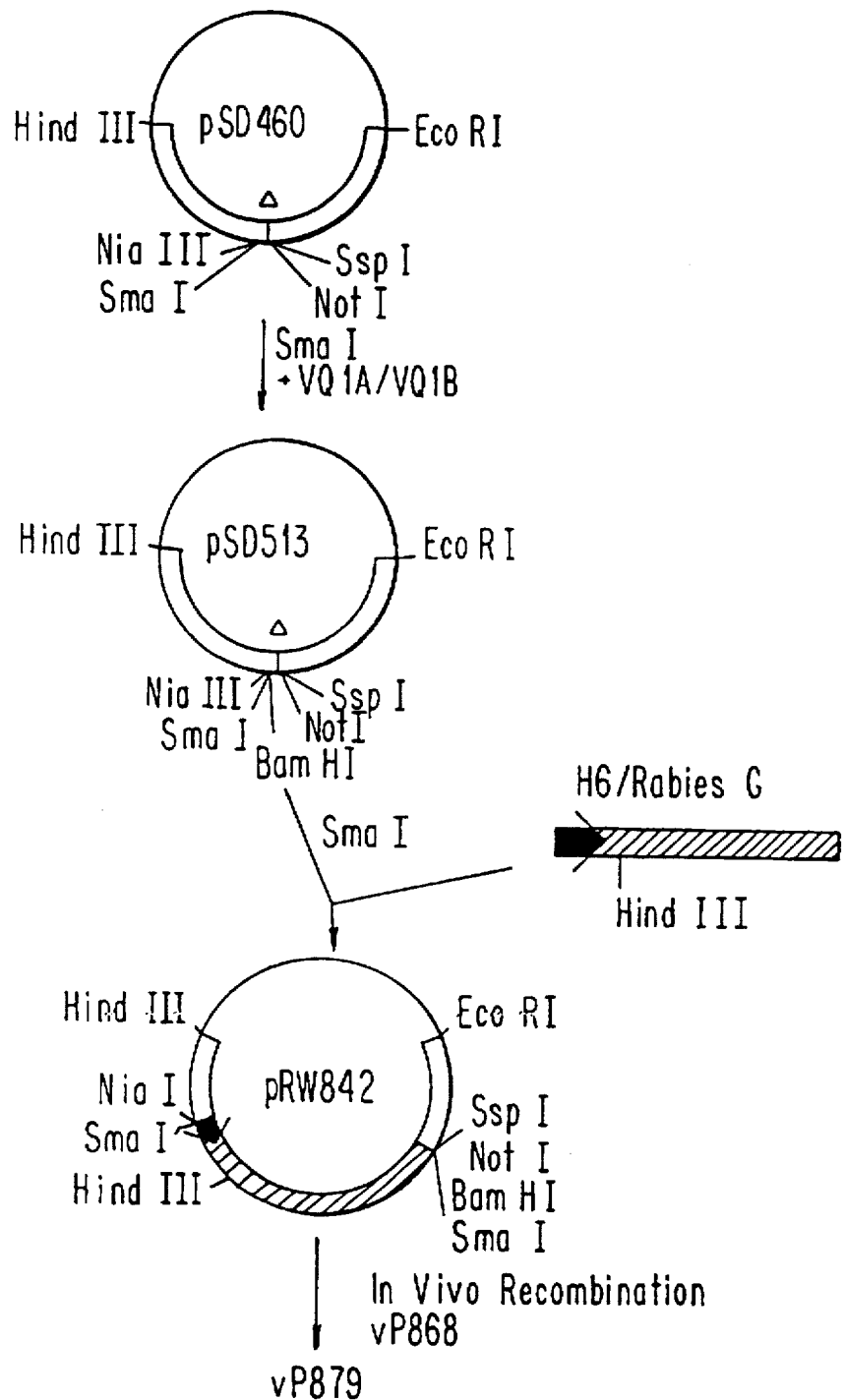
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B (SEQ ID NOS:25, 26)

```
          SmaI  BglII  XhoI   PstI    NarI    BamHI
VQ1A  5'  GGGAGATCTCTCGAGCTGCAGGGCGCCGGATCCTTTTTCT       3'
VQ1B  3'  CCCTCTAGAGAGCTCGACGTCCCGCGGCCTAGGAAAAAGA       5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 8

CONSTRUCTION OF TROVAC-NDV EXPRESSING THE FUSION AND HEMAGGLUTININ-NEURAMINIDASE GLYCOPROTEINS OF NEWCASTLE DISEASE VIRUS

This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses. The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a Cassette for NDV-F. A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into pCE13 by digesting pCE13 with SalI, filling in the sticky ends with Klenow fragment of E. coli DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:27) and CE76 (SEQ ID NO:28) to generate pCE47.

CE75: CGATATCCGTTAAGTTTGTATCG-
TAATGGGCTCCAGATCTTCTACCAG-
GATCCCGGTAC

CE76: CGGGATCCTGGTAGAAGATCTGGAGC-
CCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:29) and CE43 (SEQ ID NO:30) were then inserted to form pCE29.

CE42: AATTCGAGCTCCCCGGG

CE43: CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII-NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:31) and CE167 (SEQ ID NO:32) to generate pCE58.

CE166: CTTTTTATAAAAAGTTAACTACGTAG

CE167: GATCCTACGTAGTTAACTTTT-
TATAAAAAGAGCT

A perfect 3' end for NDV-F was obtained by using the polymerase chain reaction (PCR) with pCE54 as template and oligonucleotides CE182 (SEQ ID NO:33) and CE183 (SEQ ID NO:34) as primers.

CE182: CTTAACTCAGCTGACTATCC

CE183: TACGTAGTTAACTTTTTATAAAAAT-
CATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN. Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:35) and CE163 (SEQ ID NO:36) into the EcoRI site of pRW830 to form pCE59, the final cassette for NDV-HN.

CE162: AATTCAGGATCGTTCCTTTACTAGT-
TGAGATTCTCAAGGATGATGGGATT-
TAATTTTTAT AAGCTTG

CE163: AATTCAAGCTTATAAAAATTAAATC-
CCATCATCCTTGAGAATCTCAACTAG-
TAAAGGAAC GATCCTG

Construction of FPV Insertion Vector. Plasmid pRW731-15 contains a 10 kb PvuII-PvuII fragment cloned from genomic DNA. The nucleotide sequence was determined on both strands for a 3660 bp PvuII-EcoRV fragment. The limits of an open reading frame designated here as F8 were determined. Plasmid pRW761 is a sub-clone of pRW731-15 containing a 2430 bp EcoRV-EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:37) and JCA018 (SEQ ID NO:38).

JCA017:5' CTAGACACTTTATGTTTTTTAATATCCG-
GTCTTAAAAGCTTCCCGGGGATCCTTATACGG
GGAATAAT

JCA018:5' ATTATTCCCCGTATAAGGATCCCCCGG-
GAAGCTTTTAAGACCGGATATTAAAAAA-
CATAA AGTGT

The plasmid resulting from this ligation was designated pJCA002.

Construction of Double Insertion Vector for NDV F and HN. The H6 promoted NDV-HN sequence was inserted into the H6 promoted NDV-F cassette by cloning a HindIII fragment from pCE59 that had been filled in with Klenow fragment of E. coli DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+.

Plasmid pJCA021 was then digested with NdeI and BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV. Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence. Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation. Immunoprecipitation reactions were performed as described (Taylor et al., 1990) using a polyclonal anti-NDV serum obtained from SPAFAS Inc., Storrs, Conn.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO:39) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycosylated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 9

CONSTRUCTION OF ALVAC RECOMBINANTS EXPRESSING RABIES VIRUS GLYCOPROTEIN G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence (SEQ ID NO:39) of this fragment is shown in FIG. 8 between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:40) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:41): ACTCTCAAAAGCTTC-CCGGGAATTCTAGCTAGCTAGTTTTTATAAA

RW146 (SEQ ID NO:42): GATCTTTATAAAAAC-TAGCTAGCTAGAATTCCCGG-GAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E (SEQ ID NO:43–47) are:

A (SEQ ID NO:43): CTGAAATTATTTCATTATCGC-GATATCCGTTAA GTTTGTATCGTAATGGTTCCT-CAGGCTCTCCTGTTTGT

B (SEQ ID NO:44): CATTACGATACAAACTTAACG-GATATCGCGATAA TGAAATAATTTCAG

C (SEQ ID NO:45): ACCCCTTCTGGTTTTTCCGT-TGTGTTTTGGGAAA TTCCCTATTTACACGATC-CCAGACAAGCTTAGATCTCAG

D (SEQ ID NO:46): CTGAGATCTAAGCTTGTCTGG-GATCGTGTAAATA GGGAATTTCCCAAAACA

E (SEQ ID NO:47): CAACGGAAAAACCA-GAAGGGGTACAAACAGGAGA GCCTGAGGAAC

The diagram of annealed oligonucleotides A through E is as follows:

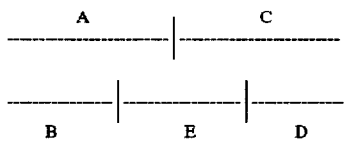

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 9A and 9B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC #CCL81) and MRC-5 cells (a fibroblast-like cell line derived from normal human fetal lung tissue ATCC #CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991c). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell substrates:

(1) Primary chick embryo fibroblast (CEF) cells produced from 11 day old white leghorn embryos;

(2) Vero cells—a continuous line of African Green monkey kidney cells (ATCC #CCL81); and (3) MRC-5 cells—a diploid cell line derived from human fetal lung tissue (ATCC #CCL171).

The initial inoculation was performed at an m.o.i. of 0.1 pfu per cell using three 60 mm dishes of each cell substrate containing $2\times10^6$ cells per dish. One dish was inoculated in the presence of 40 µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell substrate was inoculated undiluted onto three dishes of the same cell substrate (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the to sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell substrate was inoculated onto a permissive CEF monolayer and harvested at cytopathic effect (CPE) or at 7 days if no CPE was evident. The results of this experiment are shown in Table 3. Even after amplification through a permissive cell substrate, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1\times10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 μl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 μl instilled on the surface of the right eye without scarification; (2) 100 μl as several droplets in the mouth; (3) 100 μl in each of two intradermal injection sites in the shaven skin of the external face of the right arm; and (4) 100 μl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC #CCL81;

(b) MRC-5, human embryonic lung, ATCC #CCL 171;

(c) WISH human amnion, ATCC #CCL 25;

(d) Detroit-532, human foreskin, Downs's syndrome, ATCC #CCL 54; and (e) Primary CEF cells.

Chicken embryo fibroblast cells produced from 11 day old white leghorn embryos were included as a positive control. All inoculations were performed on preformed monolayers of $2\times10^6$ cells as discussed below.

A. Methods for DNA analysis

Three dishes of each cell line were inoculated at 5 pfu/cell of the virus under test, allowing one extra dish of each cell line un-inoculated. One dish was incubated in the presence of 40 μg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of 2×10⁶ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 µg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of ³⁵S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by ³H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on ³⁵S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 log$_{10}$ TCID$_{50}$ per ml were serially diluted and 50 to 100 µl of dilutions inoculated into the footpad of four to six week old mice. Mice were challenged 14 days later by the intracranial route with 300 µl of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 6. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 μl of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 $\log_{10}$ mouse LD$_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ TCID$_{50}$ had antibody titers on day 14 post-vaccination and all dogs had titers at 29 days. All dogs were protected from a challenge which killed three out of four controls. In cats, three of five cats receiving 6.7 $\log_{10}$ TCID$_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ TCID$_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An anamnestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

| Sequential Passage of ALVAC in Avian and non-Avian Cells. | | | |
|---|---|---|---|
| | CEF | Vero | MRC-5 |
| Pass 1 Sample | | | |
| t0[a] | 2.4 | 3.0 | 2.6 |
| t7[b] | 7.0 | 1.4 | 0.4 |
| t7A[c] | 1.2 | 1.2 | 0.4 |
| Pass 2 Sample | | | |
| t0 | 5.0 | 0.4 | N.D.[d] |
| t7 | 7.3 | 0.4 | N.D. |
| t7A | 3.9 | N.D. | N.D. |
| Pass 3 Sample | | | |
| t0 | 5.4 | 0.4 | N.D. |
| t7 | 7.4 | N.D. | N.D. |
| t7A | 3.8 | N.D. | N.D. |
| Pass 4 Sample | | | |
| t0 | 5.2 | N.D. | N.D. |
| t7 | 7.1 | N.D. | N.D. |
| t7A | 3.9 | N.D. | N.D. |

[a] This sample was harvested at zero time and represents the residual input virus. The titer is expressed as $\log_{10}$pfu per ml.
[b] This sample was harvested at 7 days post-infection.
[c] This sample was inoculated in the presence of 40 μg/ml of Cytosine arabinoside and harvested at 7 days post infection.
[d] Not detectable

TABLE 2

| Sequential Passage of ALVAC-RG in Avian and non-Avian Cells | | | |
|---|---|---|---|
| | CEF | Vero | MRC-5 |
| Pass 1 | | | |
| Sample t0[a] | 3.0 | 2.9 | 2.9 |

TABLE 2-continued

Sequential Passage of ALVAC-RG in Avian and non-Avian Cells

| | CEF | Vero | MRC-5 |
|---|---|---|---|
| t7[b] | 7.1 | 1.0 | 1.4 |
| t7A[c] | 1.8 | 1.4 | 1.2 |
| Pass 2 | | | |
| Sample | | | |
| t0 | 5.1 | 0.4 | 0.4 |
| t7 | 7.1 | N.D.[d] | N.D. |
| t7A | 3.8 | N.D. | N.D. |
| Pass 3 | | | |
| Sample | | | |
| t0 | 5.1 | 0.4 | N.D. |
| t7 | 7.2 | N.D. | N.D. |
| t7A | 3.6 | N.D. | N.D. |
| Pass 4 | | | |
| Sample | | | |
| t0 | 5.1 | N.D. | N.D. |
| t7 | 7.0 | N.D. | N.D. |
| t7A | 4.0 | N.D. | N.D. |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post-infection.
[d]Not detectable.

TABLE 3

Amplification of residual virus by passage in CEF cells

| | CEF | Vero | MRC-5 |
|---|---|---|---|
| a) ALVAC | | | |
| Pass | | | |
| 2[a] | 7.0[b] | 6.0 | 5.2 |
| 3 | 7.5 | 4.1 | 4.9 |
| 4 | 7.5 | N.D.[c] | N.D. |
| 5 | 7.1 | N.D. | N.D. |
| b) ALVAC-RG | | | |
| Pass | | | |
| 2[a] | 7.2 | 5.5 | 5.5 |
| 3 | 7.2 | 5.0 | 5.1 |
| 4 | 7.2 | N.D. | N.D. |
| 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 4

Schedule of inoculation of rhesus macaques with ALVAC-RG (vCP65)

| Animal | | Inoculation |
|---|---|---|
| 176L | Primary: | $1 \times 10^8$ pfu of vCP65 orally in TANG |
| | Secondary: | $1 \times 10^7$ pfu of vCP65 plus $1 \times 10^7$ |

TABLE 4-continued

Schedule of inoculation of rhesus macaques with ALVAC-RG (vCP65)

| Animal | | Inoculation |
|---|---|---|
| | | pfu of vCP82[a] by SC route |
| 185L | Primary: | $1 \times 10^8$ pfu of vCP65 orally in Tang |
| | Secondary: | $1 \times 10^7$ pfu of vCP65 plus $1 \times 10^7$ |
| | | pfu of vCP82 by SC route |
| 177L | Primary: | $5 \times 10^7$ pfu SC of vCP65 by SC route |
| | Secondary: | $1 \times 10^7$ pfu of vCP65 plus $1 \times 10^7$ |
| | | pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ |
| | | pfu of vCP82 by SC route |
| 178L | Primary: | $1 \times 10^7$ pfu of vCP65 by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP6S orally |

[a]vCP82 is a canarypox virus recombinant expressing the measles virus fusion and hemagglutinin genes.

TABLE 5

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 6

Potency of ALVAC-RG as tested in mice

| Test | Challenge Dose[a] | $PD_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse $LD_{50}$
[b]Expressed as $\log_{10}$ $TCID_{50}$

TABLE 7

Efficacy of ALVAC-RG in dogs and cats

| Dose | Dogs | | Cats | |
|---|---|---|---|---|
| | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 8

Anti-rabies serological response of squirrel monkeys inoculated with canarypox recombinants

| Monkey # | Previous Exposure | Rabies serum-neutralizing antibody[a] | | | | | | |
|---|---|---|---|---|---|---|---|---|
| | | -196b | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ TCID$_{50}$ of ALVAC
[d]Animals received 5.0 $\log_{10}$ TCID$_{50}$ of vCP37
[e]Animals received 5.0 $\log_{10}$ TCID$_{50}$ of ALVAC-RG
[f]Animals received 7.0 $\log_{10}$ TCID$_{50}$ of ALVAC-RG
[g]Not tested.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b/0] | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation

Example 10

IMMUNIZATION OF HUMANS USING CANARYPOX EXPRESSING RABIES GLYCOPROTEIN (ALVAC-RG; vCP65)

Figure 9A:
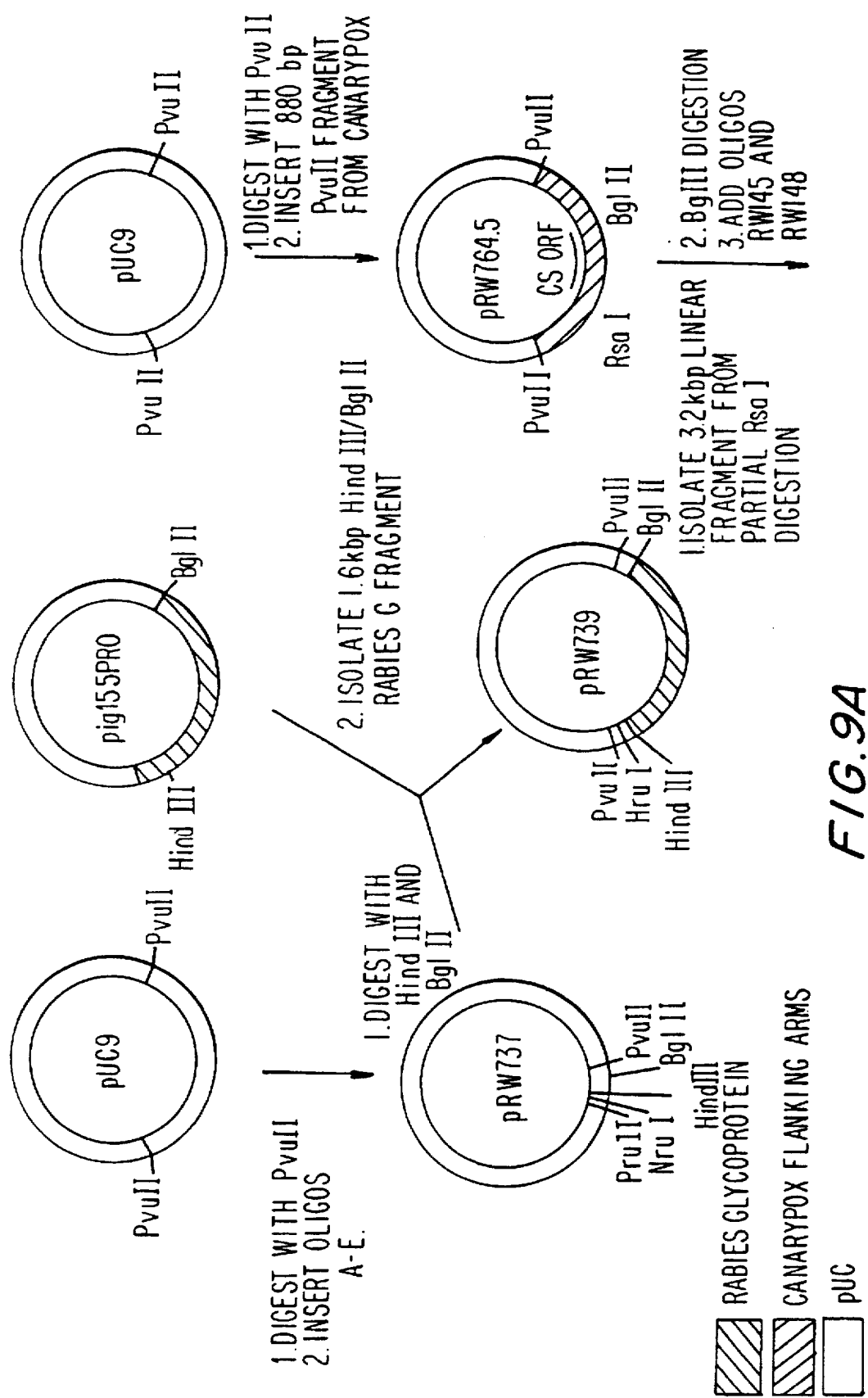
FIGS. 9A and 9B schematically show a method for the construction of recombinant canarypox virus vCP65 (ALVAC-RG)
Figure 9B:
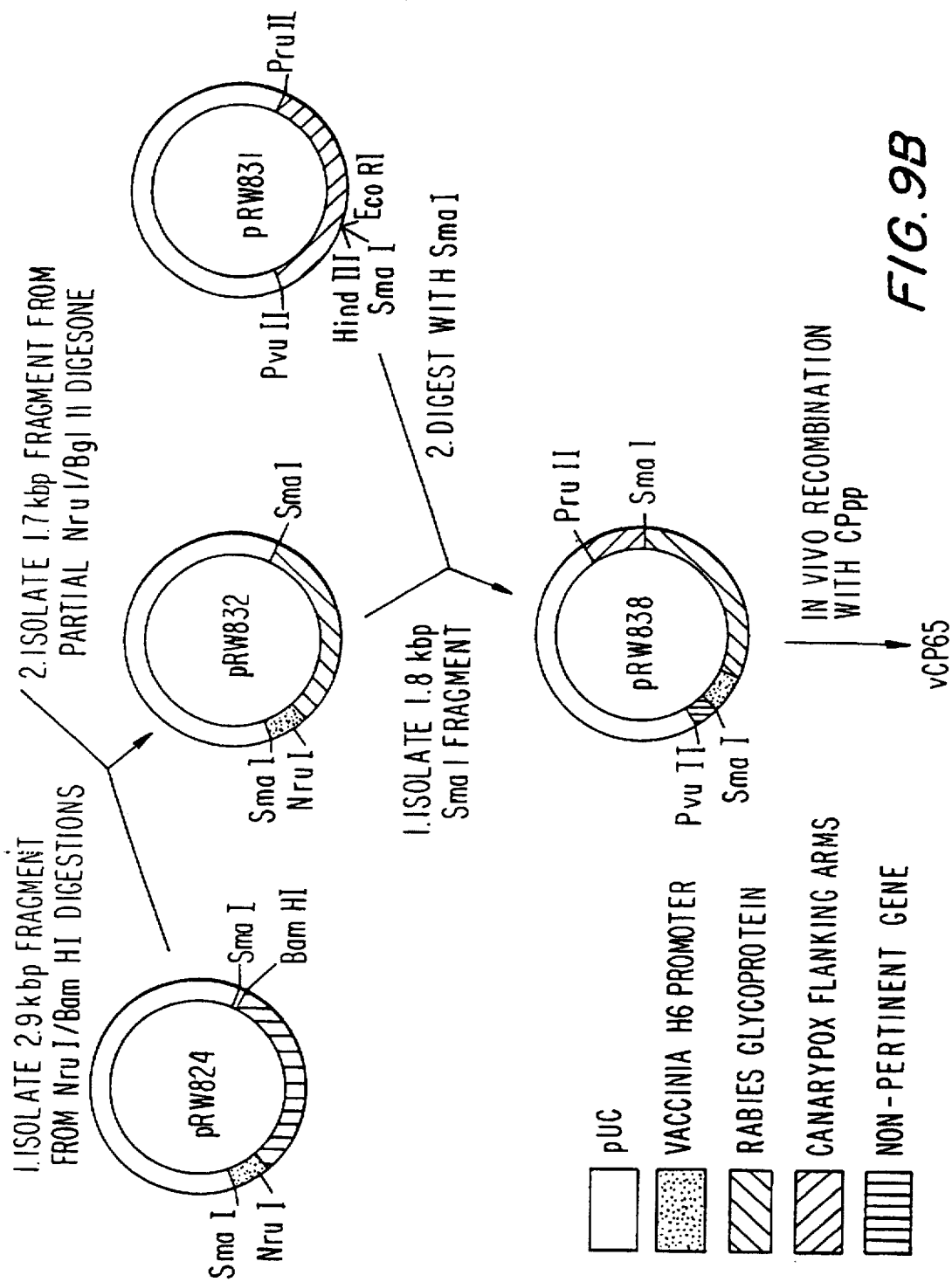

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.1 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of

TABLE 9

Inoculation of rhesus macaques with ALVAC-RG[a]

| Days post-Inoculation | Route of Primary Inoculation | | | | | | | | | |
|---|---|---|---|---|---|---|---|---|---|---|
| | or/Tang 176L[b] | SC 185L | SC 177L | SC 186L | SC 178L | IM 182L | SC 179L | IM 183L | SC 180L | IM 184L | OR 187L[b] |
| -84 | — | — | | — | | | | | | | |
| -9 | | — | — | | — | | — | | | | |
| 3 | | | — | — | | | | | | | |
| 6 | | — | ± | ± | | | | | | | |
| 11 | | — | 16[d] | 128 | | | | | | | |
| 19 | | — | 32 | 128 | — | | — | | | | |
| 35 | | — | 32 | 512 | | | | | | | |
| 59 | | — | 64 | 256 | | | | | | | |
| 75 | | — | 64 | 128 | — | | — | | | | |
| 99[c] | | — | 64 | 256 | — | — | — | — | — | — | — |
| 2 | | — | 32 | 256 | — | — | — | — | — | — | — |
| 6 | | — | 512 | 512 | — | — | — | — | — | — | — |
| 15 | 16 | 16 | 512 | 512 | 64 | 32 | 64 | 128 | 32 | — | — |
| 29 | 16 | 32 | 256 | 256 | 64 | 64 | 32 | 128 | 32 | — | — |
| 55 | | 32 | | | | 32 | | 32 | 16 | — | |
| 57 | 16 | | 128 | 128 | 16 | | 16 | | | | — |

[a]See Table 9 for schedule of inoculations.
[b]Animals 176L and 185L received 8.0 $\log_{10}$ pfu by the oral route in 5 ml Tang. Animal 187L received 7.0 $\log_{10}$ pfu by oral route not in Tang.
[c]Day of re-vaccination for animals 187L, 185L, 177L and 186L by S.C. route, and primary vaccination for animals 178L, 182L, 179L, 183L, 184L and 187L.
[d]Titers expressed as reciprocal of last dilution showing inhibition of fluorescence in an RFFI test.

the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC-HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith et al., 1973). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 12). Twenty eight days after the first injection all the HDC recipients had protective titers (≧0.5 IU/ml). By contrast none in groups A and B ($10^{3.5}$ and $10^{4.5}$ TCID$_{50}$) and only 2/9 in group C. ($10^{5.5}$ TCID$_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C. recipients of ALVAC-RG (vCP65) vaccine and persisted in all 10 HDC recipients.

At day 56 the geometric mean titers were 0.05, 0.47, 4.4 and 11.5 IU/ml in groups A, B, C. and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The preimmune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C. whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIGS. 13A–13D shows graphs of rabies neutralizing antibody titers (Rapid Fluorescent Focus Inhibition Test or RFFIT, IU/ml): Booster effect of HDC and vCP65 ($10^{5.5}$ TCID$_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 13A to 13D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)–ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., 1991; Etinger et al., 1991).

Thus, this Example clearly demonstrates that a non-replicating poxvirus can serve as an immunizing vector in humans, with all of the advantages that replicating agents confer on the immune response, but without the safety problem created by a fully permissive virus.

TABLE 11

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

Reactions in the 5 days following vaccination

TABLE 12

Rabies neutralizing antibodies (RFFIT; IU/ml)
Individual titers and geometric mean titers (GMT)

| No. | TCID50/ dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |

TABLE 12-continued

Rabies neutralizing antibodies (REFIT; IU/ml)
Individual titers and geometric mean titers (GMT)

| No. | TCID50/ dose | Days |  |  |  |  |
|---|---|---|---|---|---|---|
|  |  | 0 | 7 | 28 | 35 | 56 |
| 10 | $10^{4.5}$ | <0.1 | <0.1 | <0.1 | 1.6 | 1.1 |
|  | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
|  | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
|  | G.M.T. | <0.1 | <0.1 | 2.96 | 9.0 | 11.5* |

*p = 0.007 student t test

TABLE 13

Canarypox antibodies: ELISA Geometric Mean Titers*

| vCP65 dosage TCID50/dose | Days |  |  |  |  |
|---|---|---|---|---|---|
|  | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 11

COMPARISON OF THE LD$_{50}$ OF ALVAC AND NYVAC WITH VARIOUS VACCINIA VIRUS STRAINS

Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated for plaque forming units in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population (LD$_{50}$) was determined by the proportional method of Reed and Muench.

Comparison of the LD$_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 14). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses (3.85×10$^8$ PFUs, ALVAC and 3×10$^8$ PFUs, NYVAC) by an undetermined mechanism by this route of inoculation.

Comparison of the LD$_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, LD$_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, 6.3×10$^7$ PFUs, 100% mortality resulted. Mortality rates of 33.3% were observed at 6.3×10$^6$ PFUs. The cause of death, while not actually determined, was not likely of toxicological or traumatic nature since the mean survival time (MST) of mice of the highest dosage group (approximately 6.3 LD$_{50}$) was 6.7±1.5 days. When compared to WR(L) at a challenge dose of 5 LD$_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, 6×10$^8$ and 6×10$^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 $LD_{50}$, survived to day 4.

TABLE 14

Calculated 50% Lethal Dose for mice by various vaccinia virus strains and for canarypox virus (ALVAC) by the ic route

| POXVIRUS STRAIN | CALCULATED $LD_{50}$ (PFUs) |
|---|---|
| WR(L) | 2.5 |
| VC-2 | $1.26 \times 10^4$ |
| WYETH | $5.00 \times 10^4$ |
| NYVAC | $1.58 \times 10^8$ |
| ALVAC | $1.58 \times 10^8$ |

TABLE 15

Calculated 50% Lethal Dose for newborn mice by various vaccinia virus strains and for canarypox virus (ALVAC) by the ic route.

| POXVIRUS STRAIN | CALCULATED $LD_{50}$ (PFUs) |
|---|---|
| WR(L) | 0.4 |
| VC-2 | 0.1 |
| WYETH | 1.6 |
| NYVAC | $1.58 \times 10^6$ |
| ALVAC | $1.00 \times 10^7$ |

Example 12

EVALUATION OF NYVAC (vP866) AND NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trimarchi, Griffith Laboratories, New York State Department of Health, Albany, N.Y., and a rat anti-mouse conjugate obtained from Boehringer Mannheim Corporation (Cat. #605–500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per µl for untreated mice (n=4) and 4,220 cells per µl for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 µl of a range of dilutions (2.0–8.0 $log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Figure 10:
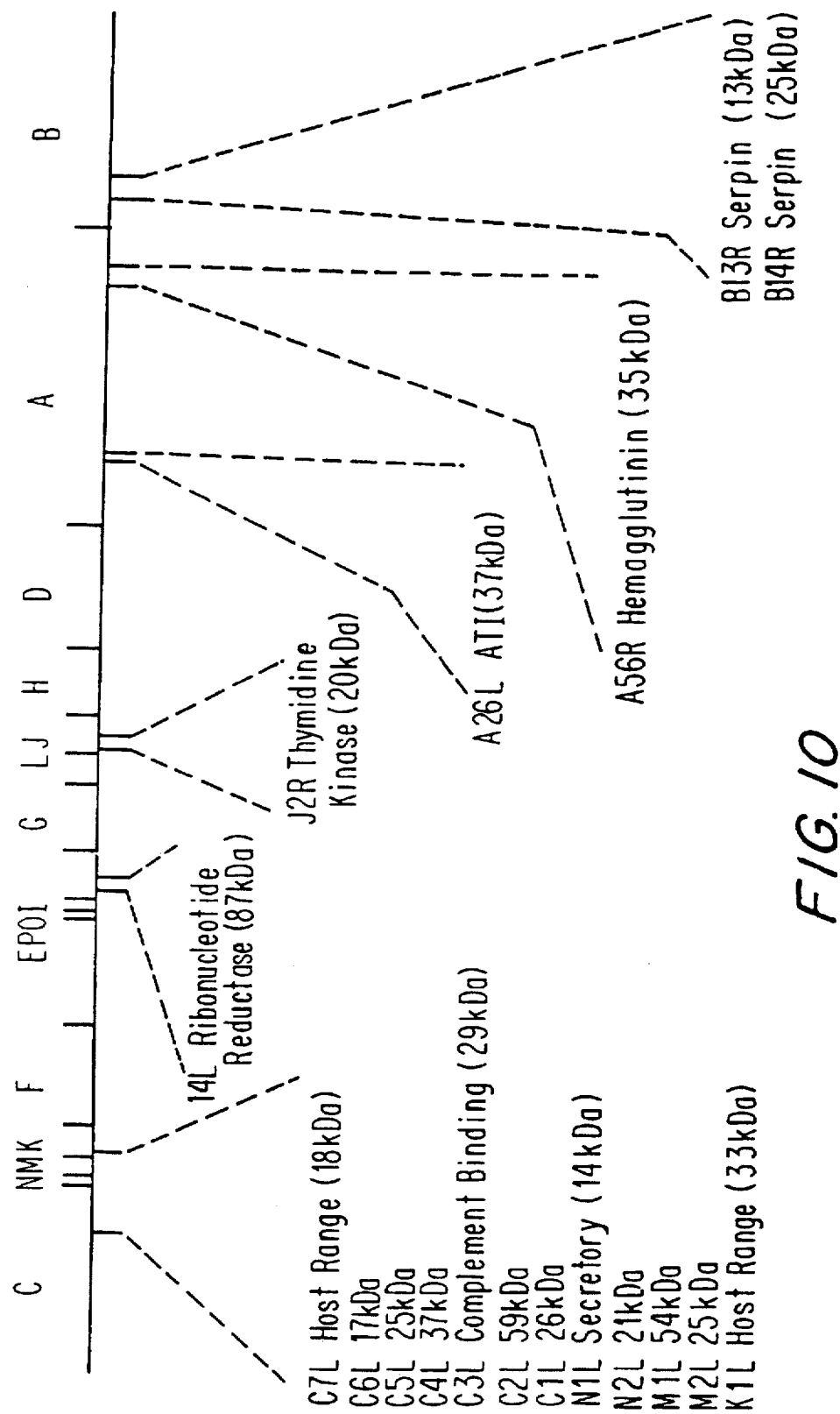
FIG. 10 shows schematically the ORFs deleted to generate NYVAC.
Figure 13A:
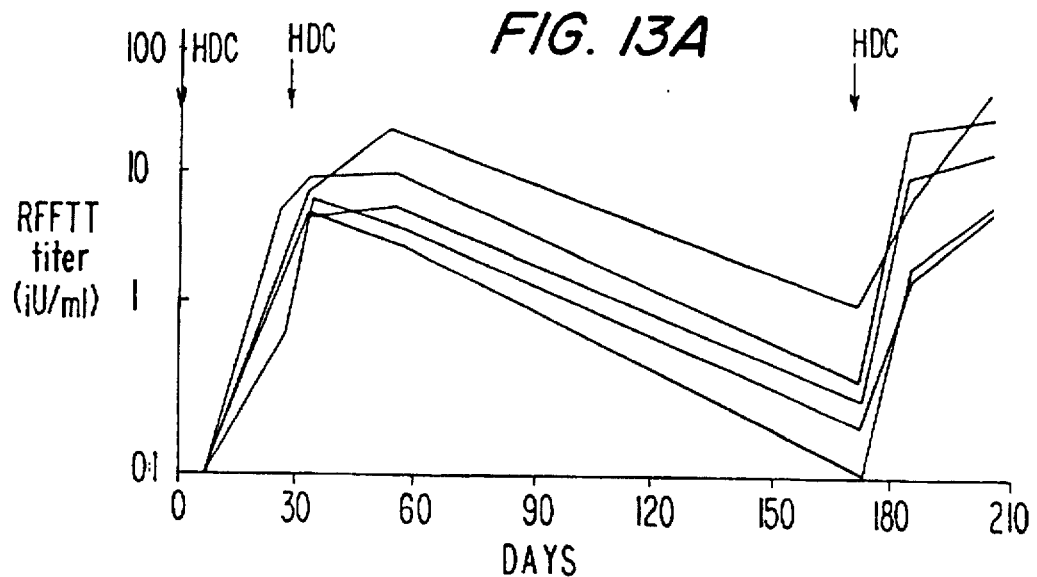
FIGS. 13A to 13D show graphs of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208)
Figure 13C:
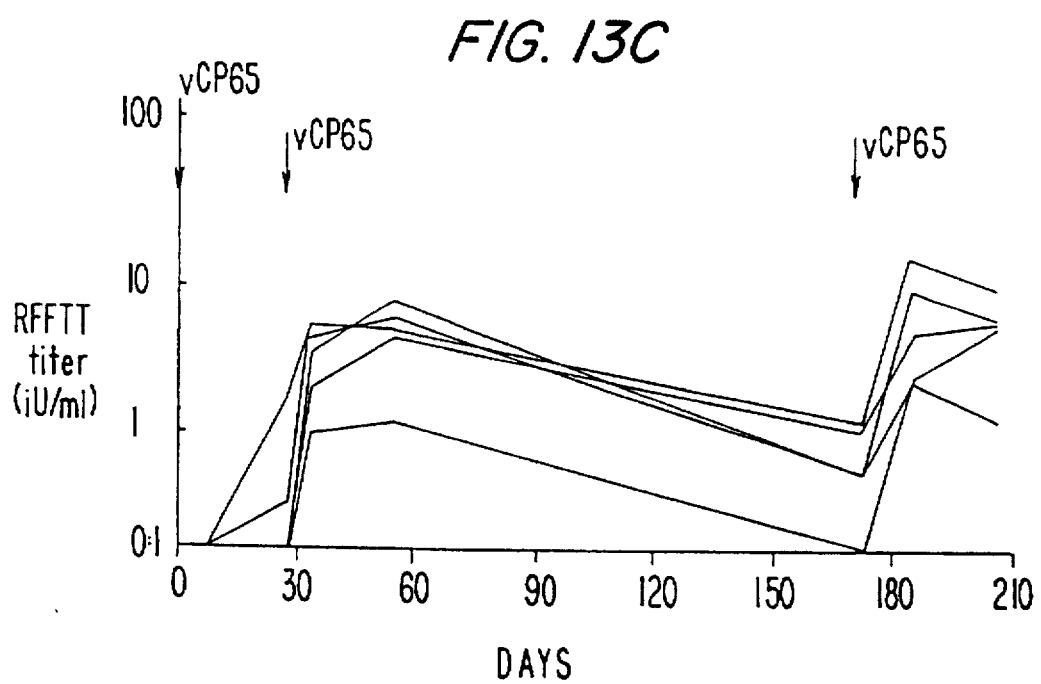
Figure 13B:
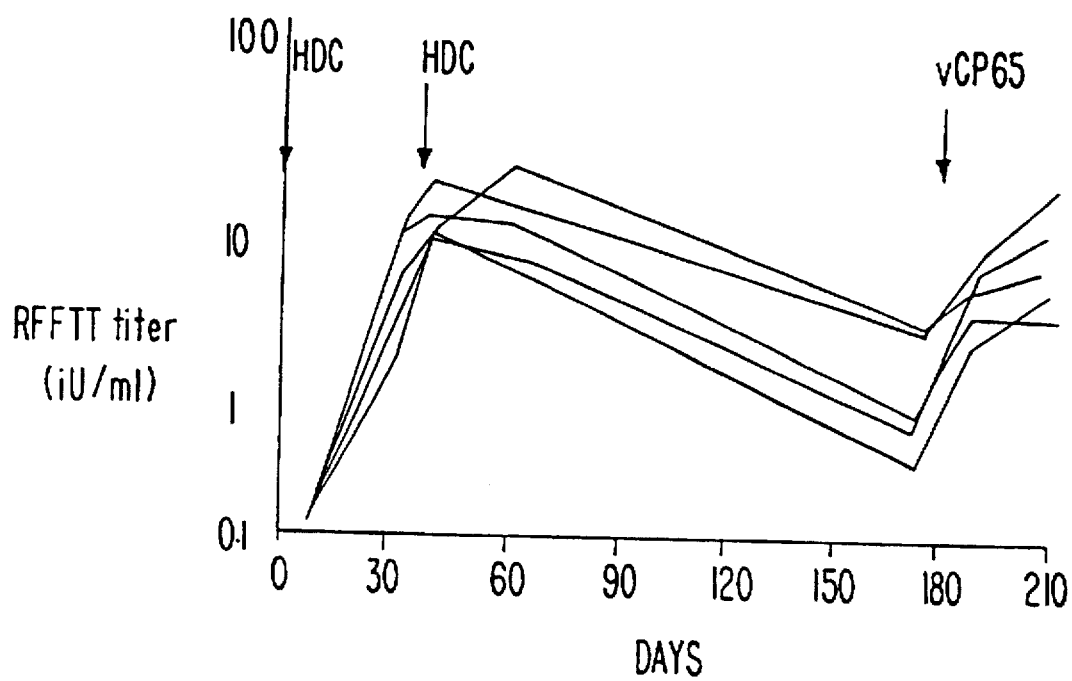
Figure 13D:
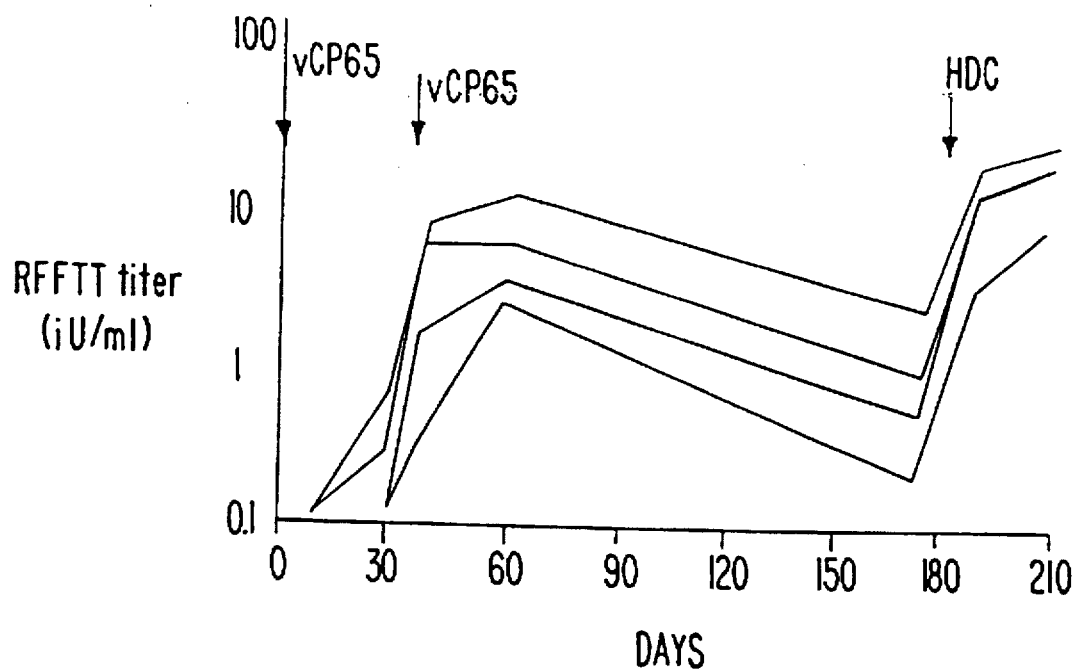

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contrast, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70–151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5\times10^4$ to $9.5\times10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65\times10^5$ to $1.65\times10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 17 and 18). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of specific virulence-associated genes in NYVAC prevents lesion occurrence.

Together, the results in this Example and in foregoing Examples, including Example 11, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1992). Furthermore, the use of NYVAC as a general laboratory expression vector system may greatly reduce the biological hazards associated with using vaccinia virus.

By the following criteria, the results of this Example and the Examples herein, including Example 11, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |

TABLE 16-continued

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 µg/ml of cytosine arabinoside.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | 10[4] | 386 | 30 | 88 | 30 |
| | 10[5] | 622 | 35 | 149 | 32 |
| | 10[6] | 1057 | 34 | 271 | 34 |
| | 10[7] | 877 | 35 | 204 | 35 |
| | 10[8] | 581 | 25 | 88 | 26 |
| WYETH | 10[4] | 32 | 5 | —[d] | — |
| | 10[5] | 116 | 15 | — | — |
| | 10[6] | 267 | 17 | 3 | 15 |
| | 10[7] | 202 | 17 | 3 | 24 |
| | 10[8] | 240 | 29 | 12 | 31 |
| VC-2 | 10[4] | 64 | 7 | — | — |
| | 10[5] | 86 | 8 | — | — |
| | 10[6] | 136 | 17 | — | — |
| | 10[7] | 167 | 21 | 6 | 10 |
| | 10[8] | 155 | 32 | 6 | 8 |
| NYVAC | 10[4] | — | — | — | — |
| | 10[5] | — | — | — | — |
| | 10[6] | — | — | — | — |
| | 10[7] | — | — | — | — |
| | 10[8] | — | — | — | — |

[a]pfu of indicated vaccinia virus in 0.1 ml PBS inoculated intradermally into one site.
[b]mean maximum size of lesions (mm$^2$)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |

TABLE 18-continued

| Persistence of poxviruses at the site of intradermal inoculation | | |
|---|---|---|
| Virus | Inoculum Dose | Total Virus Recovered |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]expressed as $\log_{10}$ pfu.

TABLE 19

| Virulence studies in immunocompromised mice | | |
|---|---|---|
| | $LD_{50}$[a] | |
| Poxvirus Strain | Nude mice | Cyclophosphamide treated mice |
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $\geqq 5.00 \times 10^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of $5 \times 10^8$ pfu.

TABLE 20

| Comparative efficacy of NYVAC-RG and ALVAC-RG in mice | |
|---|---|
| Recombinant | $PD_{50}$[a] |
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $\log_{10}$ tissue culture infection dose 50% ($TCID_{50}$) of either the VV-RG (Kieny et al., 1984), ALVAC-RG (vCP65) or NYVAC-RG (vP879). At aday 14, mice of each group were challenged by intracranial inoculation of 30 μl of a live CVS strain rabies virus corresponding to 15 lethal dose 50% ($LD_{50}$) per mouse. At day 28, surviving mice were counted and a protective dose 50% ($PD_{50}$) was calculated.

Example 13

CONSTRUCTION OF TROVAC RECOMBINANTS EXPRESSING THE HEMAGGLUTININ GLYCOPROTEINS OF AVIAN INFLUENZA VIRUSES

This Example describes the development of fowlpox virus recombinants expressing the hemagglutinin genes of three serotypes of avian influenza virus.

Cells and Viruses. Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus. Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 11 (SEQ ID NO:48). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:37) and JCA018 (SEQ ID NO:38).

JCA017 (SEQ ID NO:37) 5' CTAGACACTTTATGTTTTTTAATATCCGGTCTT AAAAGCTTCCCGGGGATCCTTATACGGGGAATAAT 3'

JCA018 (SEQ ID NO:38) 5' ATTATTCCCCGTATAAGGATCCCCCGGGAA GCTTTTAAGACCGGATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:49) and RW179 (SEQ ID NO:50) were cut with EcoRV and BamHI and inserted between the EcoRV and BamHI sites of JCA004 to form pRW846.

RW178 (SEQ ID NO:49): 5' TCATTATCGCGATATCCGTGTTAACTAGCTA GCTAATTTTTATTCCCGGGATCCTTATCA 3'

| | |
|---|---|
| RW179 (SEQ ID NO:50): | 5' GTATAAGGATCCCGGGAATAAAAATTAGCT AGCTAGTTAACACGGATATCGCGATAATGA 3' |

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus. The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 12 (SEQ ID NO:51) was determined for a 2356 bp region encompassing the unique HincII site. Analysis of this sequence revealed that the unique HincII site (FIG. 12, underlined) was situated within an ORF encoding a polypeptide of 90 amino acids. The ORF begins with an ATG at position 1531 and terminates at position 898 (positions marked by arrows in FIG. 12).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:52) (5'-GACAATCTAAGTCCTATATTAGAC-3') and F73PB (SEQ ID NO:53) (5'-GGATTTTTAGGTAGACAC-3'). A 270 bp arm (designated as EH) corresponding to the region downstream from the ORF was amplified using oligonucleotides F75PE (SEQ ID NO:54) (5'-TCATCGTCTTCATCATCG-3') and F73PH1 (SEQ ID NO:55) (5'-GTCTTAAACTTATTGTAAGGGTATACCTG-3').

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the *E. coli* DNA polymerase in the presence of 2 mM dNTPs. This linearized plasmid was ligated with annealed oligonucleotides F7MCSB (SEQ ID NO:56) (5'-AACGATTAGTTAGTTACTAAAAGCT-TGCTGCAGCCCGGGTTTTTTATTAGTTTAGTTAGTC-3') and F7MCSA (SEQ ID NO:57) (5'-GACTAACTAACTAATAAAAAA CCCGGGCTGCAGCAAGCTTTTTGTAACTAACTAAT-CGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus. A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:58) and RW153 (SEQ ID NO:59). These oligonucleotides represent the 3' portion of the H6 promoter from the EcoRV site and align the ATG of the promoter with the ATG of the H4 cDNA.

| | |
|---|---|
| RW152 (SEQ ID NO:58): | 5' GCACGGAACAAAGCTTATCGCGATATCCGTTA AGTTTGTATCGTAATGCTATCAATCACGATTCTGT TCCTGCTCATAGCAGAGGGCTCATCTCAGAAT 3' |
| RW153 (SEQ ID NO:59): | 5' ATTCTGAGATGAGCCCTCTGCTATGAGCAGGA ACAGAATCGTGATTGATAGCATTACGATACAAACT TAACGGATATCGCGATAAGCTTTGTTCCGTGC 3' |

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

Construction of Insertion Plasmid for H5 Hemagglutinin at the F8 Locus. A cDNA clone of avian influenza H5 derived from A/Turkey/Ireland/1378/83 was received in plasmid pTH29 from Dr. R. Webster. Synthetic oligonucleotides RW10 (SEQ ID NO:60) through RW13 (SEQ ID NO:63) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

| | |
|---|---|
| RW10 (SEQ ID NO:60): | 5' GAAAAATTTAAAGTCGACCTGTTTTGTTGAGT TGTTTGCGTGGTAACCAATGCAAATCTGGTC ACT 3' |
| RW11 (SEQ ID NO:61): | 5' TCTAGCAAGACTGACTATTGCAAAAAGAAGCA CTATTTCCTCCATTACGATACAAACTTAACG GAT 3' |
| RW12 (SEQ ID NO:62): | 5' ATCCGTTAAGTTTGTATCGTAATGGAGGAAA TAGTGCTTCTTTTTGCAATAGTCAGTCTTGCTAGA AGTGACCAGATTTGCATTGGT 3' |
| RW13 (SEQ ID NO:63): | 5' TACCACGCAAACAACTCAACAAAACAGGTCG ACTTTAAATTTTTCTGCA 3' |

The oligonucleotides were annealed at 95° C. for three minutes followed by slow cooling at room temperature. This results in the following double strand structure with the indicated ends.

```
EcoRV                                          PstI
|          RW12          |        RW13         |
----------                                 ---------
         |       RW11          |     RW10        |
```

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp pRW759 EcoRV-DraI fragment containing the 3' H6 promoter and the H5 gene was inserted between the EcoRV and HincII sites of pRW846 (previously described). The resulting plasmid pRW849 contains the H6 promoted avian influenza virus H5 gene in the de-ORFed F8 locus.

Construction of Insertion Vector for H7 Hemagglutinin at the F7 Locus. Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:64) and RW166 (SEQ ID NO:65) were annealed, cut with HincII and StyI and inserted between the EcoRV and StyI sites of pRW827 to generate pRW845.

| | |
|---|---|
| RW165 (SEQ ID NO:64): | 5' GTACAGGTCGACAAGCTTCCCGGGTATCGCG ATATCCGTTAAGTTTGTATCGTAATGAATACTCAA ATTCTAATACTCACTCTTGTGGCAGCCATTCACAC AAATGCAGACAAAATCTGCCTTGGACATCAT 3' |
| RW166 (SEQ ID NO:65): | 5' ATGATGTCCAAGGCAGATTTTGTCTGCATTTG TGTGAATGGCTGCCACAAGAGTGAGTATTAGAATT TGAGTATTCATTACGATACAAACTTAACGGATATC GCGATACCCGGGAAGCTTGTCGACCTGTAC 3' |

Oligonucleotides RW165 (SEQ ID NO:64) and RW166 (SEQ ID NO:65) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:66) and RW228 (SEQ ID NO:67). The resulting plasmid was pRW854.

| | |
|---|---|
| RW227 (SEQ ID NO:66): | 5' ATAACATGCGGTGCACCATTTGTATAT AAGTTAACGAATTCCAAGTCAAGC 3' |
| RW228 (SEQ ID NO:67): | 5' GCTTGACTTGGAATTCGTTAACTTATA TACAAATGGTGCACCGCATGTTAT 3' |

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the SmaI site of pF7D0 described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the *E. coli* DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants. Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence. In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the $HA_2$ cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_0$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 14

GENERATION OF NYVAC RECOMBINANT CONTAINING THE CANINE DISTEMPER VIRUS (ONDERSTEPOORT STRAIN) HEMAGGLUTININ ORF

The Onderstepoort strain of canine distemper virus (CDV) was obtained from Dr. M. Appel (Cornell University, Ithaca, N.Y.). RNA was harvested from CDV infected Vero cells and cDNA was prepared in the following manner.

RNA from CDV infected Vero cells was isolated by the guanidium isothiocyanate-cesium chloride method of Chirgwin, et al., (1979). First strand cDNA was synthesized with AMV reverse transcriptase (Life Sciences, St. Petersburg, Fla.), the oligonucleotide primer CDVFSP (SEQ ID NO:68) (5'-CCAGGACATAGCAAGCCAACAGGTC-3'), and RNA from CDV infected cells. CDVFSP (SEQ ID NO:68) primes 80 bp upstream of the CDV fusion (F) start codon, yielding a positive sense single stranded cDNA product which contains the F and hemagglutinin (HA) coding sequences (Barrett et al., 1987; Curran et al., 1991).

The HA-specific open reading frame (ORF) (described in Curran et al., 1991) was amplified from the first strand cDNA product by polymerase chain reaction (PCR) (Engelke et al., 1988). Oligonucleotide primers CDVHA1 (SEQ ID NO:69) (5'-CGATA-TCCGTTAAGTTTGTATCGTAATGCTCCCCTACCAA-GAC-3') and CDVHA2 (SEQ ID NO:70) (5'-GGGATAAAAATTAACGGTTACATGAGAATCTTATA-CGGAC-3') were used in a PCR with the CDVFSP derived first strand cDNA as template. CDVHA1 contains the 3' most region of the vaccinia virus H6 promoter (Perkus, et al., 1989) followed by a sequence which primes from the translation initiation codon into the CDV HA ORF (Curran et al., 1991). CDVHA2 (SEQ ID NO:70) primes from the stop codon of the HA ORF toward the CDV HA 5' end (Curran et al., 1991). The resultant 1.8 kbp PCR product was treated with the Klenow fragment from the *E. coli* DNA polymerase, in the presence of 20 uM dNTPs, to blunt end the fragment. The 1.8 Kbp blunt ended fragment was inserted between the NruI site within the H6 promoter, and the SmaI site 3' of the H6 promoter in pSD554 (see below). The resultant plasmid pCDVHA should have contained the H6 promoted CDV HA ORF, but there was an unexpected deletion at the CDV HA 5' end. Repair of the deletion is described below.

Plasmid pSD554 contains the vaccinia K1L host range gene (Gillard et al., 1986) and vaccinia H6 promoter followed by insertion sites, within flanking vaccinia arms. The flanking vaccinia arms replace the ATI region: open reading frames A25L and A26L (Goebel et al., 1990a,b). pSD554 was prepared in the following manner.

Left and right vaccinia flanking arms were constructed by PCR using the template pSD414 which contains vaccinia SalI B (Goebel et al., 1990a,b). The left arm was synthesized using oligonucleotide primers MPSYN267 (SEQ ID NO:71) (5'-GGGCTGAAGCTTGCTGGCCGCTCATTAGACAA-GCGAATGAGGGAC-3') and MPSYN268 (SEQ ID NO:72) (5'-AGATCTCCCGGGCTCGAGTAATTAAT-TAATTTTTATTACACCAGAAAAGACGGCTTGAGA T C-3') in a PCR with template pSD414. The right arm was synthesized using oligonucleotide primers MPSYN269 (SEQ ID NO:73) (5'-TAATTACTCGAGCCCGGGAGATCTAATT-TAATTTAATTTATATAACTCATTTTTTGAATA T ACT-3') and MPSYN270 (SEQ ID NO:74) (5'-TATCTCGAATTCCCGCGGCTTTAAATGGACGGAAC-TCTTTTCCCC-3') in a PCR with template pSD414. The two PCR-derived fragments containing the left and right arms were combined in a PCR. The resultant PCR product was digested with EcoRI and HindIII and a 0.9 kb fragment was isolated. The 0.9 kb fragment was inserted between the pUC8 EcoRI and HindIII sites. The resultant plasmid pSD541 received the K1L gene, and additional insertion sites, in the following manner.

Plasmid pSD541 was digested with BglII and XhoI and ligated with annealed complementary oligonucleotides MPSYN333 (SEQ ID NO:75) (5'-GATCTTTTGTTAACAAAAACTAATCAGC-TATCGCGAATCGATTCCCGGGGGATCCGGTAC C-3') and MPSYN334 (SEQ ID NO:76) (5'-TCGAGGGTACCGGATCCCCCGGGAATC-GATTCGCGATAGCTGATTAGTTTTTGTTAACAA A A-3'), generating plasmid pSD552. pSD452 (Perkus et al., 1990) contains the K1L gene. pSD452 was digested with HpaI and partially digested with BglII and the resultant 1 kbp fragment containing the K1L gene was inserted between the pSD552 BglII and HpaI sites. The resultant plasmid pSD553 was digested with NruI and a SmaI/NruI fragment containing the vaccinia H6 promoter (Perkus et al., 1989) was inserted. The resultant plasmid, pMP553H6, contains the vaccinia H6 promoter downstream from the K1L gene within the A26L insertion locus.

Plasmid pMP553H6 was digested with NruI and BamHI and ligated with annealed synthetic oligonucleotides MPSYN347 (SEQ ID NO:77) (5'-CGATATCCGTTAAGTTTGTATCGTAATCTGCAGCCC-GGGGGGG-3') and MPSYN348 (SEQ ID NO:78) (5'-GATCCCCCGGGCTGCAGATTACGATACAAACTTAA CGGATATCG-3'). The resultant plasmid pSD554 contains the K1L gene and the H6 promoter followed by insertion sites, within flanking vaccinia sequences which replace the ATI region.

The vaccinia virus H6 promoter and 5' end of the CDV HA ORF were added to pCDVHA as a PCR derived fragment. The ATG of the regulatory region H6 overlaps the CDV HA translation initiation codon in the PCR derived fragment. The vaccinia virus H6 promoter has been described in Perkus, et al., 1989.

pEIVC5L contains the modified H6 promoter (Perkus et al., 1989) and a nonpertinent gene. pEIVC5L was used in a polymerase chain reaction with oligonucleotide primers H65PH (SEQ ID NO:79) (5'-ATCATCAAGCTTGATTCTTTATTCTATAC-3') and CDVHAH6 (SEQ ID NO: 80) (5'-GTCTTGGTAGGGGAGCATTACGATACAAACTTAA-CG-3') to generate a 156 bp fragment. CDVHAH6 contains the 5' 18 base pairs of CDV HA followed by a sequence which primes from the translation initiation codon toward the H6 promoter 5' end. H65PH (SEQ ID NO: 12) contains a HindIII site followed by a sequence which primes from the H6 promoter 5' end toward the 3' end. The 156 base pair PCR-derived H65PH/CDVHAH6 (SEQ ID NO:79/SEQ ID NO: 80) product contains the H6 promoter and the 5' 18 base pairs of the CDV HA coding sequence.

The CDVFSP (SEQ ID NO:68) first strand cDNA product was used in a PCR with oligonucleotide primers CDVHAATG (SEQ ID NO:81) (5'-ATGCTCCCCTACCAAGAC-3') and CDVHAECO (SEQ ID NO:82) (5'-GTAATTAGTAAAATTCACCTTG-3') to generate a 459 base pair fragment. CDVHAATG (SEQ ID NO:81) primes from the translation initiation codon toward the CDV HA 3' end. CDVHAECO (SEQ ID NO:82) primes from position 583 of the following H6 promoted CDV HA sequence toward the CDV HA 5' end. The 156 base pair and 459 base pair PCR-derived fragments were pooled and fused by PCR using H65PH (SEQ ID NO:79) and CDVHAECO (SEQ ID NO: 82) to generate a 597 base pair fragment. The PCR-derived product was digested with HindIII and EcoRI, generating a 520 base pair fragment which contains the H6 promoter and 5' most 387 base pairs of the CDV HA coding sequence. The 520 base pair HindIII/EcoRI digested PCR fragment was inserted between the HindIII and EcoRI sites of pBS-SK (Stratagene, La Jolla, Calif.), yielding pBSCDVHA5S. Plasmid pBSCDVHA5S contains the H6 promoted 5' end of the CDV HA ORF in PBS-SK (Stratagene, La Jolla, Calif.), and the 3' end of the CDV HA ORF was added in the following manner.

Plasmid pCDVHA was digested with SmaI followed by partial digestion with EcoRI to generate a 1.4 kbp fragment containing the 3' end of the CDV HA ORF. The 1.4 kbp pCDVHA EcoRI/SmaI fragment was inserted between the EcoRI and SmaI sites of pBSCDVHA5S. The resultant plasmid pBSCDVHA was digested with BamHI and partially digested with XhoI to generate a 1.9 kbp fragment containing the H6 promoted CDV HA open reading frame. The 1.9 kbp BamHI/XhoI pBSCDVHA fragment was inserted between the BamHI and XhoI sites of pSD553 (see above). The resultant insertion plasmid, pSDCDVHA, contains the H6 promoted CDV HA gene in the ATI insertion site. FIGS. 14A–D show the nucleotide sequence of the H6 promoted CDV HA and CDV HA translation (SEQ ID NOS:83, 84). pSDCDVHA was used in in vivo recombination experiments (Piccini et al., 1987) with NYVAC (vP866; Tartaglia et al., 1992) to generate vP1028.

Example 15

GENERATION OF NYVAC RECOMBINANT CONTAINING THE CANINE DISTEMPER VIRUS FUSION ORF

The first strand cDNA, derived with the oligonucleotide primer CDVFSP (SEQ ID NO:68), containing the CDV F and HA coding sequences is described above. The CDV fusion (F) specific open reading frame (ORF) (described in Barrett et al., 1987) was amplified from the first strand cDNA by PCR. Oligonucleotide primers CDVATGF1 (SEQ ID NO:85) (5'-CATAAATTATTTCATTATCGCGATATC-CGTTAAGTTTGTATCGTAATGCACAAGGGAATC C CCAA AAGC-3') and CDVFT (SEQ ID NO:86) (5'-ATCATCGGATCCATAAAAATCAGTGTGATCTCACAT-AGGATTTCGAAG-3') were used in a PCR with the CDVFSP (SEQ ID NO:67) derived first strand cDNA as template. CDVATGF1 (SEQ ID NO:85) contains the 3' most region of the vaccinia virus H6 promoter (Perkus, et al., 1989) followed by a sequence which primes from the CDV F translation initiation codon into the CDV F ORF (Barrett et al., 1987). CDVFT (SEQ ID NO:86) contains a BamHI site followed by a sequence which primes from the CDV F stop codon toward the CDV F 5' end (Barrett et al., 1987). The resultant PCR product was digested with NruI and BamHI, yielding a 2 kbp fragment which was inserted between the pSD554 (see above) NruI and BamHI sites. The resultant insertion plasmid, pATICDVF1, contains the H6 promoted CDV F ORF (SEQ ID NO:87) in the vaccinia virus ATI insertion locus. FIGS. 15A–D show the nucleotide sequence of H6 promoted CDV F and CDV F translation. pATICDVF1 was used in in vivo recombination (Piccini et al., 1987) experiments with NYVAC (vP866; Tartaglia et al., 1992) to generate vP1029.

Example 16

GENERATION OF ALVAC RECOMBINANT CONTAINING THE CANINE DISTEMPER VIRUS HEMAGGLUTININ ORF

Oligonucleotides RW132 (SEQ ID NO:89) (5'-AGCTTCCCGGGTTAATTAATTAGTCAT-CAGGCAGGGCGAGAACGAGACTATCTGCTCGTT A ATTA ATTAG-3') and RW133 (SEQ ID NO:90) (5'-AGCTCTAATTAATTAACGAGCAGAT-AGTCTCGTTCTCGCCCTGCCTGATGACTAATTAAT T AACC CGGGA-3') were annealed to form a double-stranded linker sequence. The RW132/RW133 (SEQ ID NO:89/SEQ ID NO:90) double-stranded sequence was inserted into the HindIII site 5' of the H6 promoted CDV HA ORF in pBSCDVHA. The resultant plasmid pBSCD-VHAVQ was digested with SmaI, yielding a 2 kbp fragment containing the H6 promoted CDV HA ORF (SEQ ID NO:83) which was inserted into the SmaI site of HC5LSP28. The resultant plasmid pC5CDVHA contains the H6 promoted CDV HA ORF (SEQ ID NO:83) in the C5 locus. pC5CDVHA was used in in vivo recombination (Piccini et al.,1987) experiments with ALVAC (CPpp; Tartaglia et al., 1992) to generate vCP184.

Example 17

GENERATION OF ALVAC RECOMBINANT CONTAINING THE CANINE DISTEMPER VIRUS FUSION GENE

Plasmid pATICDVF1 contains the H6 promoted CDV fusion (F) ORF. The 2 kbp pATICDVF1 NruI/XhoI fragment, containing the 3' 28 base pairs of the vaccinia virus H6 promoter (Perkus, et al., 1989) followed by the CDV F open reading frame (SEQ ID NO:87) was inserted between the NruI and XhoI sites of VQH6C3LSA.2. The resultant plasmid pMM115 contains the H6 promoted CDVF ORF (SEQ ID NO:87) in the C3 locus. pMM115 was used in in vivo recombination (Piccini et al., 1987) experiments with ALVAC (CPpp; Tartaglia et al.,1992) to generate vCP194.

Example 18

GENERATION OF NYVAC RECOMBINANT CONTAINING THE CANINE DISTEMPER VIRUS FUSION AND HEMAGGLUTININ ORFs

Plasmids pC5CDVHA and pMM115 have been described above. The 2 kbp pC5CDVHA SmaI fragment, which contains the H6 promoted CDV HA ORF (SEQ ID NO:83), was inserted into the SmaI site of the I4L vector pSD550. The resultant plasmid pMM124 was used as a vector for the H6 promoted CDV F ORF (SEQ ID NO:87).

Plasmid pSD550 was constructed by insertion of complementary oligonucleotides 539A (SEQ ID NO:91) (5'-AGAAAAATCAGTTAGCTAAGATCTC-CCGGGCTCGAGGGTACCGGATCCTGATTAGTTAAT T TTTGT-3') and 539B (SEQ ID NO:92) (5'-GATCACAAAAATTAACTAATCAGGATC-CGGTACCCTCGAGCCCGGGAGATCTTAGCTAAC TGATT TTTCT-3') between the BglII and SmaI sites of the I4L insertion vector pSD548 (Tartaglia et al., 1992). The resultant plasmid pSD550 contains additional I4L insertion sites between the pSD548 BglII and SmaI sites.

The 2.2 kbp pMM115 BamHI fragment, which contains the H6 promoted CDV F ORF (SEQ ID NO:87), was inserted into the BamHI site of pMM124. The resultant plasmid pMM126 contains the H6 promoted CDV F ORF and H6 promoted CDV HA ORF (SEQ ID NO:93), with their transcripts directed away from each other, in the I4L locus.

FIGS. 16A–G show the 4343 bp sequence derived from plasmid pMM126 of the H6 promoted canine distemper virus (CDV) F, H6 promoted CDV HA, NYVAC sequences flanking I4L, and translations of CDV open reading frames: (SEQ ID NOS:93, 94, 95). The 5' end of the H6 promoted CDV F is at position 2199. The CDV F coding sequence is from position 2075 through position 90. The 5' end of the H6 promoted CDV HA is at position 2355. The CDV HA coding sequence is from position 2479 through 4290. pMM126 was used in in vivo recombination (Piccini et al., 1987) experiments with NYVAC (vP866; Tartaglia et al., 1992) to generate vP1202.

Example 19

GENERATION OF ALVAC RECOMBINANT CONTAINING THE CANINE DISTEMPER VIRUS FUSION AND HEMAGGLUTININ ORFs

The 2 kbp pBSCDVHAVQ SmaI fragment, which contains the H6 promoted CDV HA ORF (SEQ ID NO:83), was inserted into the HC5LSP28 SmaI site. The resultant plasmid pC5LCDVHA was used as a vector for the H6 promoted CDV F ORF (SEQ ID NO:87). The pC5LCDVHA vector was prepared by partial SmaI digestion, followed by BamHI digestion, and isolation of the 6.5 kbp fragment which contains the H6 promoted CDV HA ORF (SEQ ID NO:83), ALVAC flanking arms, and pUC8. The 2.1 kbp pATICDVF1

HpaI/BamHI fragment, containing the H6 promoted CDV F ORF (SEQ ID NO:87), was inserted between the above pC5LCDVHA SmaI and BamHI sites. The resultant plasmid pC5LCDVHAF1 contains the H6 promoted CDV F (SEQ ID NO:87) and H6 promoted CDV HA ORFSs (SEQ ID NO:83), with their transcripts directed away from each other, in the C5 locus.

pC5CDVHAF1 was digested with BamHI and treated with the Klenow fragment from the *E. coli* DNA polymerase, in the presence of 20 mM dNTPs to blunt end the BamHI site, followed by digestion with SmaI. The 4.2 kbp blunt ended BamHI to SmaI fragment, containing the H6 promoted CDV F and H6 promoted CDV HA ORFs (SEQ ID NO:96), was inserted into the SmaI site of C6L. FIGS. 17A–G show the predicted nucleotide sequence of the H6 promoted canine distemper virus (CDV) F, H6 promoted CDV HA, ALVAC sequences flanking C6, and translations of CDV open reading frames (SEQ ID NOS:96, 97, 98). pMM103 was used for confirmation of all junction sequences and flanking sequences. The 5' end of the H6 promoted CDV F is at position 2307. The CDV F coding sequence is from position 2183 through position 198. The 5' end of the H6 promoted CDV HA is at position 2464. The CDV HA coding sequence is from position 2588 through 4399 (SEQ ID NO:96). The resultant plasmid pMM103 was used in in vivo recombination (Piccini et al., 1987) experiments with ALVAC (CPpp; Tartaglia et al., 1992) to generate vCP258.

Example 20

GENERATION OF C3, C5 AND C6 ALVAC VECTORS

Locus C3 surrounds the EcoRI site within the 3.4 kbp canarypox PvuII clone pRW764.2. The C3 vector VQH6C3LSA.2 was constructed to remove the C3 ORF in the following manner.

An 8.5 kbp canarypox BglII fragment, containing the C3 ORF, was inserted into the BamHI site of PBS-SK (Stratagene, La Jolla, Calif.) to form pWW5. Oligonucleotide primers RG277 (SEQ ID NO:99) (5'-CAGTTGGTACCACTGGTATTTTATTTCAG-3') and RG278 (SEQ ID NO:100) (5'-TATCTGAATTCCTGCAGCCCGGGTTTT-TATAGCTAATTAGTCAAATGTGAGTTAATAT TAG-3') were used in a PCR with the template pWW5 to generate a 280 bp fragment. Oligonucleotide primers RG279 (SEQ ID NO: 101) (5'-TCGCTGAATTCGATATCAAGCTTATC-GATTTTTATGACTAGTTAATCAAATAAAAAGCAT A CAAGC-3') and RG280 (SEQ ID NO:102) (5'-TTATCGAGCTCTGTAACATCAGTATCTAAC-3') were used in a PCR with the template pWW5 to generate a 250 bp fragment. The 280 bp fragment was digested with Asp718 and EcoRI, the 250 bp fragment was digested with SacI and EcoRI, and the two fragments were inserted together between the Asp718 and SacI sites of PBS-SK (Stratagene, La Jolla, Calif.). The resultant plasmid is pC3I.

Oligonucleotide primers CP16 (SEQ ID NO:103) (5'-TCCGGTACCGCGGCCGCAGATATTTGTTAGCTTCT-GC-3') and CP17 (SEQ ID NO: 104)(5'-TCGCTCGAGTAGGATACCTACCTACTACCTACG-3') were used in a PCR with template pWW5. The resultant 604 base pair canarypox fragment was digested with Asp718 and XhoI and inserted between the Asp718 and XhoI sites of pIBI25 (International Biotechnologies, Inc., New Haven, Conn.), yielding SPC3LA. The 908 base pair pWW5 NsiI/SsPI canarypox fragment was inserted between the SPC3LA EcoRV and NsiI sites. The resultant plasmid SPCPLAX contains 1444 base pairs of canarypox upstream of the C3 locus.

pXX4 contains a 6.5 kbp NsiI canarypox fragment in the PstI site of pBS-SK (Stratagene, La Jolla, Calif.). Oligonucleotide primers CP19 (SEQ ID NO:105) (5'-TCGCTCGAGCTTTCTTGACAATAACATAG-3') and CP20 (SEQ ID NO:106) (5'-TAGGAGCTCTTTATACTACTGGGTTACAAC-3') were used in a PCR with the template pXX4 to generate a 279 base pair canarypox fragment. The 279 base pair PCR derived canarypox fragment was digested with XhoI and SacI for insertion between the SacI and XhoI sites of pIBI25 (International Biotechnologies, Inc., New Haven, Conn.). The resultant plasmid is SPC3RA.

Additional insertion sites were added between the pC3I EcoRI and ClaI sites by insertion of annealed complementary oligonucleotides CP12 (SEQ ID NO:107) (5'-AATTCCTCGAGGGATCC-3') and CP13 (SEQ ID NO:109) (5'-CGGGATCCCTCGAGG-3'), yielding plasmid SPCP3S. The 261 base pair BglII/SacI SPC3RA fragment and the 2178 base pair BglII/StyI pXX4 fragment were inserted together between the SPCP3S StyI and SacI sites. The resultant plasmid CPRAL contains 2572 base pairs of canarypox downstream of the C3 locus. The 1436 base pair Asp718/AccI SPCPLAX fragment was inserted between the SPCP3S Asp718 and AccI sites. The resultant plasmid CPLAL contains 1457 base pairs of canarypox upstream of the C3 locus. The 2438 base pair StyI/SacI CPRAL fragment was inserted between the CPLAL StyI and SacI sites. The resultant plasmid CP3L contains 1457 base pairs of canarypox upstream of the C3 locus.

The H6 promoter was added to CP3L as a PCR derived fragment. Plasmid pRW838 contains the H6 promoter and a nonpertinent gene. Oligonucleotide primers CP21 (SEQ ID NO:105) (5'-TCGGGATCCGGGTTAATTAATTAGTT-ATTAGACAAGGTG-3') and CP22 (SEQ ID NO:110) (5'-TAGGAATTCCTCGAGTACGATACAAACTTAAGCGG-ATATCG-3') were used in a PCR with the pRW838 template. The 200 base pair PCR derived fragment, containing the H6 promoter, was digested with BamHI and EcoRI for insertion between the CP3L BamHI and EcoRI sites. The resultant plasmid was designated VQH6CP3L.

One of the VQH6CP3L canarypox flanking arms was shortened by inserting the annealed complementary oligonucleotides CP34 (SEQ ID NO:111) (5'-GGCCGCGTCGACATGCA-3') and CP35 (SEQ ID NO: 112) (5'-TGTCGACGC-3') between the VQH6CP3L NsiI and NotI sites. The resultant plasmid VQH6C3LSA.2 contains the vaccinia virus H6 promoter followed by C3 insertion sites.

Locus C5 surrounds the two BglII sites in the 0.9 kbp canarypox PvuII clone pRW764.5. The C5 vector HC5LSP28 was constructed to remove the C5 ORF in the following manner.

Oligonucleotide primers C5A (SEQ ID NO:113) (5'-ATCATCGAATTCTGAATGTTAAATGTTATACTTTG-3') and C5B (SEQ ID NO:114) (5'-GGGGGTACCTTTGAGAGTACCACTTCAG-3') were used in a PCR with genomic canarypox DNA as template. The resultant 1.5 kbp fragment was digested at the C5A end with EcoRI and the other end remained blunt for insertion between the EcoRI and SmaI sites of pUC8, yielding C5LAB. Oligonucleotide primers C5C. (SEQ ID NO:115)

(5'-GGGTCTAGAGCGGCCGCTTATAAAGATCTAAAA-TGCATAATTTC-3') and C5DA (SEQ ID NO:116) (5'-ATCATCCTGCAGGTATTCTAAACTAGGAATAGATG-3') were used in a PCR with genomic canarypox DNA as template. The resultant 400 base pair fragment was digested at the C5DA end with PstI and the other end remained blunt for insertion between the SmaI and PstI sites of C5LAB, yielding pC5L. Annealed complementary oligonucleotides CP26 (SEQ ID NO:117) (5'-GTACGTGACTAATTAGCTATAAAAAG-GATCCGGTACCCTCGAGTCTAGAATCGATCCCGG G TTTT TATGACTAGTTAATCAC-3') and CP27 (SEQ ID NO:118) (5'-GGCCGTGATTAACTAGTCATAAAAAC-CCGGGATCGATTCTAGACTCGAGGGTACCGGATC C TTTT TATAGCTAATTAGTCAC-3') were inserted between the pC5L Asp718 and NotI sites. The resultant plasmid HC5LSP28 is a locus C5 vector.

Locus C6 surrounds the two EcoRI sites in the 1.3 kbp canarypox PvuII clone pRW764.7. The C6 vector pC6L was constructed to remove the C6 ORF in the following manner.

Oligonucleotide primers C6A1 (SEQ ID NO:119) (5'-ATCATCGAGCTCGCGGCCGCCTATCAAAAGTCTT-AATGAGTT-3'), C6B1 (SEQ ID NO:120) (5'-GAATTCCTCGAGCTGCAGCCCGGGTTTT-TATAGCTAATTAGTCATTTTTTCGTAAGTAAG T ATTT TTATTTAA-3'), C6C1 (SEQ ID NO:121) (5'-CCCGGGCTGCAGCTCGAGGAATTCTTTT-TATTGATTAACTAGTCAAATGAGTATATATAA T TGAA AAAGTAA-3') and C6D1 (SEQ ID NO:122) (5'-GATGATGGTACCTTCATAAATACAAGTTTGATTAAA-CTTAAGTTG-3') were used to construct pC6L. Oligonucleotide primers C6A1 (SEQ ID NO:115) and C6B1 (SEQ ID NO:120) were used in a PCR with canarypox DNA template to generate a 380 base pair fragment. A second PCR reaction with the canarypox DNA template, and oligonucleotide primers C6C1 (SEQ ID NO:121) and C6D1 (SEQ ID NO:122), generated a 1155 base pair fragment. The two PCR reaction products were pooled and primed for a final PCR with C6A1 (SEQ ID NO:119) and C6D1 (SEQ ID NO:122), yielding a 1613 base pair fragment. The final PCR product was digested with SacI and KpnI, and inserted between the SacI and KpnI sites of pBS-SK (Stratagene, La Jolla, Calif.). The resultant C6 insertion plasmid was designated as pC6L.

Example 21

EXPRESSION ANALYSIS OF NYVAC- AND ALVAC-BASED CDV RECOMBINANT VIRUSES

Infected Vero cell lysates were prepared and immunoprecipitation analyses were performed as described previously (Taylor et al., 1990) using antiserum from CDV-seropositive dogs (for NYVAC-based recombinants) and monospecific antiserum derived from rabbits inoculated with vaccinia virus recombinants expressing either the CDV HA or F glycoprotein (for ALVAC-based recombinants). Results from these analyses have confirmed expression of the appropriate CDV gene product by the recombinant viruses.

Example 22

PROTECTION OF DOGS AGAINST CDV CHALLENGE BY ALVAC-CDVHF (vCP258)

The protective efficacy of the ALVAC-based CDV HA and F recombinant virus was assessed by exposure of dogs to a live CDV challenge following vaccination. In this experiment, 13 CDV seronegative beagles were divided into two vaccinated groups (3 dogs for $10^7$ pfu vCP258 vaccine dose and 4 dogs for $10^{5.5}$ pfu vaccine dose) and a non-vaccinated control group (6 dogs). Vaccination consisted of two subcutaneous inoculations with either $10^7$ pfu (group 1) or $10^{5.5}$ pfu (group 2) of vCP258 three weeks apart. On day 42, all dogs were challenged by a intracranial administration of a 1:10 NVSL CDV challenge stock. Dogs were observed daily for 28 days following challenge to monitor morbidity/mortality.

No local or systemic adverse reactions were noted in dogs vaccinated with vCP258. All non-vaccinated control dogs developed clinical signs of CDV infection including anorexia, conjunctivitis, depression, weight loss, and dehydration from 6 to 17 days post-challenge. Four febrile peaks (>103.5° F.) were observed on days 1, 3, 8, and 13 days post-challenge. Four of the 6 control animals had more severe clinical manifestations. In fact, one of these dogs died 12 days post-challenge while the other three were euthanized between 13 and 17 days post-challenge. The two surviving control animals, which had milder disease symptomology, started to recover and, in fact, began gaining weight 19 days post-challenge.

Significantly, no dogs in either vaccine dose group developed clinical signs of CDV infection. They all gained weight and displayed normal behavior during the observation period. Further, no febrile episodes were observed.

Table 21 lists the CDV-specific serological responses in each group at various times prior to challenge. The antibody titers are expressed as the 50% neutralization endpoint and represent the mean titer for each group. Interestingly, despite the $10^{5.5}$ pfu vaccine dose not eliciting equivalent levels of CDV serum neutralizing activity, all dogs vaccinated with this lower dose were completely protected against the virulent CDV challenge.

TABLE 21

| Vaccine Group | CDV-specific Serological Responses | | | |
|---|---|---|---|---|
| | Day 0 | Day 14 | Day 21 | Day 42 |
| $10^{5.5}$ | <1:3 | 1:16 | 1:21 | 1:50 |
| $10^{7.0}$ | <1:3 | 1:19 | 1:19 | 1:151 |
| Control | <1:3 | ND | ND | <1:3 |

ND = not determined

Having thus described in detail preferred embodiments of the present invention, it is to be understood that the invention defined by the appended claims is not to be limited by particular details set forth in the above descriptions as many apparent variations thereof are possible without departing from the spirit or scope thereof.

REFERENCES

1. Adams, J. M., and D. T. Imagawa, Proc. Soc. Exper. Biol. Med. 96, 240–244 (1957).
2. Alkhatib, G., and D. Briedis, Virology 150, 479–490 (1986).
3. Altenburger, W., C.-P. Suter and J. Altenburger, Archives Virol. 105, 15–27 (1989).
4. Avery, R. J., and J. Niven., Infect. and Immun. 26, 795–801 (1979).
5. Barrett, T., Clarke, D. K., Evans, S. A., and Rima, B. K., Virus Research 8, 373–386 (1987).
6. Behbehani, A. M., Microbiological Reviews 47, 455–509 (1983).

7. Bergoin, M., and Dales, S., In Comparative Virology, eds. K. Maramorosch and E. Kurstak, (Academic Press, New York) pp. 169–205 (1971).
8. Bertholet, C., Drillien, R., and Wittek, R., Proc. Natl. Acad. Sci. USA 82, 2096–2100 (1985).
9. Boursnell, M. E. G., Green, P. F., Campell, J. I. A., Deuter, A., Peters, R. W., Tomley, F. M., Samson, A. C. R., Chambers, P., Emmerson, P. T., and Binns, M. M. J. Gen. Virol. 71, 621–628 (1990a).
10. Boursnell, M. E. G., Green, P. F., Campell, J. I. A., Deuter, A., Peters, R. W., Tomley, F. M., Samson, A. C. R., Emmerson, P. T., and Binns, M. M. Vet. Microbiol. 23, 305–316 (1990b).
11. Boursnell, M. E. G., Green, P. F., Samson, A. C. R., Campell, J. I. A., Deuter, A., Peters, R. W., Millar, N. S., Emmerson, P. T., and Binns, M. M. Virology 178, 297–300 (1990c).
12. Buller, R. M. L., G. L. Smith, Cremer, K., Notkins, A. L., and Moss, B., Nature 317, 813–815 (1985).
13. Buller, R. M. L., Chakrabarti, S., Cooper, J. A., Twardzik, D. R., and Moss, B., J.Virol. 62, 866–874 (1988).
14. Cadoz, M., A. Strady, B. Meignier, J. Taylor, J. Tartaglia, E. Paoletti and S. Plotkin, The Lancet, 339, 1429 (1992).
15. Chambers, P., N. S. Millar, and P. T. Emmerson, J. Gen. Virol. 67, 2685–2694 (1986).
16. Child, S. J., Palumbo, G. J., Buller, R. M. L., and Hruby, D. E. Virology 174, 625–629 (1990).
17. Chirgwin, J. M., Przybyla, A. E., MacDonald, R. J., and Rutter, W. J. Biochemistry. 18, 5294–5299 (1979).
18. Clewell, D. B. and D. R. Helinski, Proc. Natl. Acad. Sci. USA 62, 1159–1166 (1969).
19. Clewell, D. B., J. Bacteriol 110, 667–676 (1972).
20. Colinas, R. J., R. C. Condit and E. Paoletti, Virus Research 18, 49–70 (1990).
21. Cooney E. L., Corrier A. C., Greenberg P. D., et al., Lancet 337, 567–572 (1991).
22. Curran, M. D., Clarke, D. K., and Rima, B. K., J. Gen. Virol. 72, 443–447 (1991).
23. DeLay, P. D., S. S. Stone, D. T. Karzon, S. Katz, and J. Enders, Am. J. Vet. Res. 26, 1359–1373 (1965).
24. Diallo, A., Vet. Micro. 23, 155–163 (1990).
25. Dowling, P. C., B. M. Blumberg, J. Menonna, J. E. Adamus, P. Cook, J. C. Crowley, D. Kolakofsky, and S. D. Cook, J. Gen. Virol. 67, 1987–1992 (1986).
26. Dreyfuss, G., Adam, S. A., and Choi, Y. D., Mol. Cell. Biol. 4, 415–423 (1984).
27. Drillien, R., F. Koehren and A. Kirn, Virology 111, 488–499 (1981).
28. Drillien, R., D. Spehner, A. Kirn, P. Giraudon, R. Buckland, F. Wild, and J. P. Lecocq, Proc. Natl. Acad. Sci. USA 85, 1252–1256 (1988).
29. Edbauer, C., R. Weinberg, J. Taylor, A. Rey-Senelonge, J. F. Bouquet, P. Desmettre, and E. Paoletti, Virology 179, 901–904 (1990).
30. Engelke, D. R., Hoener, P. A., and Collins, F. S., Proc. Natl. Acad. Sci. USA 85, 544–548 (1988).
31. Espion, D., De Henau, S., Letellier, C., Wemers, C.-D., Brasseur, R., Young, J. F., Gross, M., Rosenberg, M., Meulemans, G, and Burny, A. Arch. Virol. 95, 79–95 (1987)
32. Etinger H. M., Altenburger W., Vaccine 9, 470–472 (1991).
33. Fenner, F., Virology 5, 502–529 (1958).
34. Fenner, F., P. A. Bachmann, E. P. J. Gibbs, F. A. Murphy, M. J. Studdert, and D. O. White, In Veterinary Virology, ed. F. Fenner, (Academic Press, Inc., New York) pp. 485–503 (1987).
35. Flexner, C., Hugen, A., and Moss, B., Nature 330, 259–262 (1987).
36. Fries et al., 32nd Interscience Conference on Antimicrobial Agents and Chemotherapy, Anaheim, Calif. (October 1992).
37. Funahashi, S., T. Sato and H. Shida, J. Gen. Virol. 69, 35–47 (1988).
38. Garten, W., Kohama, T., and H.-D. Klenk. J. Gen. Virol. 51, 207–211 (1980).
39. Ghendon, Y. Z., and Chernos, V. I., Acta Virol. 8, 359–368 (1964).
40. Gillard, S., Spehner, D., Drillien, R., and Kirn, A., Proc. Natl. Acad. Sci. USA 83, 5573–5577 (1986).
41. Gillespie, J. H., and D. T. Karzon, Proc. Soc. Exp. Biol Med. 105, 547–551 (1960).
42. Goebel, S. J., Johnson, G. P., Perkus, M. E., Davis, S. W., Winslow, J. P., Paoletti, E., Virology 179, 247–266 (1990a).
43. Goebel, S. J., G. P. Johnson, M. E. Perkus, S. W. Davis, J. P. Winslow and E. Paoletti, Virology 179, 517–563 (1990b).
44. Goldstein, D. J. and S. K. Weller, Virology 166, 41–51 (1988).
45. Graves, M. C., S. M. Silver, and P. W. Choppin, Virology 86, 254–263 (1978).
46. Guo, P., Goebel, S., Davis, S., Perkus, M. E., Languet, B., Desmettre, P., Allen, G., and Paoletti, E., J. Virol. 63, 4189–4198 (1989).
47. Guo, P., S. Goebel, S. Davis, M. E. Perkus, J. Taylor, E. Norton, G. Allen, B. Languet, P. Desmettre, and E. Paoletti, J. Virol. 64, 2399–2406 (1990).
48. Hall, W. W., R. A. Lamb, and P. W. Choppin, Virology 100, 433–449 (1980).
49. Homma, M., and M. Ohuchi, J. Virol. 12, 1457–1465 (1973).
50. Hruby, D. E. and L. A. Ball, J. Virol. 43, 403–409 (1982).
51. Hruby, D. E., R. A. Maki, D. B. Miller and L. A. Ball, Proc. Natl. Acad. Sci. USA 80, 3411–3415 (1983).
52. Ichihashi, Y. and Dales, S., Virology 46, 533–543 (1971).
53. Imagawa, D. T., P. Goret, and J. M. Adams, Proc. Natl. Acad. Sci. USA 46, 1119–1123 (1960).
54. Itamura, S., H. Iinuma, H. Shida, Y. Morikawa, K. Nerome and A. Oya, J. Gen. Virol. 71, 2859–2865 (1990).
55. Jacobson, J. G., D. A. Leib, D. J. Goldstein, C. L. Bogard, P. A. Schaffer, S. K. Weller and D. M. Coen, Virology 173, 276–283 (1989).
56. Jamieson, A. T., G. A. Gentry and J. H. Subak-Sharpe, J. Gen. Virol. 24, 465–480 (1974).
57. Karzon, D. T., Pediatrics 16, 809–818 (1955).
58. Karzon, D. T., Annals of the N.Y. Academy of Sci. 101, 527–539 (1962).
59. Kato, S., M. Takahashi, S. Kameyama and J. Kamahora, Biken's 2, 353–363 (1959).
60. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
61. Kleitmann W., Schottle A., Kleitmann B., et al., In Cell Culture Rabies Vaccines and Their Protective Effect in Man., ed. Kuwert/Wiktor/Koprowski, (International Green Cross—Geneva) pp. 330–337 (1981).
62. Kotwal, G. J. and Moss, B., Nature (Lond.) 335, 176–178 (1988).
63. Kotwal, G. J., A. W. Hugin and B. Moss, Virology 171, 579–587 (1989a).
64. Kotwal, G. J. and B. Moss, J. Virol. 63, 600–606 (1989b).
65. Kotwal, G. J., S. N. Isaacs, R. McKenzie, M. M. Frank and B. Moss, Science 250, 827–830 (1990).

66. Lai, A. C.-K. and B. G.-T. Pogo, Virus Res. 12, 239–250 (1989).
67. Le, L., Brasseur, R., Wemers, C., Meulemans, G., and Burny, A. Virus Genes 1, 333–350 (1988).
68. Mandecki, W., Proc. Natl. Acad. Sci. USA 83, 7177–7182 (1986).
69. Maniatis, T., Fritsch, E. F., and Sambrook, J. In Molecular cloning: a laboratory manual, (Cold Spring Harbor Laboratory, Cold Spring Harbor, N.Y.) (1982).
70. Matthews, R. E. F., Intervirology 17, 42–44 (1982b).
71. McGinnes, L. W. and Morrison, T. G. Virus Res. 5, 343–356 (1986).
72. Merz, D. C., A. Scheid, and P. Choppin, J. Exper. Med. 151, 275–288 (1980).
73. Morgan, A. J., M. Mackett, S. Finerty, J. R. Arrand, F. T. Scullion and M. A. Epstein, J. Med. Virol. 25, 189–195 (1988).
74. Moss, B., E. Winters and J. A. Cooper, J. Virol. 40, 387–395 (1981).
75. Moura, R. A., and J. Warren, J. Bact. 82, 702–705 (1961).
76. Nagai, Y., T. Yoshida, M. Hamaguchi, H. Naruse, M. Iinuma, K. Maeno, and T. Matsumoto, Microbiol. Immunol. 24, 173–177 (1980).
77. Nagai, Y., H. D. Klenk, and R. Rott, Virology 72, 494–508 (1976).
78. Norrby, E., and Y. Gollmar, Infect. and Immun. 11, 231–239 (1975).
79. Norrby, E. Utter, G., Orvell, C., and M. J. G. Appel, J. Virol. 58, 536–541 (1986).
80. Norrby, E., G. Enders-Ruckle, and V. ter Meulen, J. Infect. Dis. 132, 262–269 (1975).
81. Ogawa, R., Yanagida, N., Saeki, S., Saito, S., Ohkawa, S., Gotoh, H., Kodama, K., Kamogawa, K., Sawagucki, K., and Iritani, Y. Vaccine 8, 486–490 (1990).
82. Orvell, C., and E. Norrby, J. Gen. Virol. 50, 231–245 (1980).
83. Paez, E., S. Dallo and M. Esteban, Proc. Natl. Acad. Sci. USA 82, 3365–3369 (1985).
84. Palumbo, G. J., Pickup, D. J., Fredrickson, T. N., Mcintyre, L. J., and Buller, R. M. L., Virology 172, 262–273 (1989).
85. Panicali, D. and E. Paoletti, Proc. Natl. Acad. Sci. USA 79, 4927–4931 (1982).
86. Panicali, D., Davis, S. W., Mercer, S. R., and Paoletti, E., J. Virol. 37, 1000–1010 (1981).
87. Patel, D. D. and Pickup, D. J. EMBO J. 6, 3787–3794 (1987)
88. Patel, D. D., Ray, C. A., Drucker, R. P., and Pickup, D. J., Proc. Natl. Acad. Sci. USA 85, 9431–9435 (1988).
89. Perkus, M. E., D. Panicali, S. Mercer and E. Paoletti, Virology 152, 285–297 (1986).
90. Perkus, M. E., A. Piccini, B. R. Lipinskas and E. Paoletti, Science 229, 981–984 (1985).
91. Perkus, M. E., Limbach, K., and Paoletti, E., J. Virol. 63, 3829–3836 (1989).
92. Perkus, M. E., Goebel, S. J., Davis, S. W., Johnson, G. P., Limbach, K., Norton, E. K., and Paoletti, E., Virology 179, 276–286 (1990).
93. Perkus, M. E., S. J. Goebel, S. W. Davis, G. P. Johnson, E. K. Norton and E. Paoletti, Virology 180, 406–410 (1991).
94. Piccini, A., M. E. Perkus, and E. Paoletti, Methods in Enzymology 153, 545–563 (1987).
95. Pickup, D. J., B. S. Ink, B. L. Parsons, W. Hu and W. K. Joklik, Proc. Natl. Acad. Sci. USA 81, 6817–6821 (1984).
96. Pickup, D. J., B. S. Ink, W. Hu, C. A. Ray and W. K. Joklik, Proc. Natl. Acad. Sci. USA 83, 7698–7702 (1986).
97. Reed, L. J. and Muench, H., Am. J. Hyg. 27, 493–497 (1938).
98. Richardson, C. D., A. Berkovich, S. Rozenblatt, and W. Bellini, J. Virol. 54, 186–193 (1985).
99. Richardson, C., D. Hull, P. Greer, K. Hasel, A. Berkovich, G. Englund, W. Bellini, B. Rima, and R. Lazzarini, Virology 155, 508–523 (1986).
100. Rickinson, A. B., Rowe, M., Hart, I. J., Yao, Q. T., Hendersen, L. E., Ralein, H. and Epstein, M. A. Cell. Immunol. 87, 646–658 (1984).
101. Roberts, J. A., J. Immunol. 94, 622–628 (1965).
102. Sanger, F., Nickeln, S. Coulson, A. R., Proc. Natl. Acad. Sci. 74, 5463–5467 (1977).
103. Sanger, F., S. Nicklen, and A. R. Coulson, Proc. Natl. Acad. Sci. USA 74, 5463–5467 (1977).
104. Schmidtt, J. F. C. and H. G. Stunnenberg, J. Virol. 62, 1889–1897 (1988).
105. Seligmann, E. B., In Laboratory Techniques in Rabies, eds. M. M. Kaplan and H. Koprowski, (World Health Organization, Geneva) pp. 279–285 (1973).
106. Shapira, S. K., J. Chou, F. V. Richaud, and M. J. Casadaban, Gene 25, 71–82 (1983).
107. Shapira, S. K., Chou, J., Richaud, F. V. and Casadaban, M. J., Gene 25, 71–82 (1983).
108. Shida, H., Virology 150, 451–462 (1986).
109. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
110. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
111. Slabaugh, M., N. Roseman, R. Davis and C. Mathews, J. Virol. 62, 519–527 (1988).
112. Smith, J. S., P. A. Yager and G. M. Baer, In Laboratory Techniques in Rabies, eds. M. M. Kaplan and H. Koprowski (WHO Geneva) pp. 354–357 (1973).
113. Stanberry, L. R., S. Kit and M. G. Myers, J. Virol. 55, 322–328 (1985).
114. Stephenson, J. R. and V. ter Meulen, Proc. Nat. Acad. Sci. USA 76, 6601–6605 (1979).
115. Tabor, S. and C. C. Richardson, Proc. Natl. Acad. Sci. USA 84, 4767–4771 (1987).
116. Tartaglia, J., Perkus, M. E., Taylor, J., Norton, E. K., Audonnet, J.-C., Cox, W. L, Davis, S. W., Van Der Hoeven, J., Meignier, B., Riviere, M., Languet, B., Paoletti, E., Virology 188, 217–232 (1992).
117. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In *AIDS Research Reviews*, W. Koff, F. Wong-Staal & R. C. Kenedy, Eds., Vol. 3, Marcel Dekker, New York (In press) (1993a).
118. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990).
119. Tartaglia, J., Jarrett, O., Desmettre, P., Paoletti, E., J. Virol. 67, 2370–2375 (1993b).
120. Taylor, J., Edbauer, C., Rey-Senelonge, A., Bouquet, J.-F., Norton, E., Goebel, S., Desmettre, P., Paoletti, E., J. Virol. 64, 1441–1450 (1990).
121. Taylor, G., E. J. Stott, G. Wertz and A. Ball, J. Gen. Virol. 72, 125–130 (1991a).
122. Taylor, J., C. Trimarchi, R. Weinberg, B. Languet, F. Guillemin, P. Desmettre and E. Paoletti, Vaccine 9, 190–193 (1991b).

123. Taylor, J., C. Trimarchi, R. Weinberg, B. Languet, F. Guillemin, P. Desmettre & E. Paoletti, Vaccine 9, 190 (1991c).
124. Taylor, J., S. Pincus, J. Tartaglia, C. Richardson, G. Alkhatib, D. Briedis, M. Appel, E. Norton, and E. Paoletti, J. Virol. 65, 4263–4272 (1991d).
125. Taylor, J., R. Weinberg, B. Languet, P. Desmettre, and E. Paoletti, Vaccine 6, 497–503 (1988b).
126. Taylor, J., Weinberg, R., Kawaoka, Y., Webster, R. G., and Paoletti, E., Vaccine 6, 504–508 (1988a).
127. Taylor, J., R. Weinberg, J. Tartaglia, C. Richardson, G. Alkhatib, D. Briedis, M. Appel, E. Norton & E. Paoletti, Virology 187, 321–328 (1992).
128. Tizard, I., J. Am. Vet. Med. Assoc. 196, 1851–1858 (1990).
129. Toyoda, T., Sakaguchi, T., Imai, K., Inocencio, N. M., Gotoh, B., Hamaguchi, M., and Nagai, Y. Virology 158, 242–247 (1987).
130. Warren, J., M. K. Nadel, E. Slater, and S. J. Millian, Amer. J. Vet. Res. 21, 111–119 (1960).
131. Weir, J. P. and B. Moss J. Virol. 46, 530–537 (1983).
132. Wild, F., P. Giraudon, D. Spehner, R. Drillien, and J-P. Lecocq, Vaccine 8, 441–442 (1990).
133. Yuen, L., and Moss, B., Proc. Natl. Acad. Sci. USA 84, 6417–6421 (1987).
134. Zhou, J., L. Crawford, L. McLean, X. Sun, M. Stanley, N. Almond and G. L. Smith, J. Gen. Virol. 71, 2185–2190 (1990).

---

What is claimed is:

1. A recombinant poxvirus comprising exogenous DNA in a nonessential region of the poxvirus genome, said exogenous DNA encoding canine distemper virus fusion protein and canine distemper virus hemagglutinin glycoprotein, wherein the poxvirus expresses the proteins and the poxvirus is selected from the group consisting of:

(i) recombinant vaccinia virus wherein regions C7L–K1L, J2R, B13R+B14R, A56R and I4L have been deleted therefrom, or wherein the open reading frames for the thymidine kinase gene, the hemorrhagic region, the A type inclusion body region, the hemagglutinin gene, the host range gene region, and the large subunit, ribonucleotide reductase gene have been deleted therefrom; and (ii) ALVAC or a poxvirus having all the identifying characteristics of ALVAC.

2. The poxvirus of claim 1 wherein the poxvirus is the vaccinia virus.

3. The poxvirus of claim 1 which is a NYVAC recombinant virus.

4. The recombinant poxvirus of claim 1 which is vP1202.

5. The poxvirus of claim 1 wherein said poxvirus is the ALVAC virus.

6. The recombinant poxvirus of claim 1 which is vCP258.

7. A recombinant poxvirus comprising exogenous DNA in a nonessential region of the poxvirus genome, said exogenous DNA encoding canine distemper virus fusion protein and the poxvirus is ALVAC or a poxvirus having all the identifying characteristics of ALVAC.

8. A recombinant poxvirus comprising exogenous DNA in a nonessential region of the poxvirus genome, said exogenous DNA encoding canine distemper virus hemagglutinin glycoprotein and the poxvirus is ALVAC or a poxvirus having all the identifying characteristics of ALVAC.

9. A recombinant poxvirus comprising exogenous DNA in a nonessential region of the poxvirus genome, wherein the exogenous DNA codes for canine distemper virus hemagglutinin glycoprotein and the poxvirus is a recombinant vaccinia virus wherein regions C7L–K1L, J2R, B13R+B14R, A56R and I4L have been deleted therefrom, or wherein the open reading frames for the thymidine kinase gene, the hemorrhagic region, the A type inclusion body region, the hemagglutinin gene, the host range gene region, and the large subunit, ribonucleotide reductase gene have been deleted therefrom.

10. The recombinant poxvirus of claim 9 which is vP1028.

11. A recombinant poxvirus comprising exogenous DNA in a nonessential region of the poxvirus genome, wherein the exogenous DNA codes for canine distemper virus fusion protein and the poxvirus is a recombinant vaccinia virus wherein regions C7L–K1L, J2R, B13R+B14R, A56R and I4L have been deleted therefrom, or wherein the open reading frames for the thymidine kinase gene, the hemorrhagic region, the A type inclusion body region, the hemagglutinin gene, the host range gene region, and the large subunit, ribonucleotide reductase gene have been deleted therefrom.

12. The recombinant poxvirus of claim 11 which is vP1029.

13. vCP184, or vCP194.

14. A method for inducing an antigenic or immunological response in a dog or other carnivore against canine distemper virus comprising administering to said dog or other carnivore a composition comprising a poxvirus as claimed in any one of claims 1, 7, 8, 9, 6, or 11 in admixture with a suitable carrier.

15. A composition for inducing an antigenic or immunological response comprising a poxvirus as claimed in any one of claims 1, 7, 8, 9, 6, or 11 in admixture with a suitable carrier.

16. A method for expressing a gene product in a cell culture in vitro comprising introducing into the cell a virus as claimed in ant one of claims 1, 7, 8, 9, or 11.

* * * * *